US012492168B2

(12) United States Patent
Frey et al.

(10) Patent No.: US 12,492,168 B2

(45) Date of Patent: Dec. 9, 2025

(54) ORGANIC MATERIAL FOR AN ELECTRONIC OPTOELECTRONIC DEVICE AND ELECTRONIC DEVICE COMPRISING THE ORGANIC MATERIAL

(71) Applicant: Novaled GmbH, Dresden (DE)

(72) Inventors: Julien Frey, Dresden (DE); Elena Galan, Dresden (DE); Carsten Rothe, Dresden (DE)

(73) Assignee: Novaled GmbH, Dresden (DE)

( * ) Notice: Subject to any disclaimer, the term of this patent is extended or adjusted under 35 U.S.C. 154(b) by 1140 days.

(21) Appl. No.: 16/968,227

(22) PCT Filed: Jan. 31, 2019

(86) PCT No.: PCT/EP2019/052411

§ 371 (c)(1),
(2) Date: Aug. 7, 2020

(87) PCT Pub. No.: WO2019/154713

PCT Pub. Date: Aug. 15, 2019

(65) Prior Publication Data

US 2021/0036230 A1 Feb. 4, 2021

(30) Foreign Application Priority Data

Feb. 7, 2018 (EP) .................................... 18155487

(51) Int. Cl.
*C07C 255/33* (2006.01)
*C07C 255/50* (2006.01)
(Continued)

(52) U.S. Cl.
CPC .......... *C07D 213/16* (2013.01); *C07C 255/33* (2013.01); *C07D 215/06* (2013.01);
(Continued)

(58) Field of Classification Search
CPC ............... H10K 85/615; H10K 85/654; H10K 85/6572; C07C 255/33; C07D 213/16; C07D 215/06; C07D 235/08
See application file for complete search history.

(56) References Cited

U.S. PATENT DOCUMENTS

2002/0182441 A1* 12/2002 Lamansky .......... C07F 15/0033 428/917
2016/0043327 A1* 2/2016 Yoo ...................... H10K 85/615 257/40
(Continued)

FOREIGN PATENT DOCUMENTS

KR 20170039020 A * 4/2017
WO 2015/009076 A1 1/2015
(Continued)

OTHER PUBLICATIONS

Kang et al., machine translation of KR-20170039020-A (2017) pp. 1-43. (Year: 2017).*
(Continued)

*Primary Examiner* — Jennifer A Boyd
*Assistant Examiner* — Rachel Simbana
(74) *Attorney, Agent, or Firm* — Eversheds Sutherland (US) LLP

(57) ABSTRACT

The present invention relates to an organic material and to an electronic device comprising the organic material, particularly to an electroluminescent device, particularly to an organic light emitting diode (OLED), wherein the semiconducting material comprises a multiple-substituted phenyl moiety, an aryl moiety with at least two fused rings, a polar moiety and optional linkers between these moieties.

18 Claims, 2 Drawing Sheets

100

(51) Int. Cl.

| | |
|---|---|
| ***C07D 213/16*** | (2006.01) |
| ***C07D 215/04*** | (2006.01) |
| ***C07D 215/06*** | (2006.01) |
| ***C07D 217/02*** | (2006.01) |
| ***C07D 235/08*** | (2006.01) |
| ***C07D 263/57*** | (2006.01) |
| ***C07D 277/66*** | (2006.01) |
| ***C07F 9/53*** | (2006.01) |
| ***C09K 11/06*** | (2006.01) |
| ***H10K 50/16*** | (2023.01) |
| ***H10K 50/18*** | (2023.01) |
| ***H10K 85/60*** | (2023.01) |

(52) U.S. Cl.

CPC ............ *C07D 235/08* (2013.01); *C09K 11/06* (2013.01); *H10K 85/615* (2023.02); *H10K 85/654* (2023.02); *H10K 85/6572* (2023.02); *C07C 2603/24* (2017.05); *C09K 2211/1018* (2013.01); *H10K 50/16* (2023.02); *H10K 50/18* (2023.02)

(56) References Cited

U.S. PATENT DOCUMENTS

| | | | | |
|---|---|---|---|---|
| 2018/0331292 | A1* | 11/2018 | Kalisz | C23C 28/00 |
| 2019/0296238 | A1 | 9/2019 | Cha et al. | |
| 2020/0212314 | A1* | 7/2020 | Numata | H10K 85/6574 |

FOREIGN PATENT DOCUMENTS

| | | | |
|---|---|---|---|
| WO | 2017/089399 | A1 | 6/2017 |
| WO | 2017/178392 | A1 | 10/2017 |
| WO | 2017209538 | A1 | 12/2017 |

OTHER PUBLICATIONS

Request for the Submission of an Opinion issued in Korea application No. 10-2020-7025140, dated Aug. 25, 2023, 17 pages.

PCT International Search Report and Written Opinion for PCT Application No. PCT/EP2019/052411 mailed Apr. 2, 2019 (10 pages).

Notification of First Office Action issued in China application No. 201980012186.3, dated Feb. 17, 2023, 18 pages.

* cited by examiner

ORGANIC MATERIAL FOR AN ELECTRONIC OPTOELECTRONIC DEVICE AND ELECTRONIC DEVICE COMPRISING THE ORGANIC MATERIAL

CROSS REFERENCE TO RELATED APPLICATIONS

This application is a U.S. national phase application of international application no. PCT/EP2019/052411, filed Jan. 31, 2019, which claims priority to European Application No. 18155487.4, filed Feb. 7, 2018. The content of these applications is incorporated herein by reference.

TECHNICAL FIELD

The present invention relates to an organic material and to an electronic device comprising the organic material, particularly to an electroluminescent device, particularly to an organic light emitting diode (OLED); the invention pertains also to a device comprising the electric device and/or the electroluminescent device, particularly to a display device, particularly to a display device comprising the OLED.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. There is continuing demand for development of improved materials, with the aim that operational voltage is as low as possible while brightness/luminance is high, and that injection and flow of holes and electrons is balanced, so that an OLED having the above-described structure has excellent efficiency and/or a long lifetime.

One of well-established approaches for achieving low operational voltages and high current densities/luminances is electrical p- and/or n-doping in charge injection/charge transport layers, and especially redox doping which generates doped layers with high charge carrier concentrations.

DISCLOSURE

Aspects of the present invention provide an organic material for an electronic device, particularly for a light-emitting device comprising an emission layer and at least two electrodes, for increasing the efficiency, such as the external quantum efficiency EQE, and for achieving low operating voltage and long lifetime, particularly in top and/or bottom emission organic light-emitting diodes (OLEDs).

Another aspect of the present invention provides an electronic device, particularly an electroluminescent device comprising the organic material. Still another aspect of the present invention provides a display device comprising the electroluminescent device.

According to an aspect of the present invention, there is provided an organic material for an electroluminescent device having the Formula I:

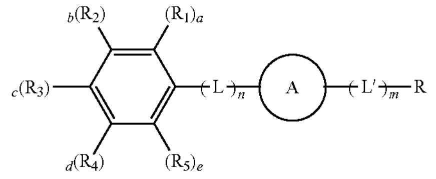

(I)

wherein $R^1$ to $R^5$ are independently a substituted or unsubstituted $C_6$ to $C_{30}$ aryl group or a substituted or unsubstituted $C_2$ to $C_{30}$ heteroaryl group, whereby at least two of R1, R2, R3, R4, R5 and L (or A if n=0) are in ortho-Position to each other at the benzene ring B a to e are independently from each other 0 or 1 and $1 \leq a+b+c+d+e \leq 5$;

A is a $C_{10}$ to $C_{20}$ arylene group with at least two fused aryl rings.

L and L' are independently selected from each other a $C_2$ to $C_{30}$ heteroaryl group or $C_6$ to $C_{20}$ aryl group n and m are independently from each other 0, 1 or 2, whereby when n or m are 2 then each of the both L and/or L' can be different from the other; and R is a polar uncharged organic moiety, whereby when A is anthracenyl, R is not substituted or unsubstituted dibenzofuranyl.

In the present specification, when a definition is not otherwise provided, "substituted" refers to one substituted with a deuterium, $C_1$ to $C_{12}$ alkyl and $C_1$ to $C_{12}$ alkoxy.

In the present specification, when a definition is not otherwise provided, an "alkyl group" refers to a saturated aliphatic hydrocarbyl group. The alkyl group may be a $C_1$ to $C_{12}$ alkyl group. More specifically, the alkyl group may be a $C_1$ to $C_{10}$ alkyl group or a $C_1$ to $C_6$ alkyl group. For example, a $C_1$ to $C_4$ alkyl group includes 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group.

The term "cycloalkyl" refers to saturated hydrocarbyl groups derived from a cycloalkane by formal abstraction of one hydrogen atom from a ring atom comprised in the corresponding cycloalkane. Examples of the cycloalkyl group may be a cyclopropyl group, a cyclobutyl group, a cyclopentyl group, a cyclohexyl group, a methylcyclohexyl group, an adamantly group and the like.

The term "hetero" is understood the way that at least one carbon atom, in a structure which may be formed by covalently bound carbon atoms, is replaced by another polyvalent atom. Preferably, the heteroatoms are selected from B, Si, N, P, O, S; more preferably from N, P, O, S.

In the present specification, "aryl group" refers to a hydrocarbyl group which can be created by formal abstraction of one hydrogen atom from an aromatic ring in the corresponding aromatic hydrocarbon. Aromatic hydrocarbon refers to a hydrocarbon which contains at least one aromatic ring or aromatic ring system. Aromatic ring or aromatic ring system refers to a planar ring or ring system of covalently bound carbon atoms, wherein the planar ring or ring system comprises a conjugated system of delocalized electrons fulfilling Hückel's rule. Examples of aryl groups include monocyclic groups like phenyl or tolyl, polycyclic groups which comprise more aromatic rings linked by single bonds, like biphenylyl, and polycyclic groups comprising fused rings, like naphtyl or fluoren-2-yl.

Analogously, under heteroaryl, it is especially where suitable understood a group derived by formal abstraction of one ring hydrogen from a heterocyclic aromatic ring in a compound comprising at least one such ring.

Under heterocycloalkyl, it is especially where suitable understood a group derived by formal abstraction of one ring hydrogen from a saturated cycloalkyl ring in a compound comprising at least one such ring.

The term "fused aryl rings" is understood the way that two aryl rings are considered fused when they share at least two common $sp^2$-hybridized carbon atoms In the present specification, the single bond refers to a direct bond.

In the context of the present invention, "different" means that the compounds do not have an identical chemical structure.

The term "free of", "does not contain", "does not comprise" does not exclude impurities which may be present in the compounds prior to deposition. Impurities have no technical effect with respect to the object achieved by the present invention.

The term "contacting sandwiched" refers to an arrangement of three layers whereby the layer in the middle is in direct contact with the two adjacent layers.

In the specification, hole characteristics refer to an ability to donate an electron to form a hole when an electric field is applied and that a hole formed in the anode may be easily injected into the emission layer and transported in the emission layer due to conductive characteristics according to a highest occupied molecular orbital (HOMO) level.

In addition, electron characteristics refer to an ability to accept an electron when an electric field is applied and that electron formed in the cathode may be easily injected into the emission layer and transported in the emission layer due to conductive characteristics according to a lowest unoccupied molecular orbital (LUMO) level.

Advantageous Effects

Surprisingly, it was found that the organic material according to the invention solves the problem underlying the present invention by enabling devices in various aspects superior over the organic electroluminescent devices known in the art, in particular with respect to voltage and/or efficiency. These parameters are important for high efficiency and thereby increased battery life of a mobile device, for example a mobile display device.

According to a further embodiment of the invention, the organic compound has a dipole moment of ≥0.6 Debye, preferably 1 Debye, further preferred ≥1,5 Debye.

According to a further embodiment of the invention, R is not dibenzofuranyl.

According to a further embodiment of the invention, R is a moiety which is chosen so that the dipole moment of the compound R-phenyl is ≥0.6 Debye, preferably ≥0.7 Debye According to a further embodiment of the invention, R is selected from substituted or unsubstituted $C_2$ to $C_{30}$ heteroaryl group and CN.

According to a further embodiment of the invention, R is selected from

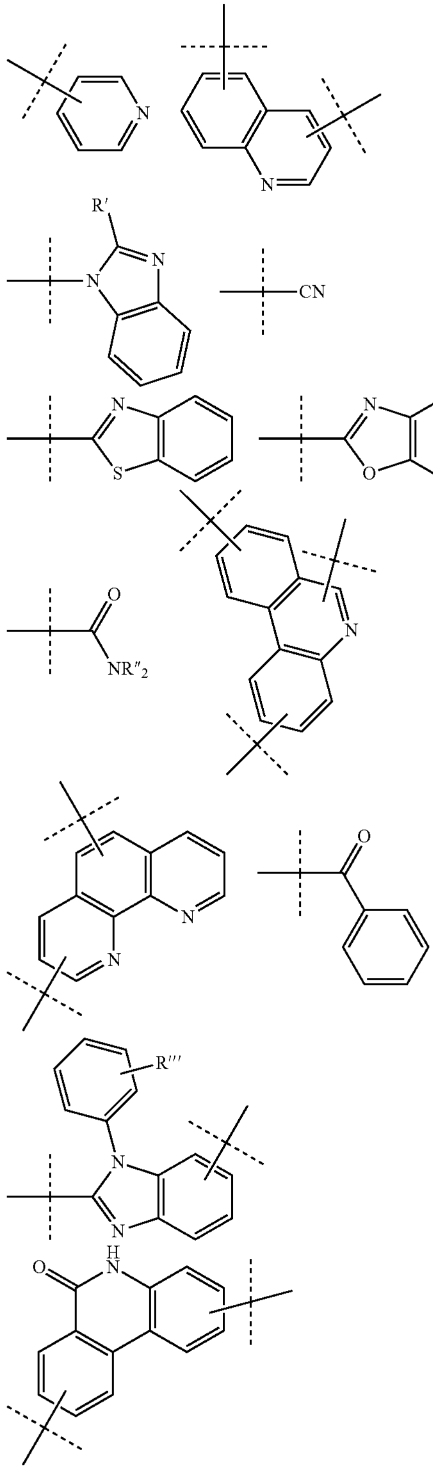

with R' being alkyl, cycloalkyl, aryl, heteroaryl; and R" and R'" being independently selected from alkyl, cycloalkyl, aryl, heteroaryl.

According to a further embodiment, R is linked to L' at any of the positions indicated with an open bond crossed by a dashed line.

The dipole moments, calculated with B3LYP_Gaussian/6-31G*, gas phase, for compounds R-Phenyl for preferred R's are given in the following Table 1:
TABLE 1
Calculated Dipole moments for selected compounds R-Phenyl
| # | structure | dipole moment [Debye] |
|---|---|---|
| 1 | 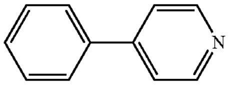 [SMILES: c1ccc(-c2ccncc2)cc1] | 2.86 |
| 2 | 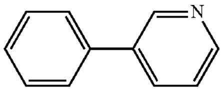 | 2.3 |
| 3 | 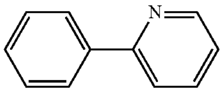 [SMILES: c1ccc(-c2ccccn2)cc1] | 1.71 |
| 4 | 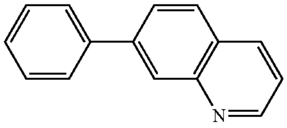 [SMILES: c1ccc(-c2ccc3cccnc3c2)cc1] | 1.91 |
| 5 | 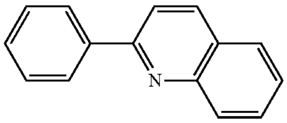 [SMILES: c1ccc(-c2ccc3ccccc3n2)cc1] | 1.53 |
| 6 | 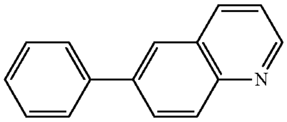 [SMILES: c1ccc(-c2ccc3ncccc3c2)cc1] | 2.11 |
| 7 | 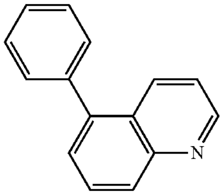 [SMILES: c1ccc(-c2cccc3ncccc23)cc1] | 2.31 |
| 8 | 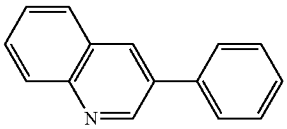 [SMILES: c1ccc(-c2cnc3ccccc3c2)cc1] | 2.06 |
| 9 | 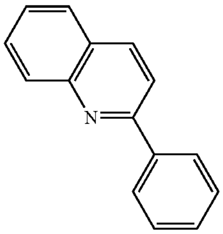 [SMILES: c1ccc(-c2ccc3ccccc3n2)cc1] | 1.53 |
| 10 | 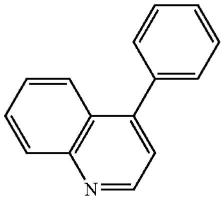 [SMILES: c1ccc(-c2ccnc3ccccc23)cc1] | 2.57 |
| 11 | 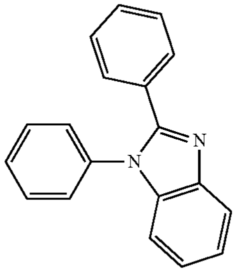 [SMILES: c1ccc(-c2nc3ccccc3n2-c2ccccc2)cc1] | 3.71 |
| 12 | 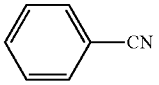 | 4.56 |
| 13 | 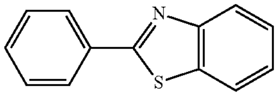 | 0.66 |
| 14 | 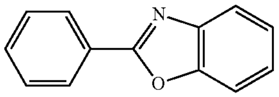 [SMILES: c1ccc(-c2nc3ccccc3o2)cc1] | 1.15 |
| 15 | 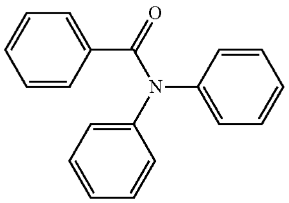 [SMILES: O=C(c1ccccc1)N(c1ccccc1)c1ccccc1] | 3.34 |
| 16 | 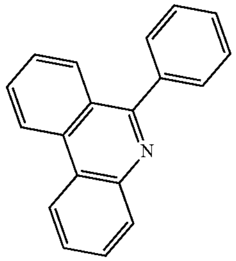 [SMILES: c1ccc(-c2nc3ccccc3c3ccccc23)cc1] | 1.8 |

TABLE 1-continued

| Calculated Dipole moments for selected compounds R-Phenyl | | |
|---|---|---|
| # | structure | dipole moment [Debye] |
| 17 | 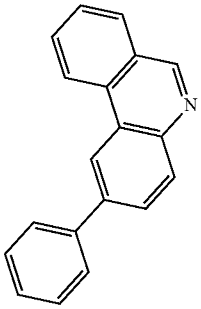 [SMILES: c1ccc(-c2ccc3ncc4ccccc4c3c2)cc1] | 2.34 |
| 18 | 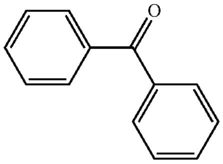 [SMILES: O=C(c1ccccc1)c1ccccc1] | 2.97 |
| 19 | 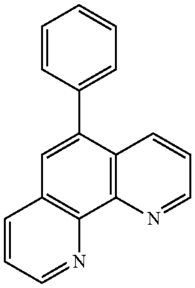 [SMILES: c1ccc(-c2cc3cccnc3c3ncccc23)cc1] | 3.58 |
| 20 | 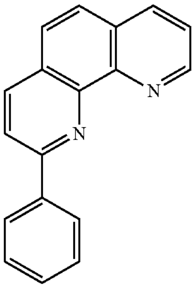 [SMILES: c1ccc(-c2ccc3ccc4cccnc4c3n2)cc1] | 2.67 |
| 21 | 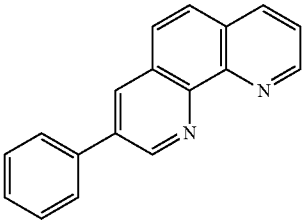 [SMILES: c1ccc(-c2cnc3c(ccc4cccnc43)c2)cc1] | 3.13 |
| 22 | 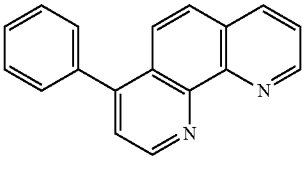 [SMILES: c1ccc(-c2ccnc3c2ccc2cccnc23)cc1] | 3.68 |
| 23 | 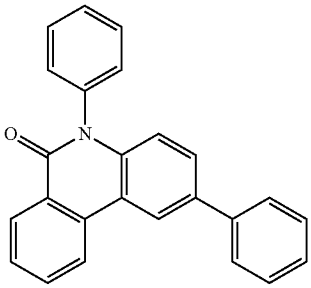 [SMILES: O=c1c2ccccc2c2cc(-c3ccccc3)ccc2n1-c1ccccc1] | 2.68 |

According to a further embodiment, 1≤a+b+c+d+e≤4.

According to a further embodiment, 2≤a+b+c+d+e≤3.

According to a further embodiment, when a+b+c+d+e≤4, then either a or e are 0 and the other is 1.

According to a further embodiment, the substituents at the ring B $R_1$ to $R_5$ are phenyl.

According to a further embodiment, the substituents at the ring B $R_1$ to $R_5$ as well as the indices a to e are selected so that the substituted ring B has one of the following structures:

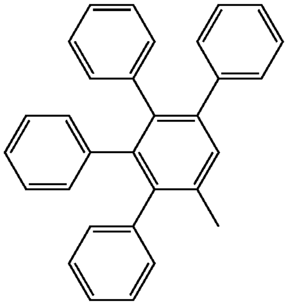

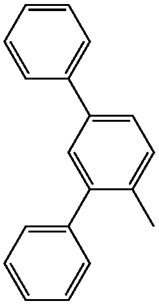

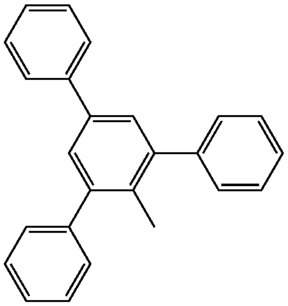

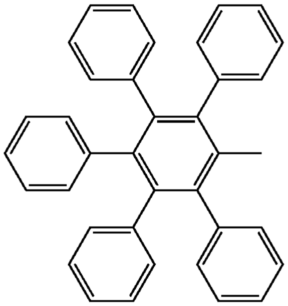

-continued

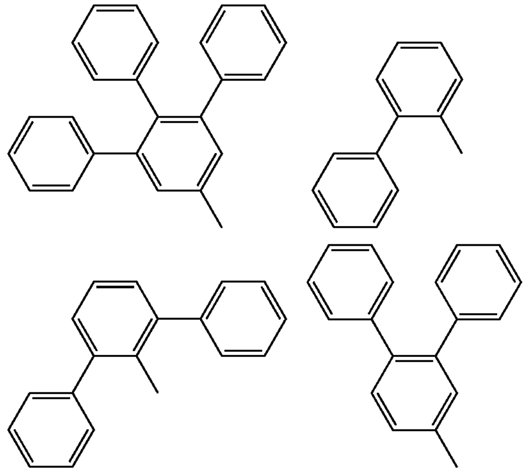

According to a further embodiment of the invention, A is selected from the groups comprising

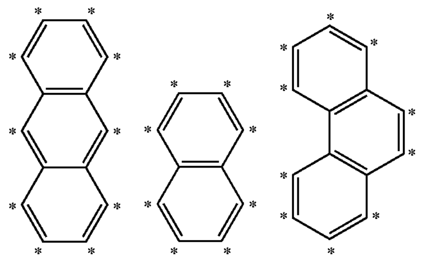

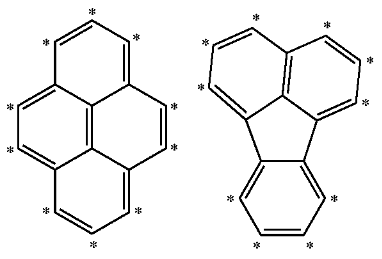

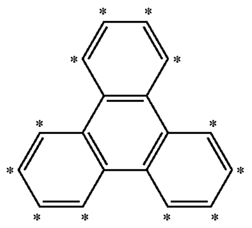

wherein L and L' (or B and R, respectively, when n and m are 0) are linked to any position marked by "*".

According to a further embodiment, A is anthracenyl.

According to a further embodiment of the invention, L and/or L' are selected from the groups comprising

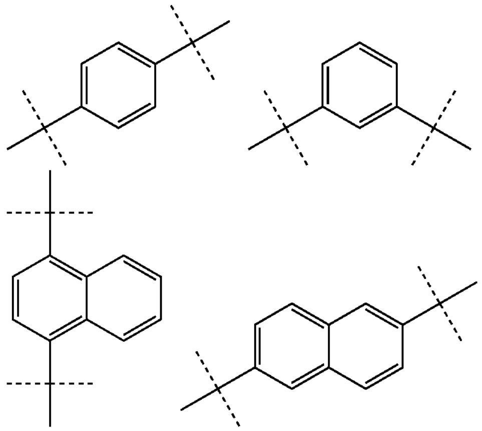

According to a further embodiment of the invention, n is 1 or 2. Preferably n is 1.

According to a further embodiment of the invention, m is 0 or 1. Preferably m is 1.

The inventors have surprisingly found that particularly good performance can be achieved when using the organic material according to the invention in an electron transport layer in an optoelectronic device.

Additionally or alternatively the inventors have surprisingly found that particularly good performance can be achieved when using the organic organic material according to the invention in or as an hole blocking layer in an optoelectronic device.

The present invention furthermore relates to a electronic device comprising a first electrode, a second electrode, and arranged between the first and second electrode, a layer comprising the organic material according to the invention.

According to a further embodiment, the electronic device comprises a hole blocking layer comprising a compound according to the invention.

According to a further embodiment, the electronic device comprises an electon transport layer comprising a compound according to the invention.

According to a further embodiment, the electronic device is an electroluminescent device, preferably an organic light emitting diode.

The present invention furthermore relates to a display device comprising an electronic device according to the present invention, preferably, the display device comprises an organic light emitting diode according to the present invention.

The specific arrangements mentioned herein as preferred were found to be particularly advantageous.

Further an organic electroluminescent device having high efficiency and/or long life-span may be realized.

Hereinafter, the organic material and the device comprising it are described in more detail Organic Material Similar as other compounds comprised in the inventive device outside the emitting layer, the organic material may not emit light under the operation condition of an electroluminescent device, for example an OLED.

Particularly preferred may be compounds of formula I with the following structures A1 to A195
A1
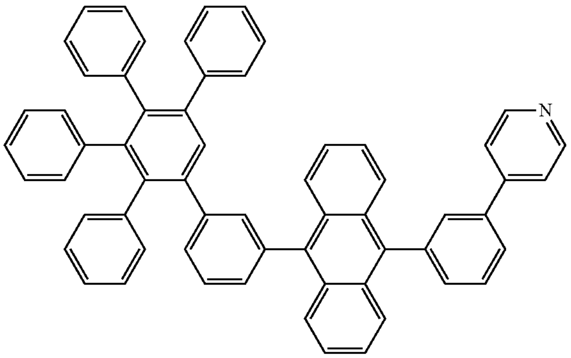
A2
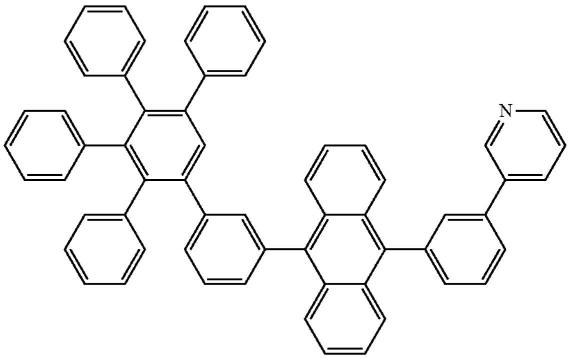
A3
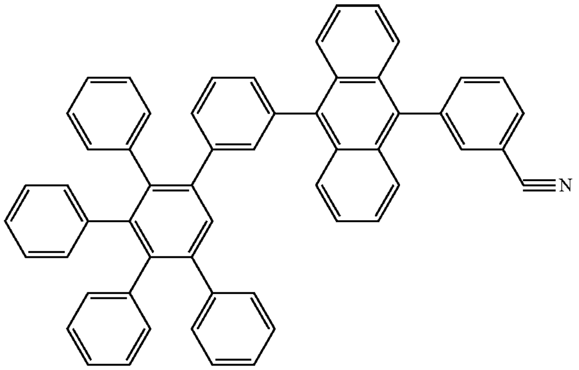
A4
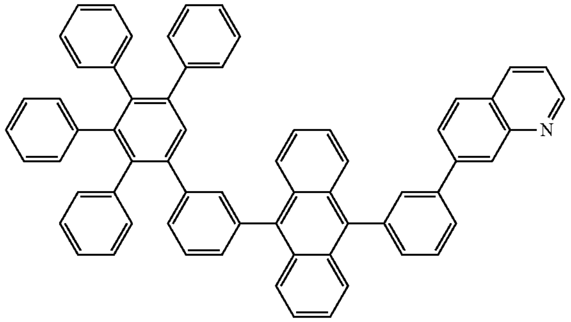
-continued
A5
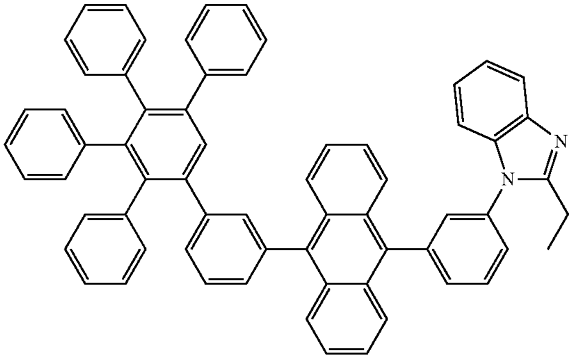
A6
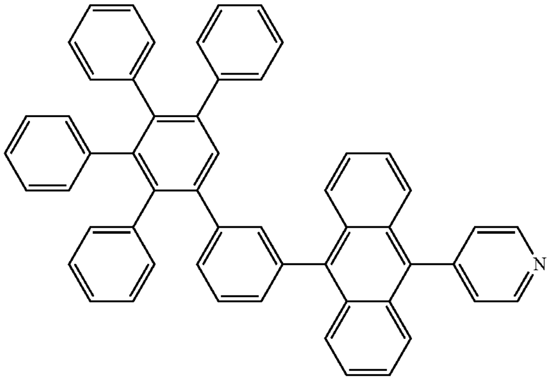
A7
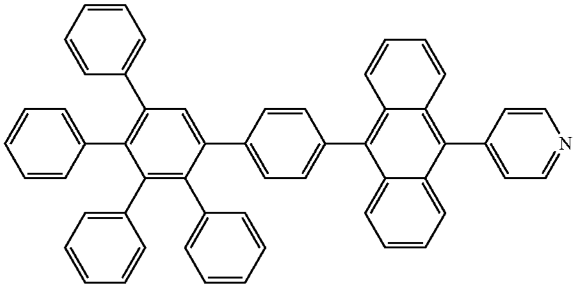
A8
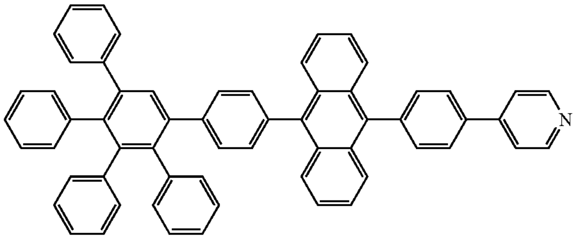

-continued
A9
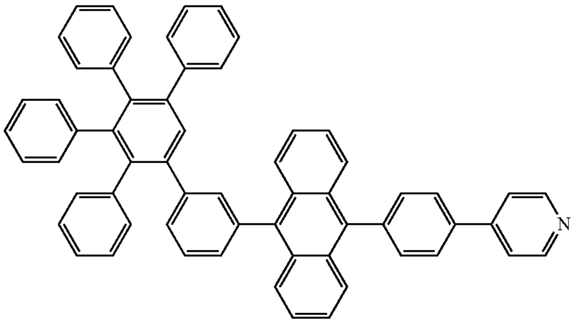
A10
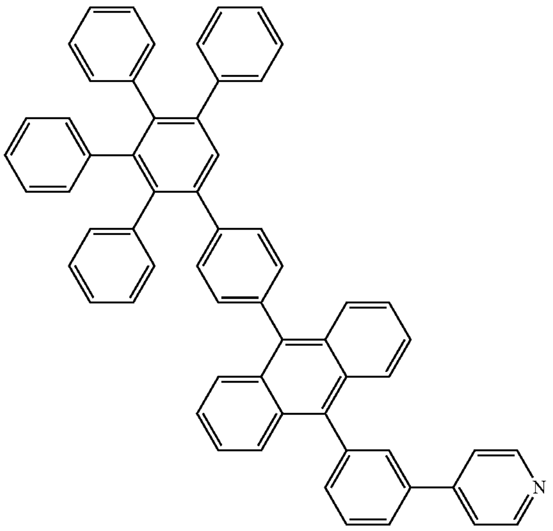
A11
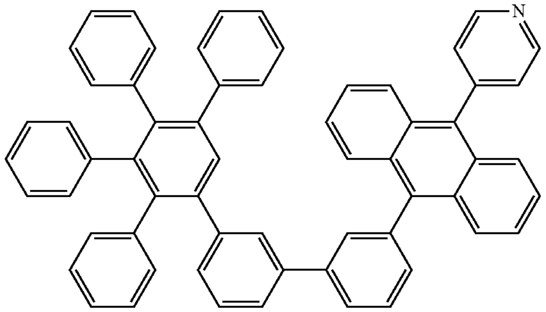
A12
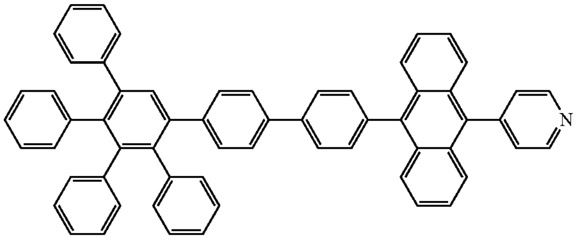
-continued
A13
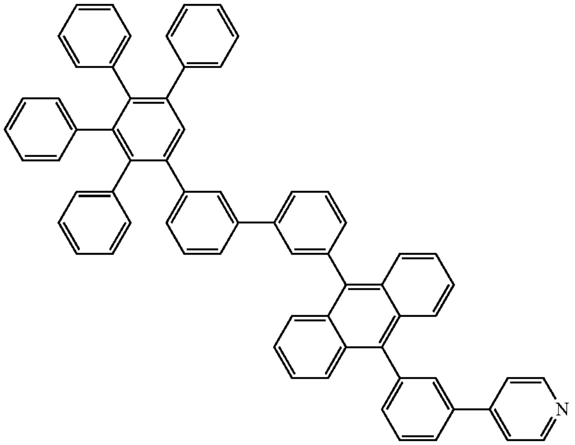
A14
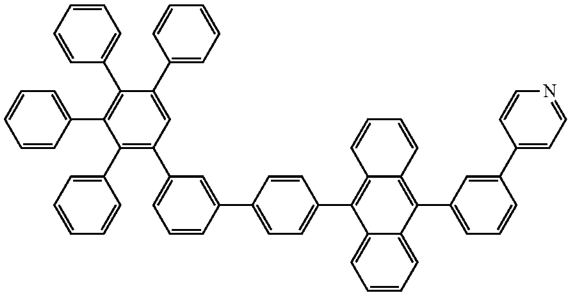
A15
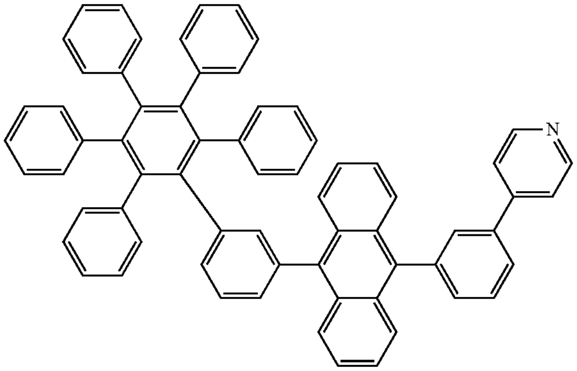
A16
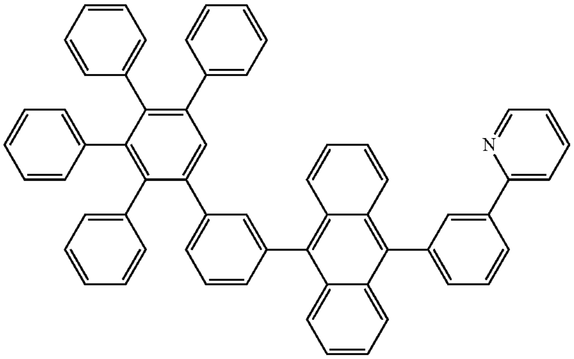

-continued
A17
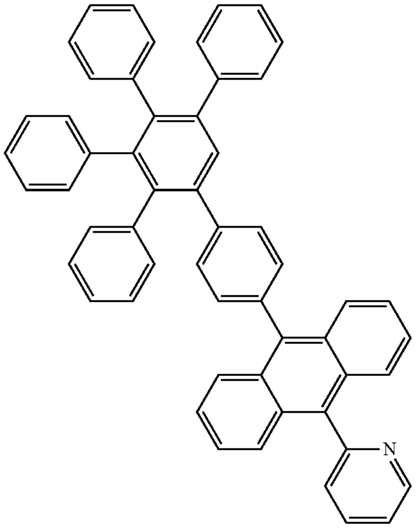
A18
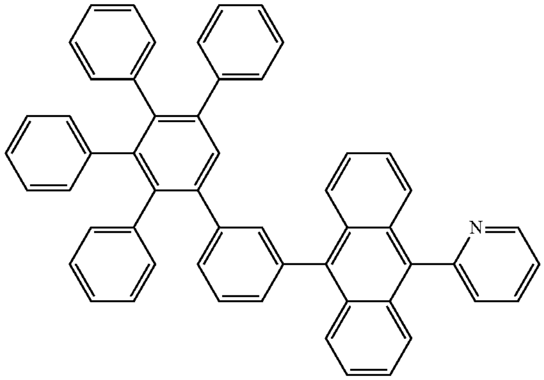
A19
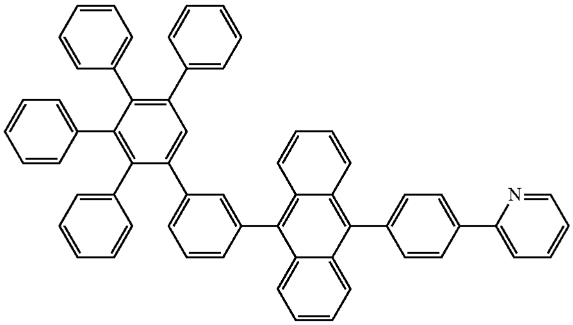
A20
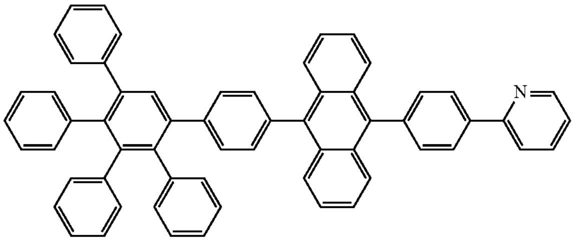
-continued
A21
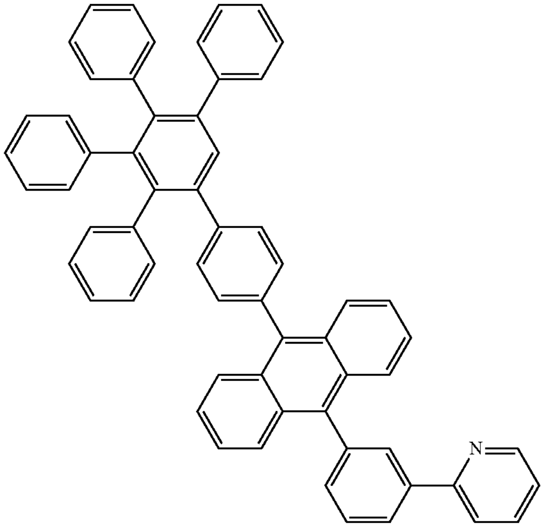
A22
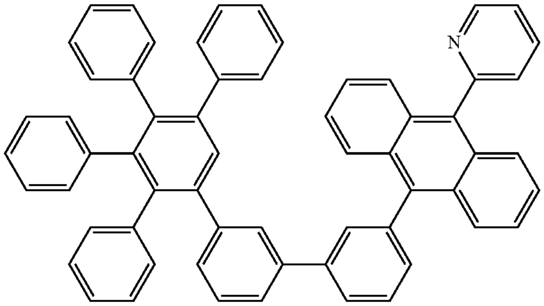
A23
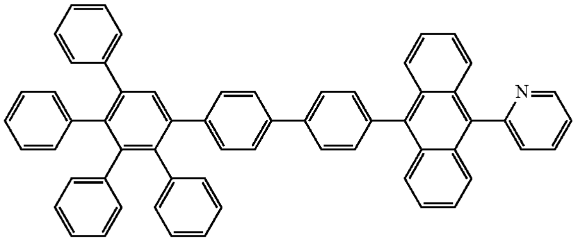
A24
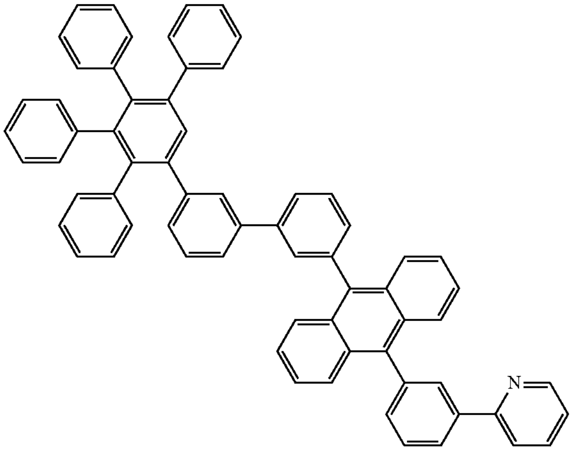

-continued
A25
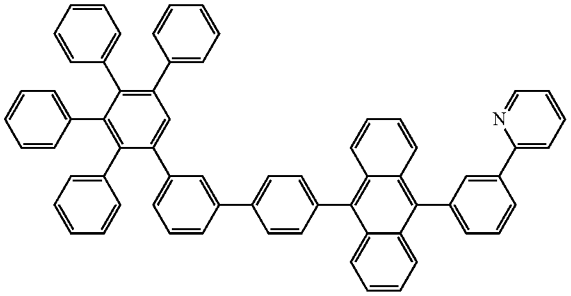
A26
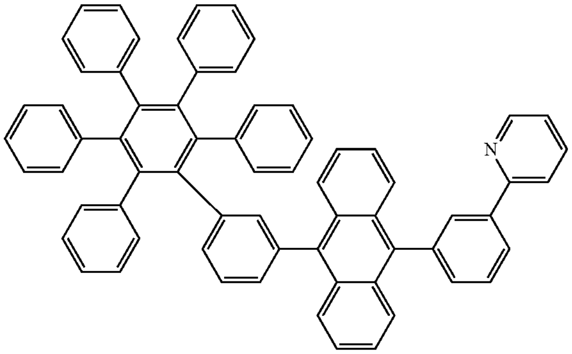
A27
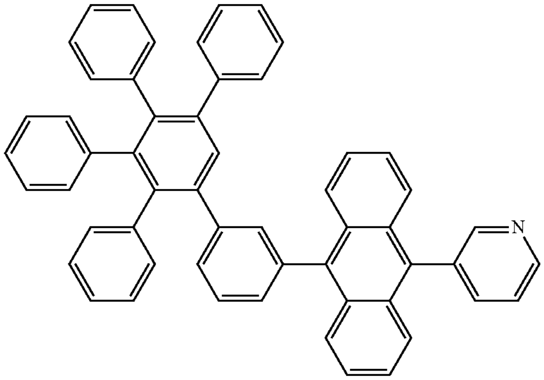
A28
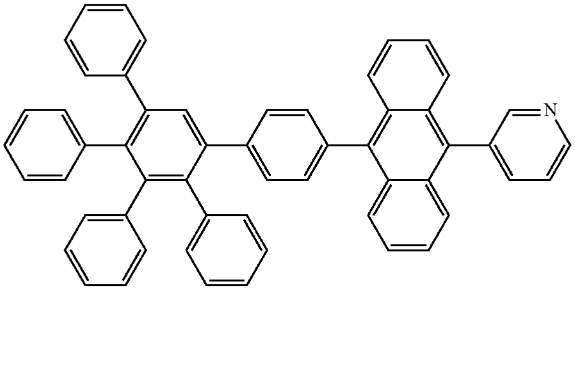
-continued
A29
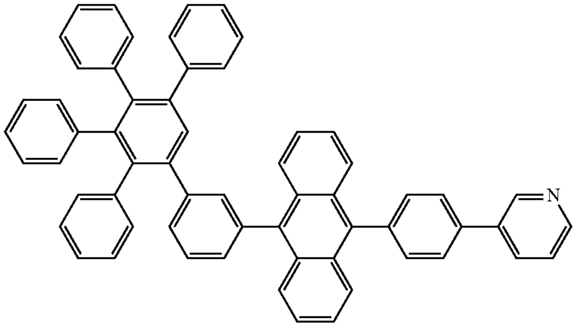
A30
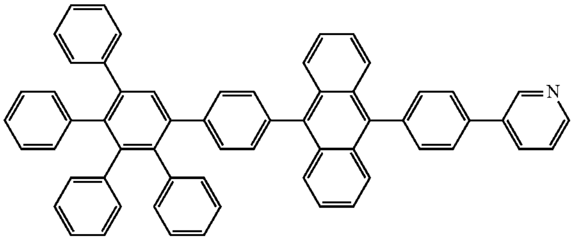
A31
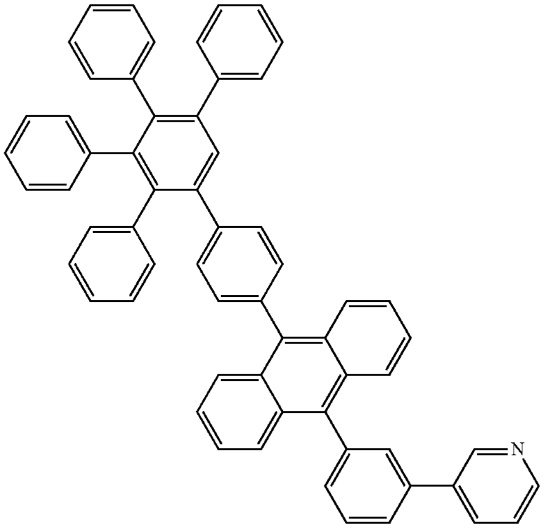

-continued
A32
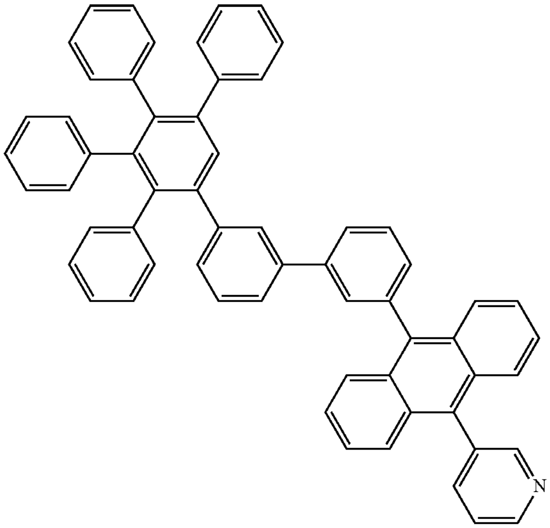
A33
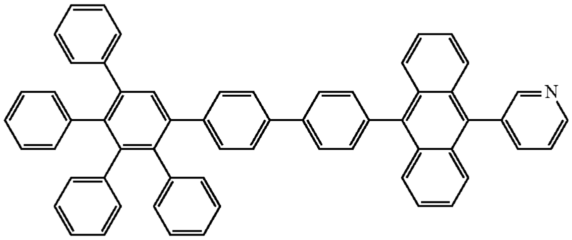
A34
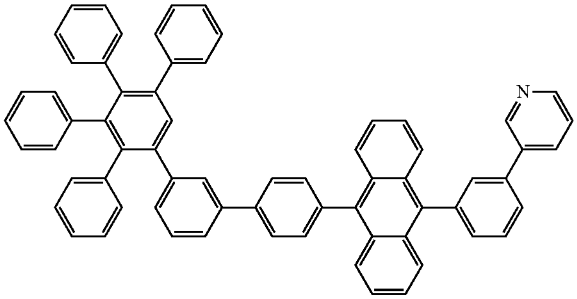
A35
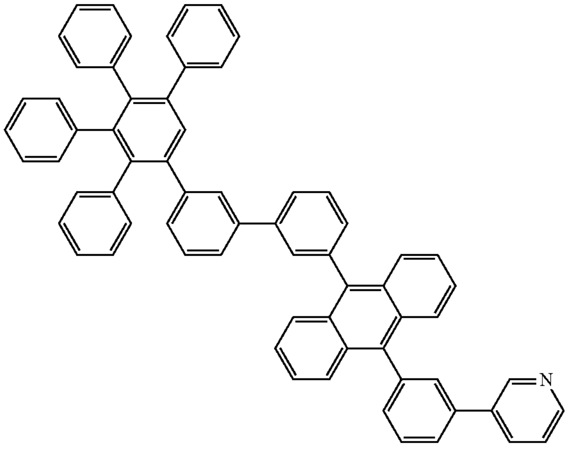
-continued
A36
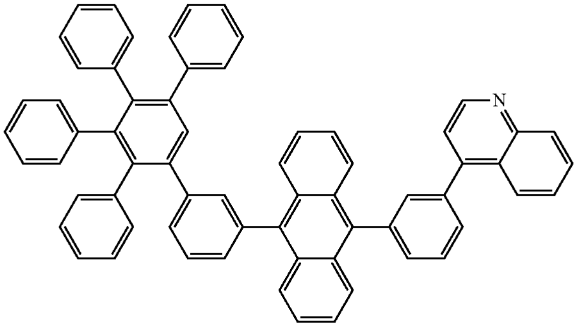
A37
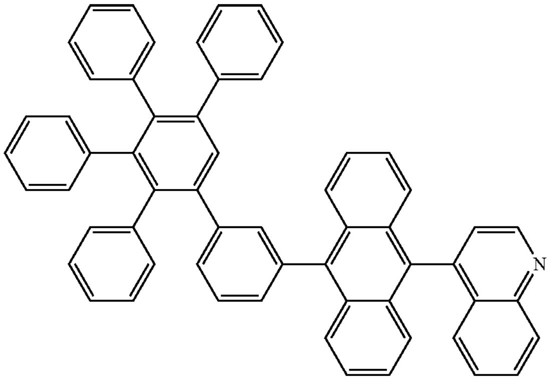
A38
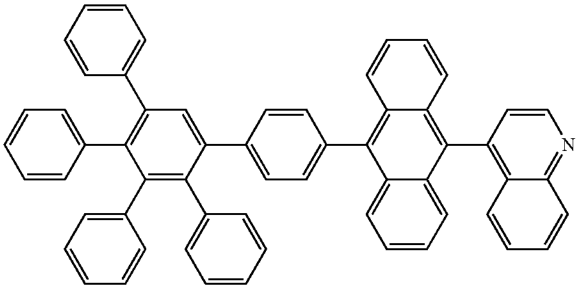
A39
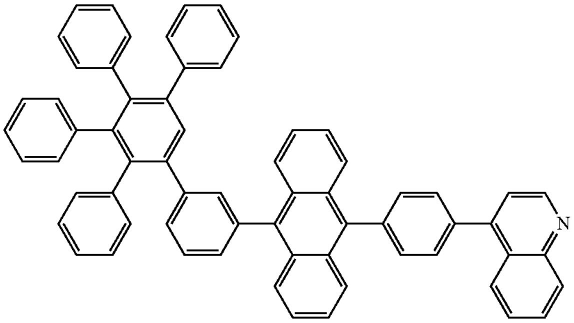

A40
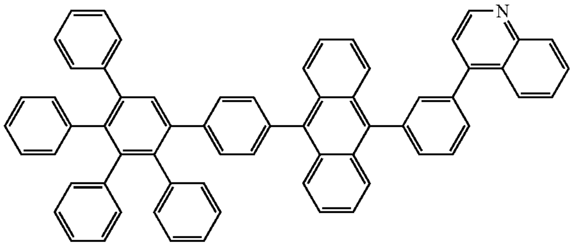
A41
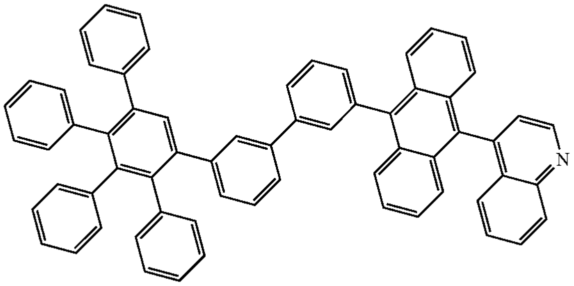
A42
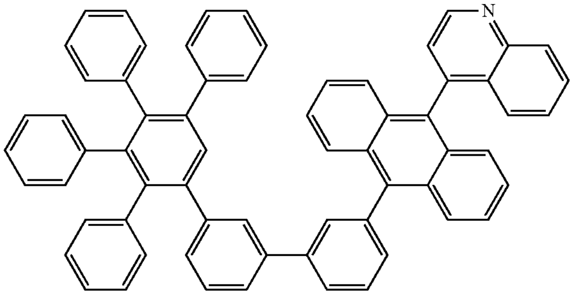
A43
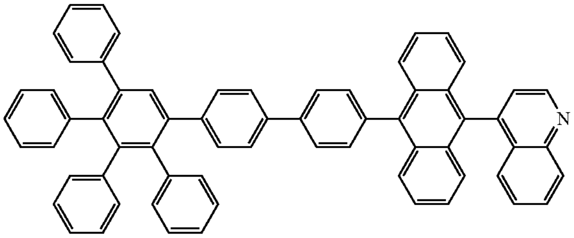
A44
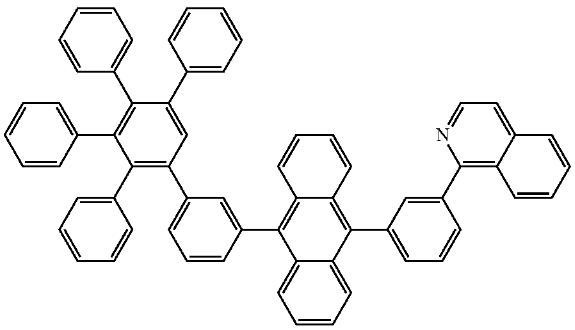
A45
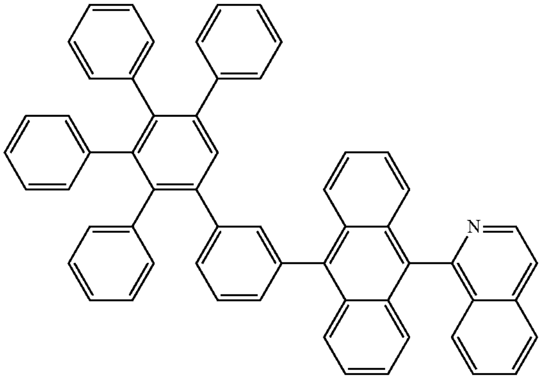
A46
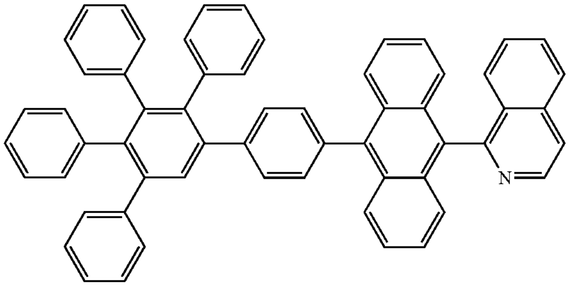
A47
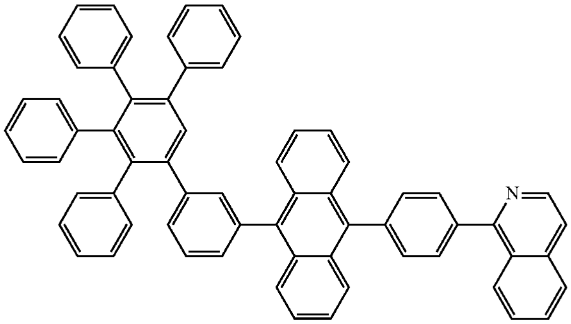
A48
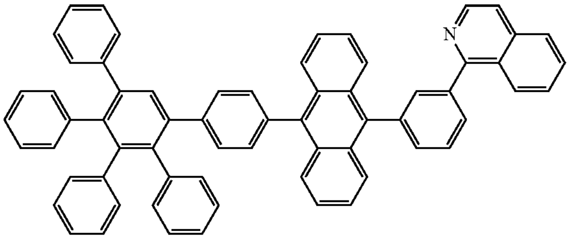

-continued
A49
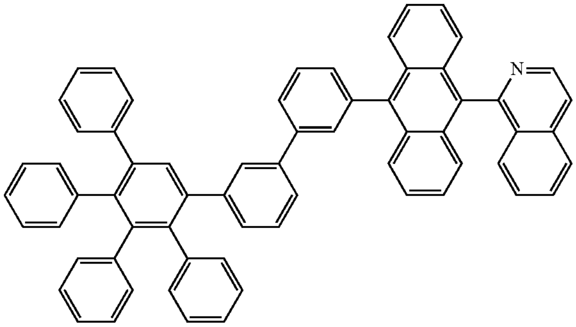
A50
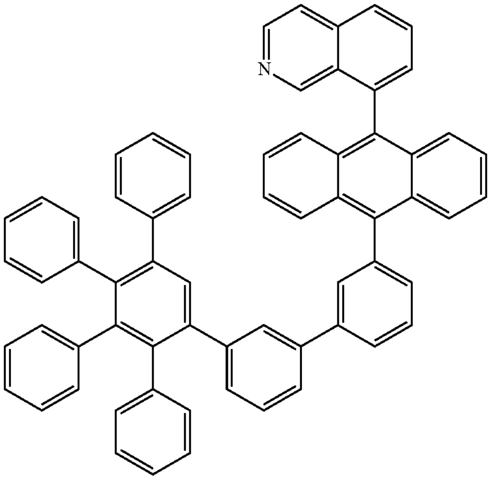
A51
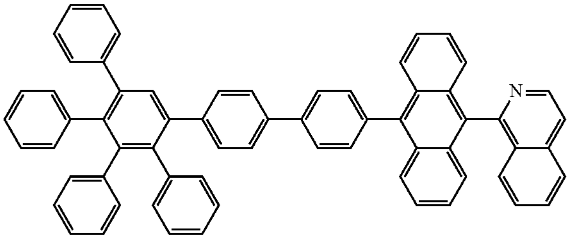
A52
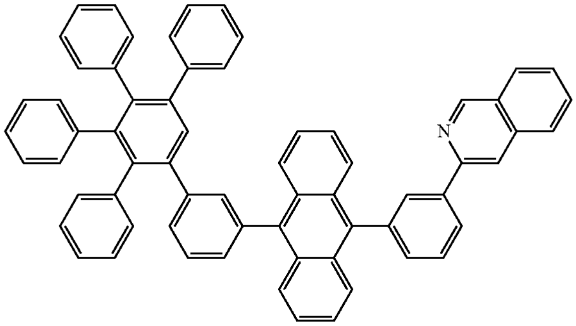
-continued
A53
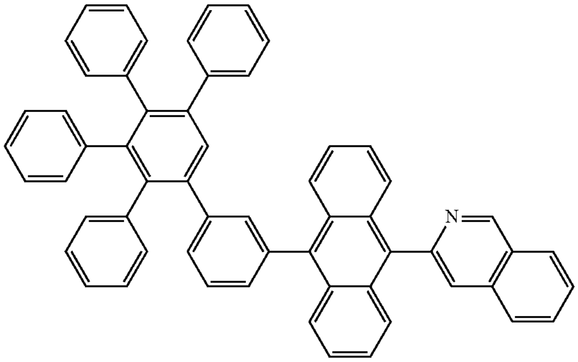
A54
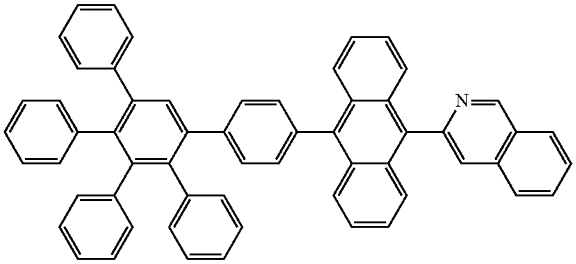
A55
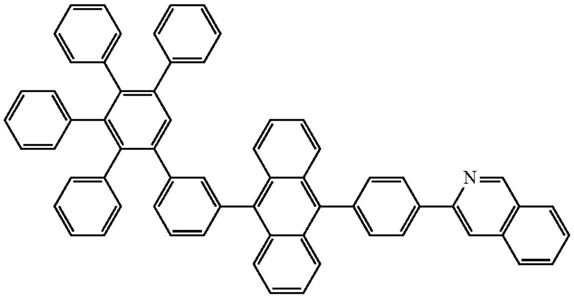
A56
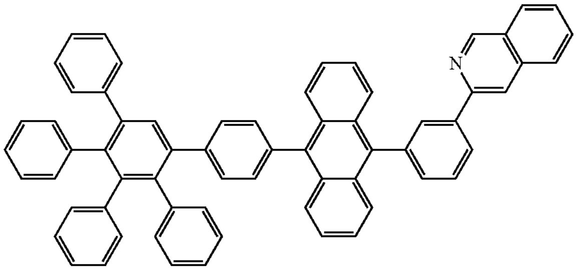
A57
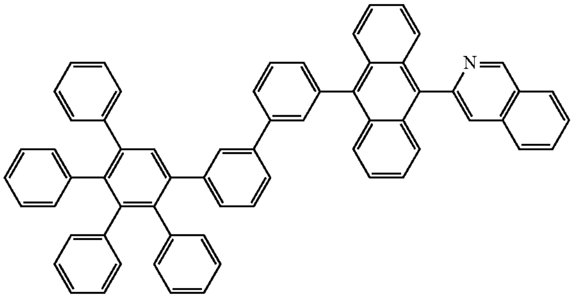

-continued
A58
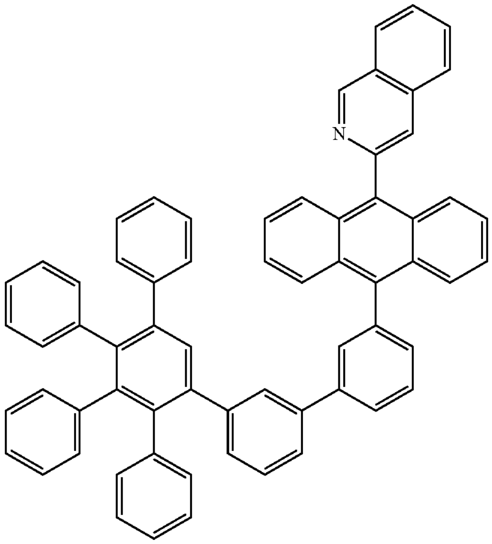
A59
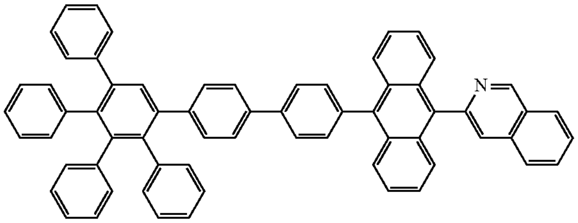
A60
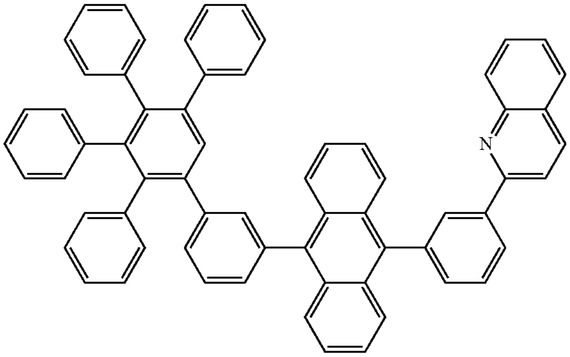
A61
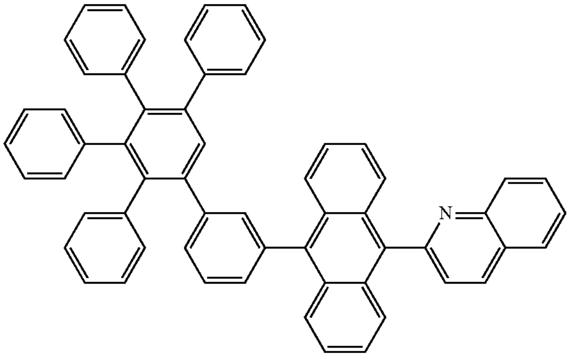
-continued
A62
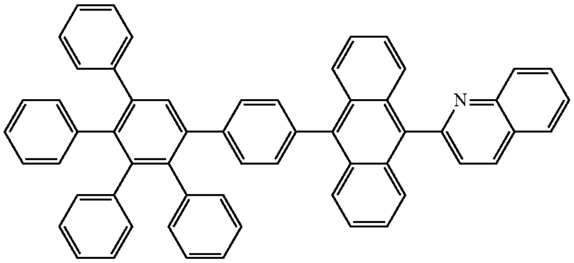
A63
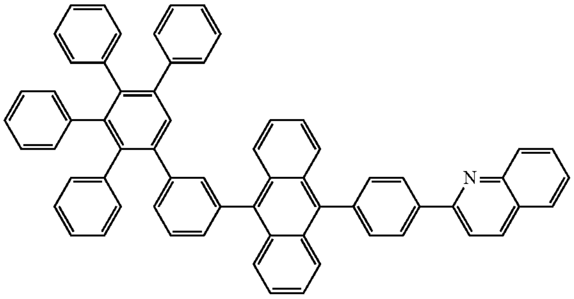
A64
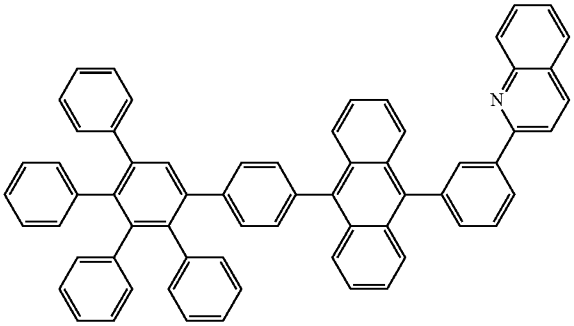
A65
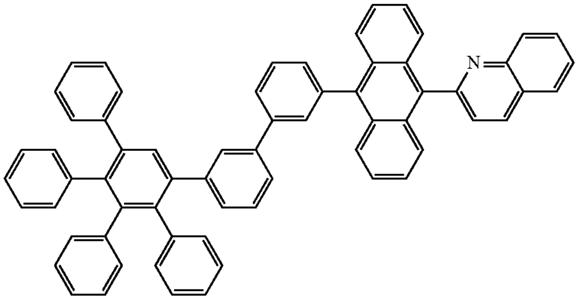

-continued
A66
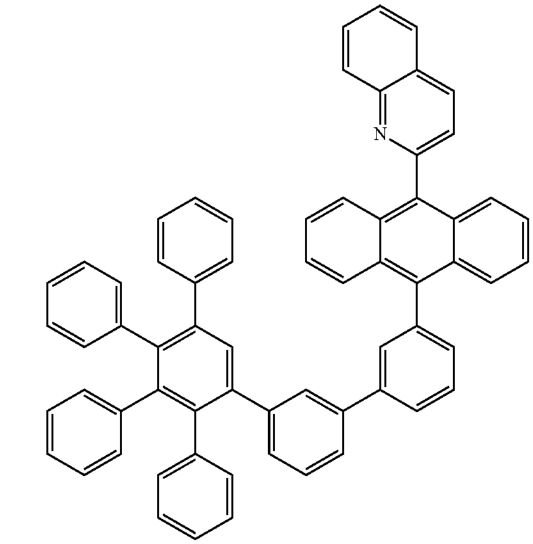
A67
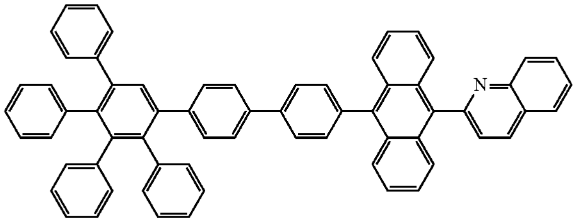
A68
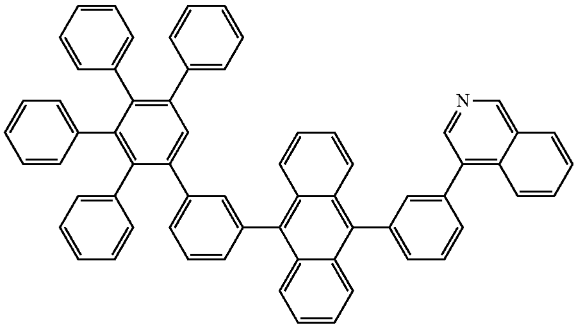
A69
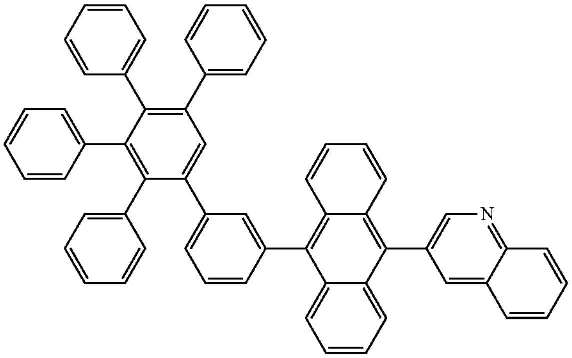
-continued
A70
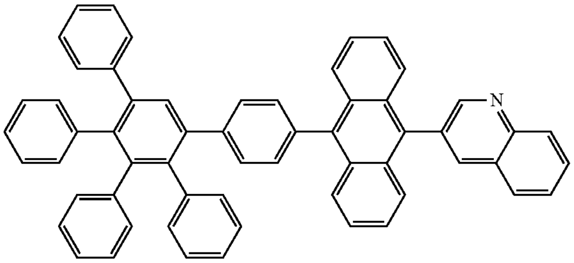
A71
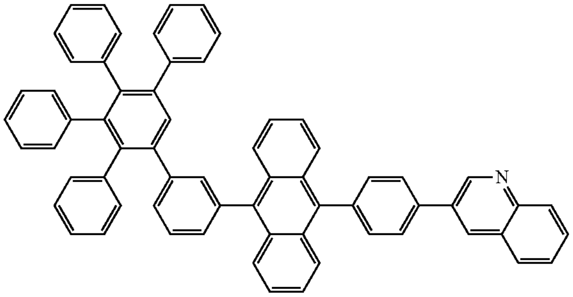
A72
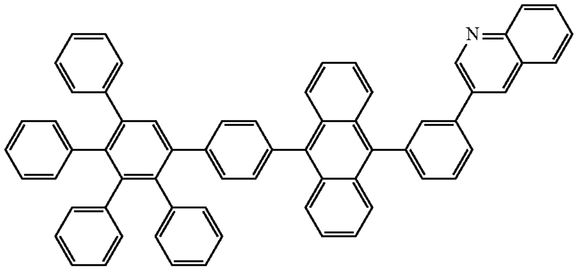
A73
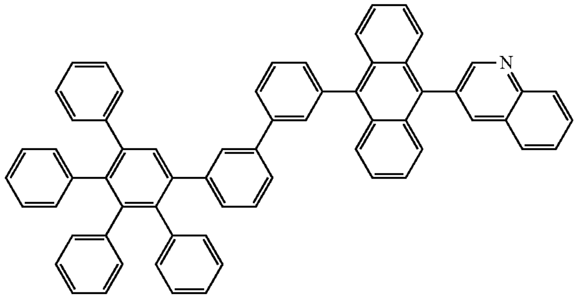

-continued
A74
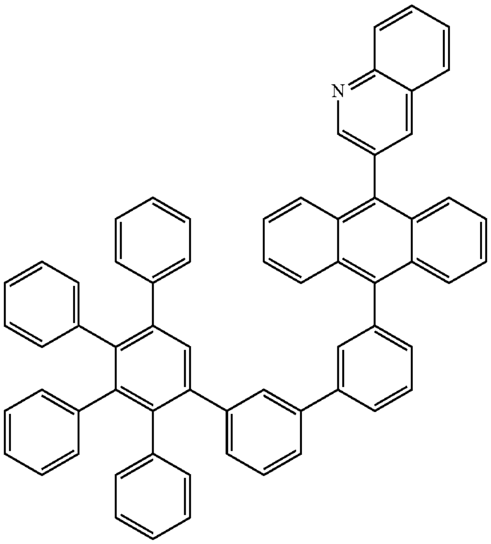
A75
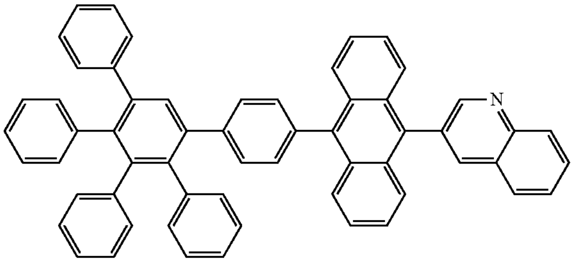
A76
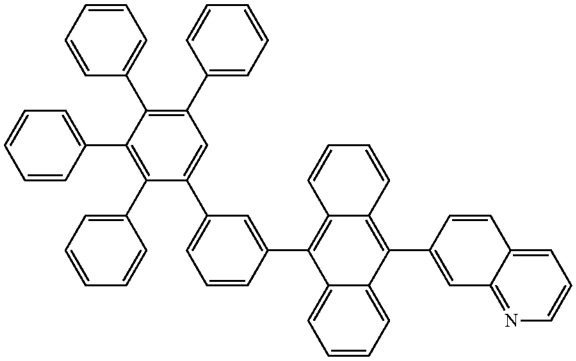
A77
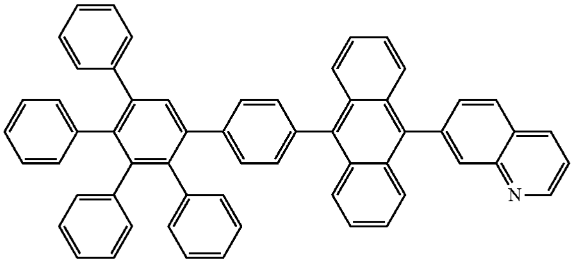
-continued
A78
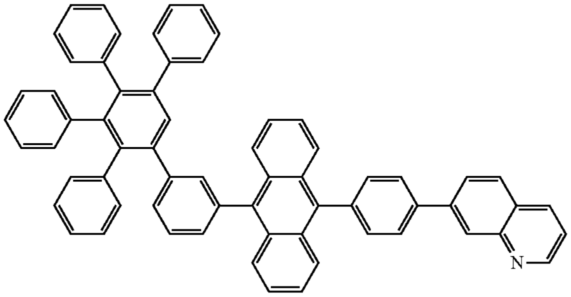
A79
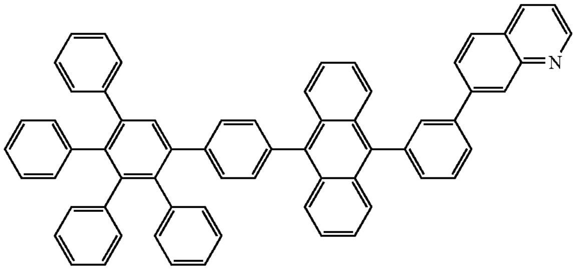
A80
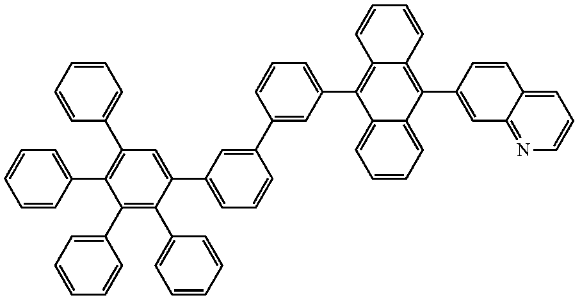
A81
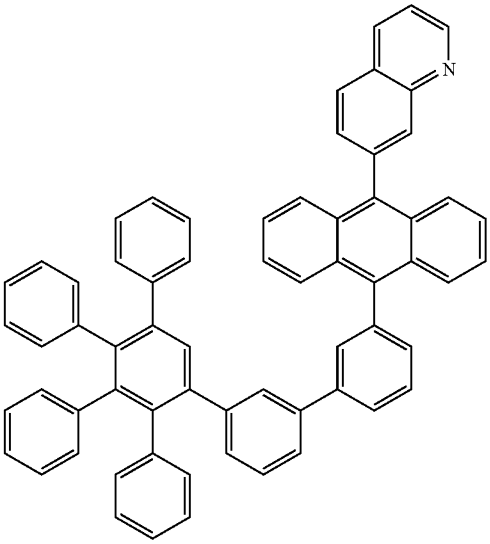

-continued
A82
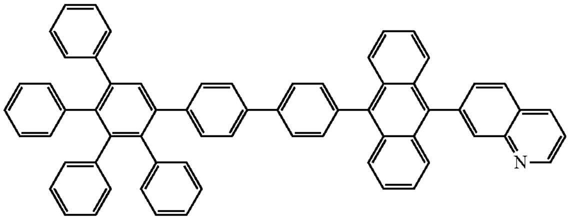
A83
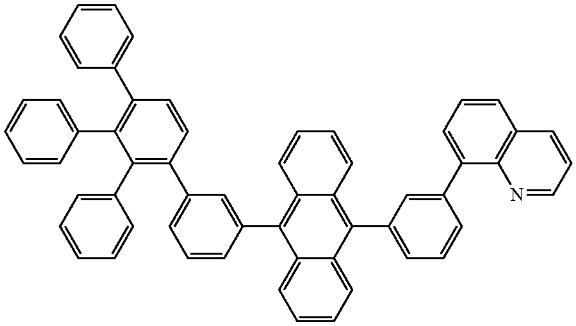
A84
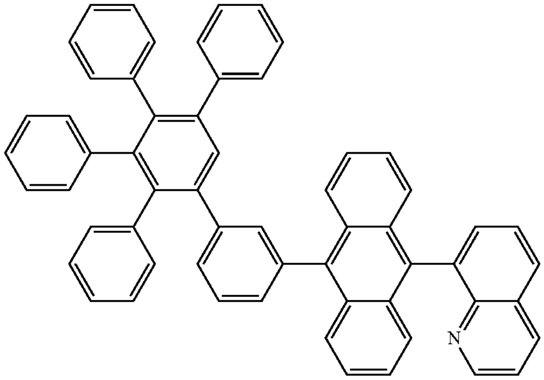
A85
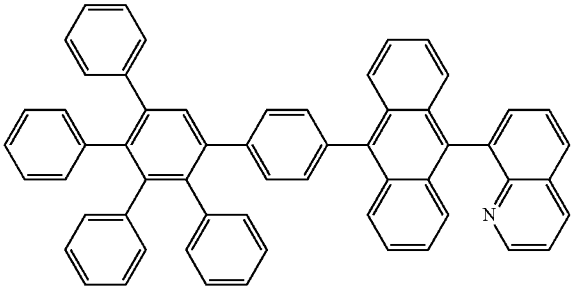
-continued
A86
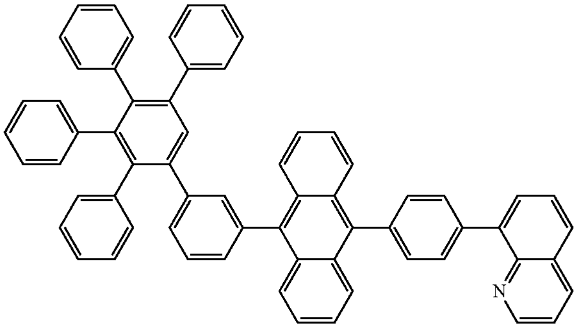
A87
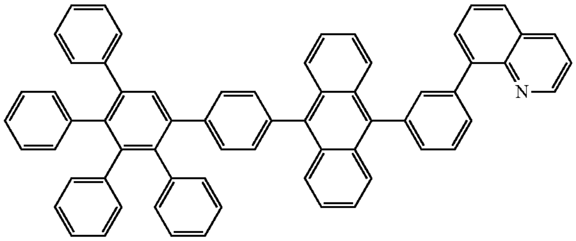
A88
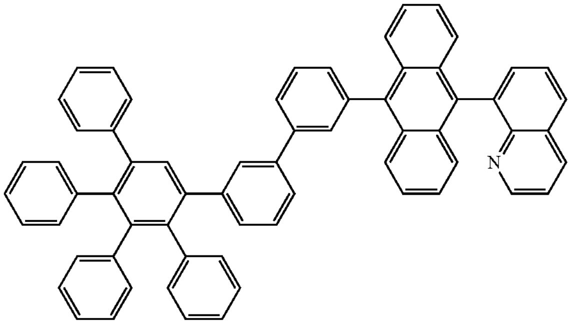
A89
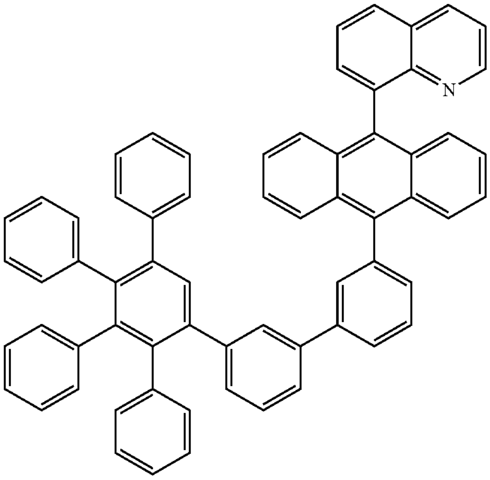

-continued
A90
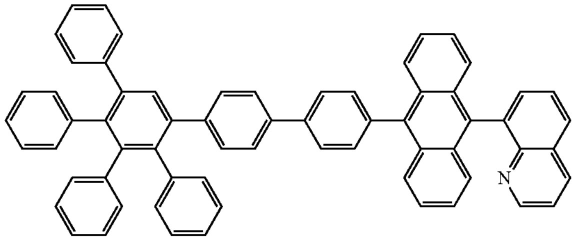
A91
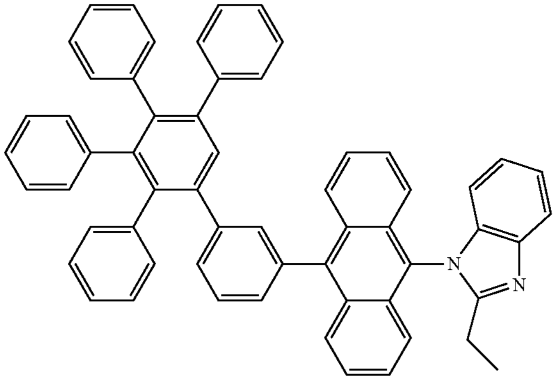
A92
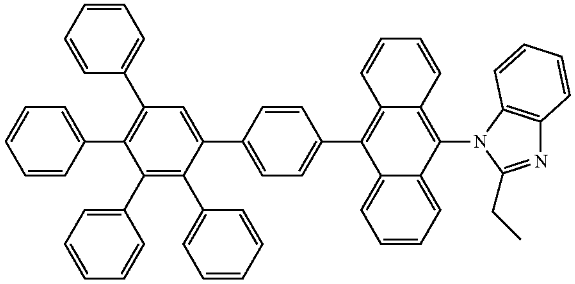
A93
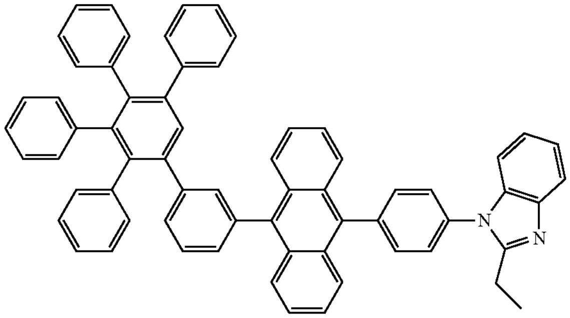
A94
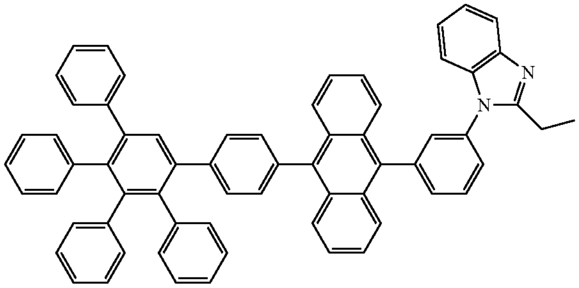
-continued
A95
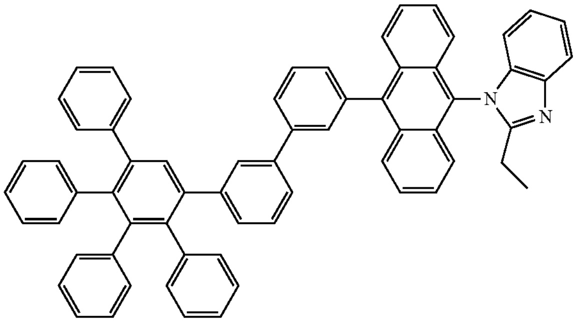
A96
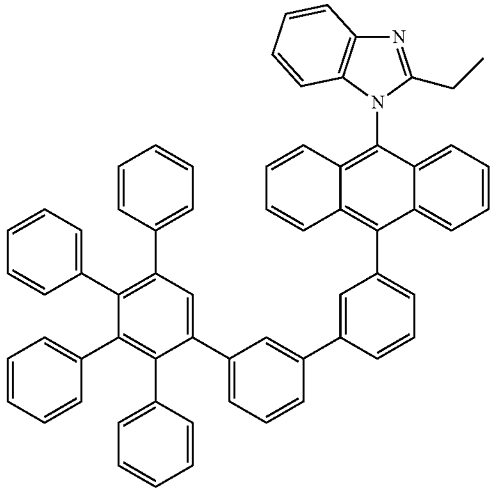
A97
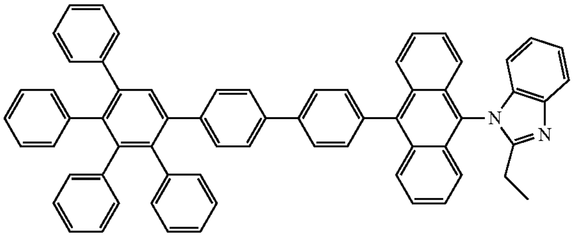
A98
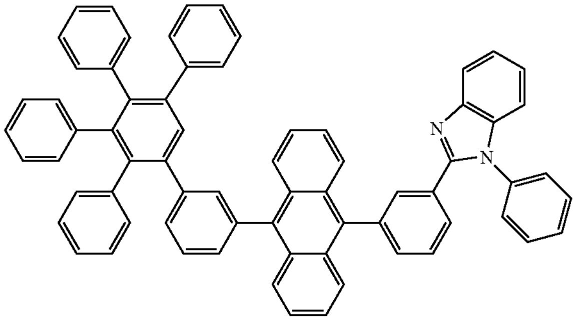

-continued
A99
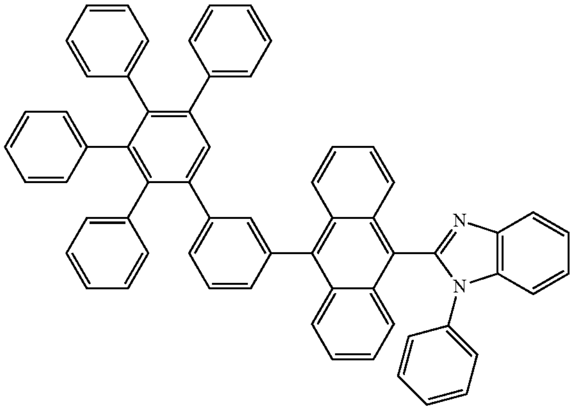
A100
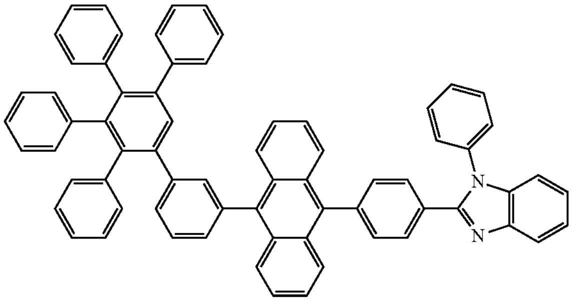
A101
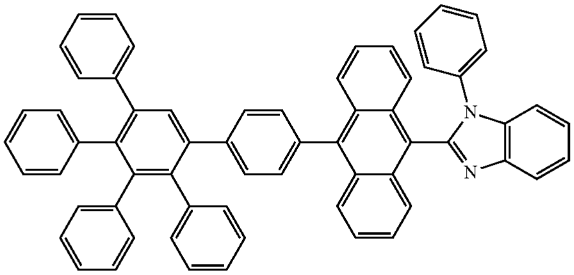
A102
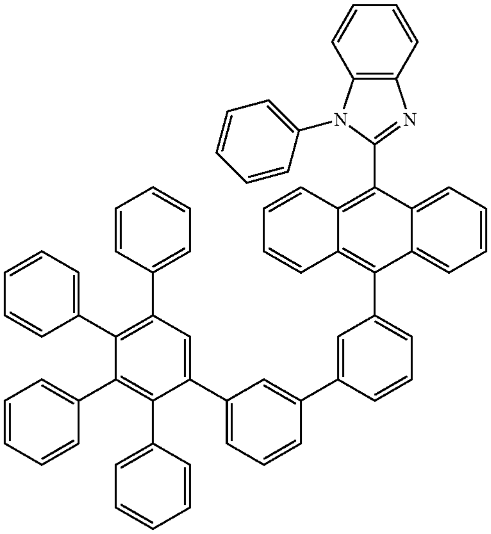
-continued
A103
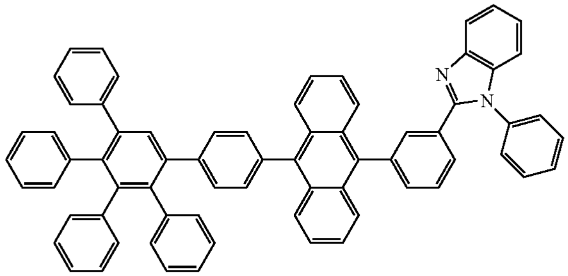
A104
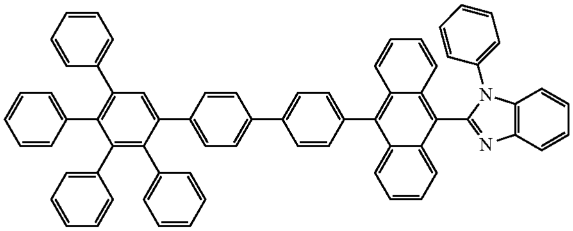
A105
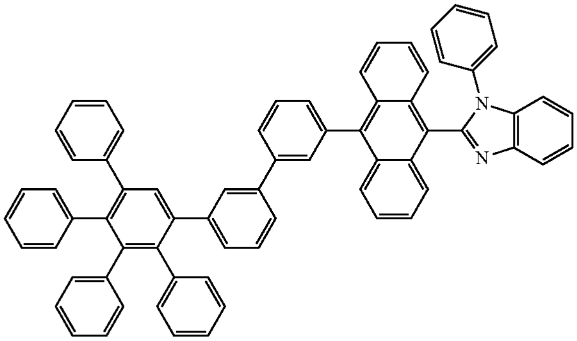
A106
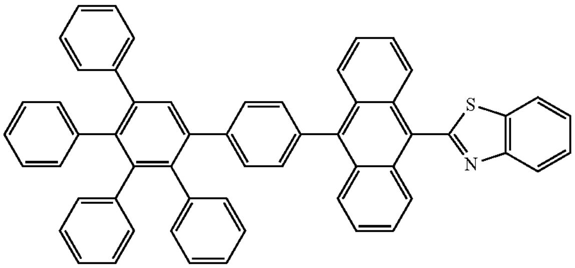
A107
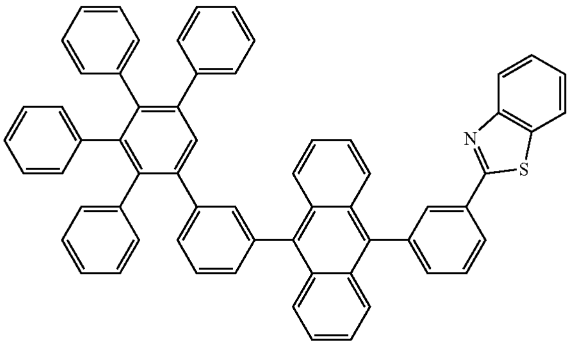

-continued
A108
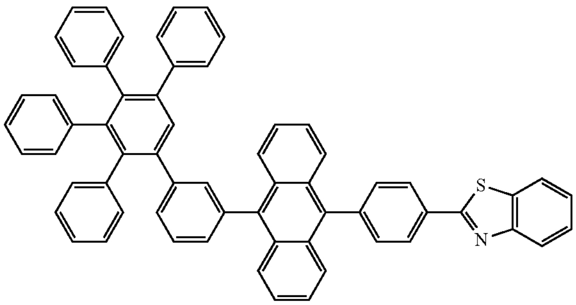
A109
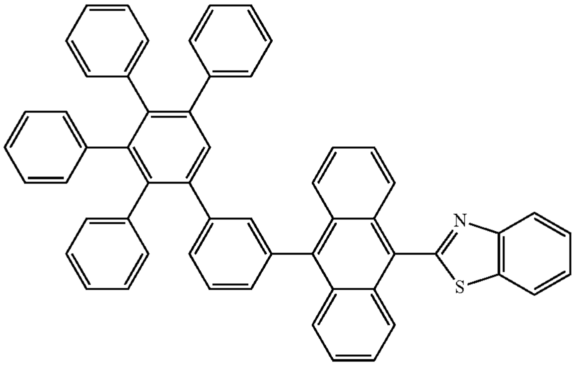
A110
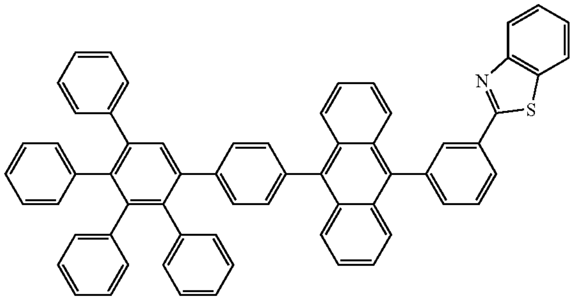
A111
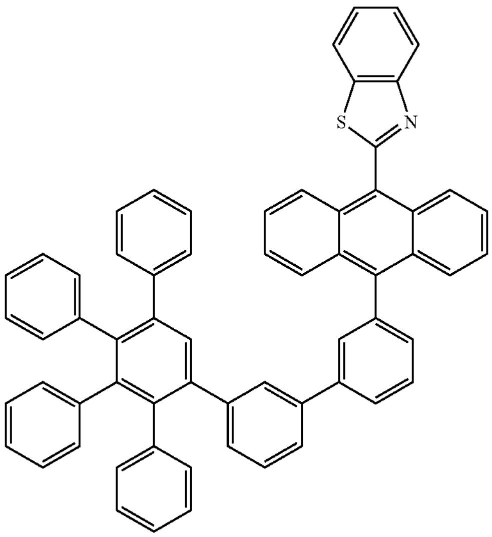
-continued
A112
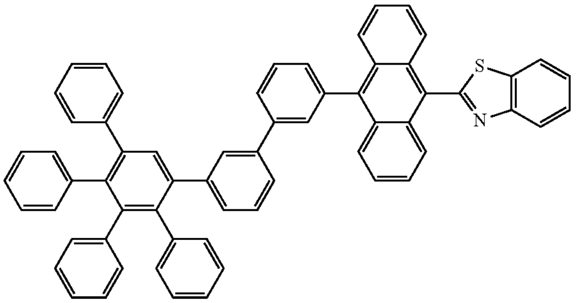
A113
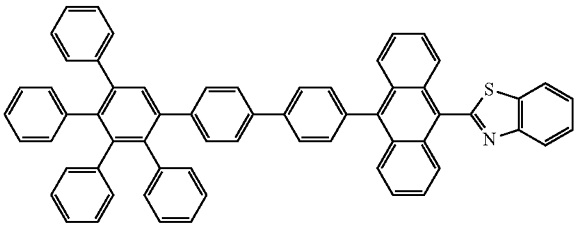
A114
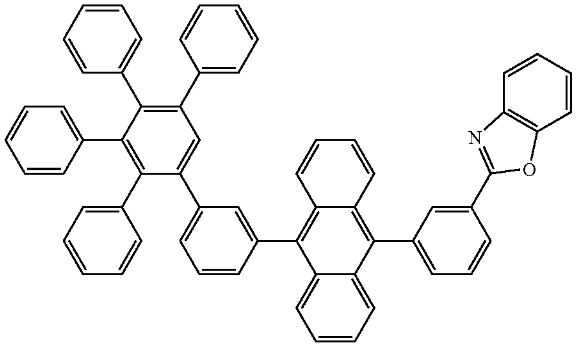
A115
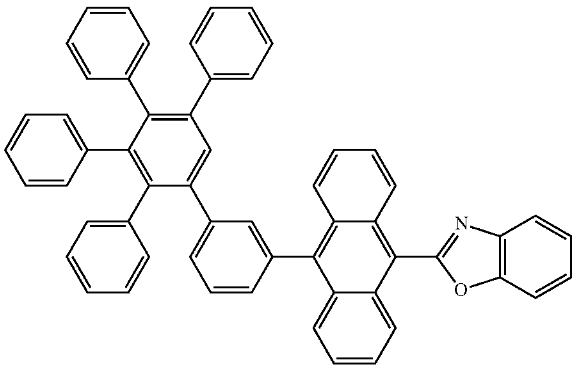
A116
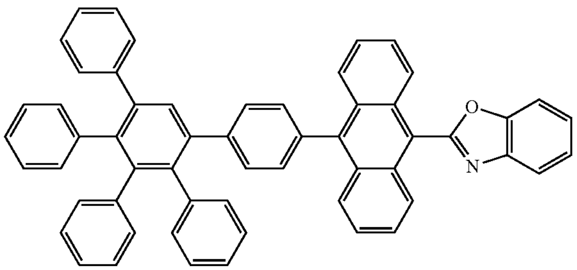

-continued
A117
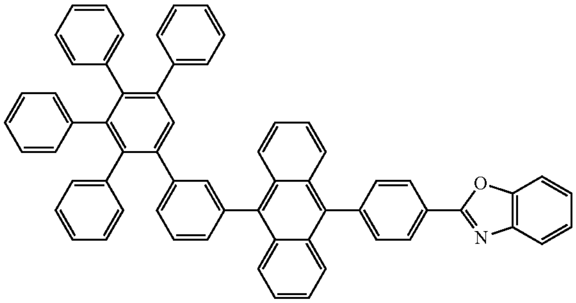
A118
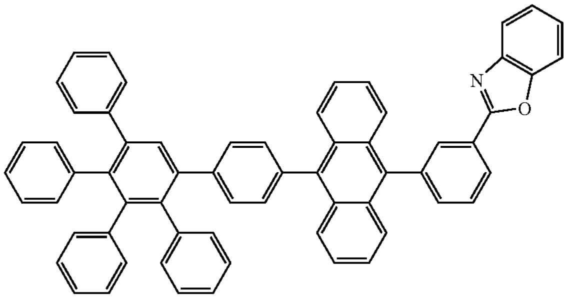
A119
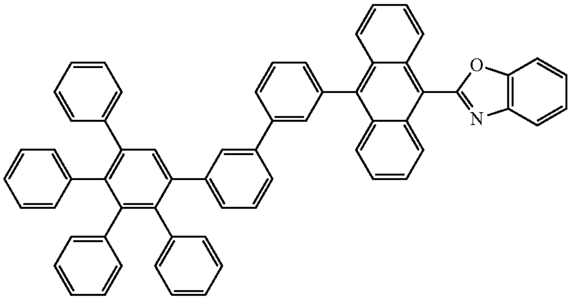
A120
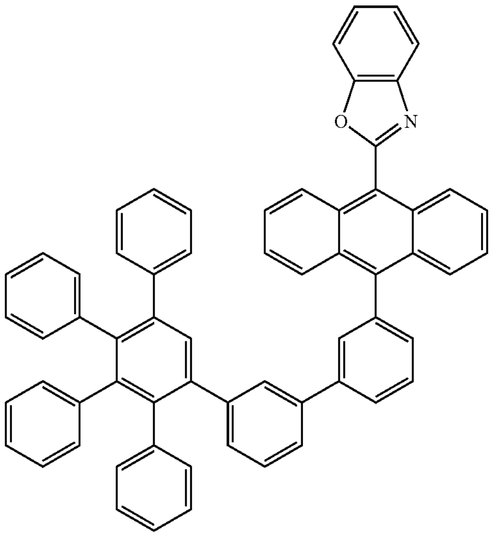
-continued
A121
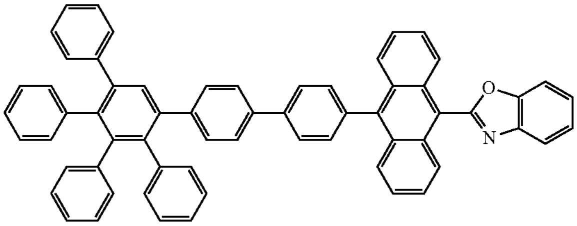
A122
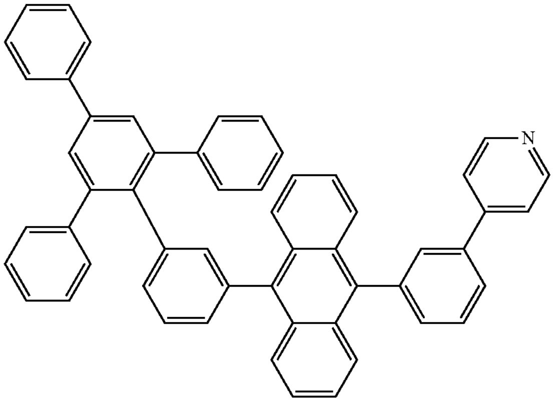
A123
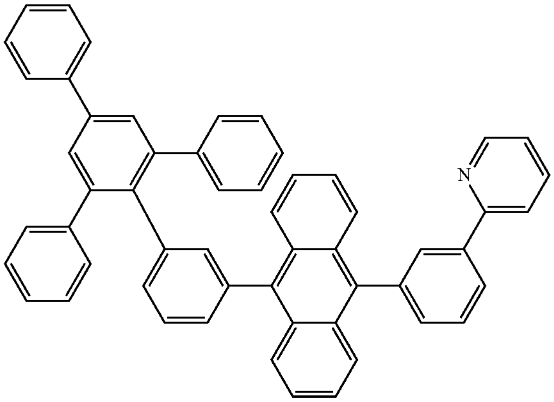
A124
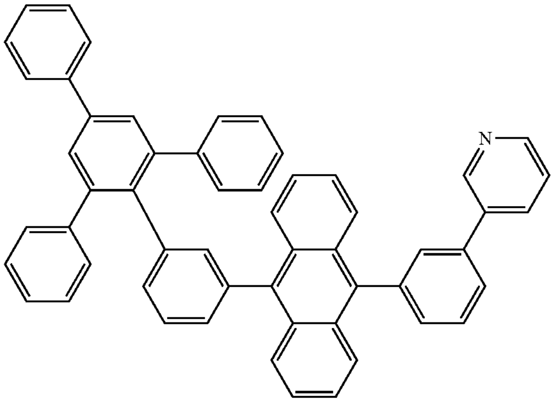

-continued
A125
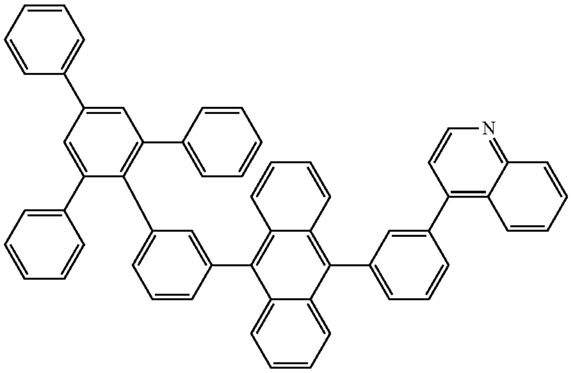
A126
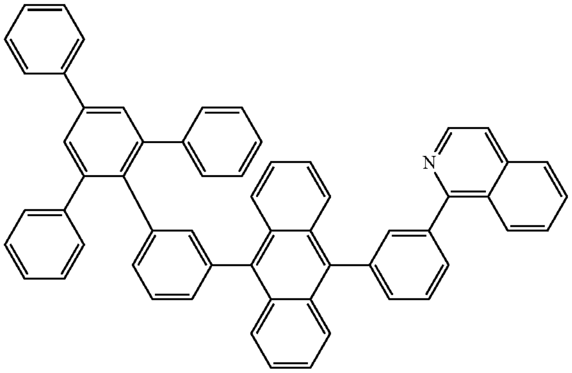
A127
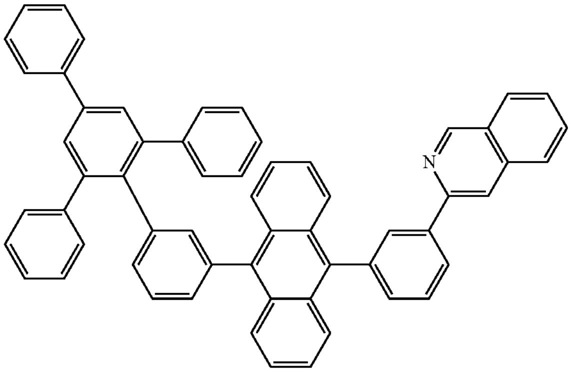
A128
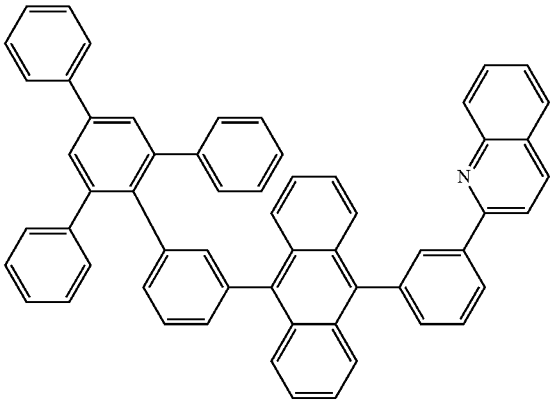
-continued
A129
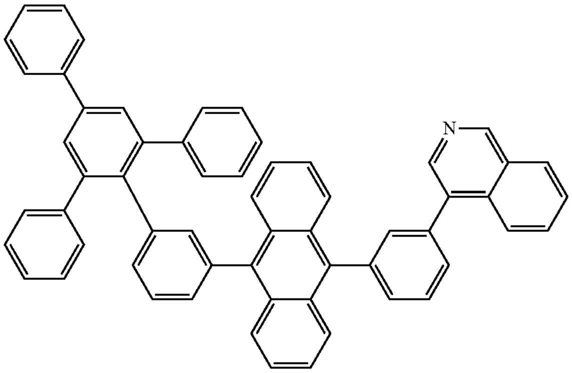
A130
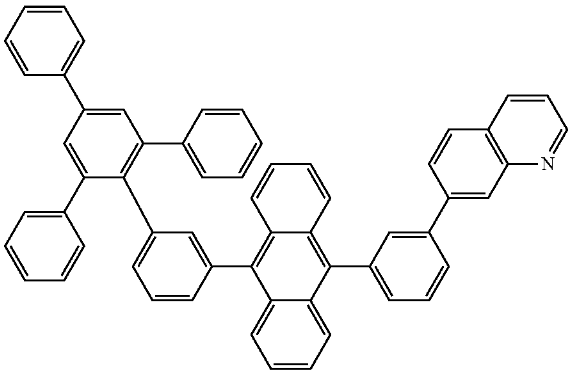
A131
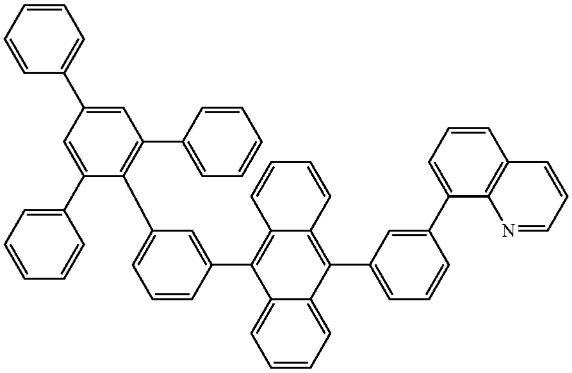
A132
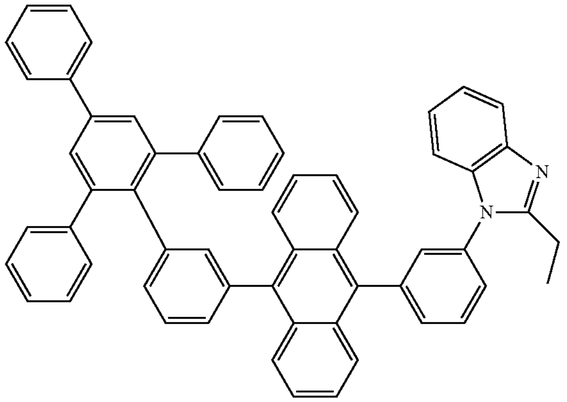

-continued
A133
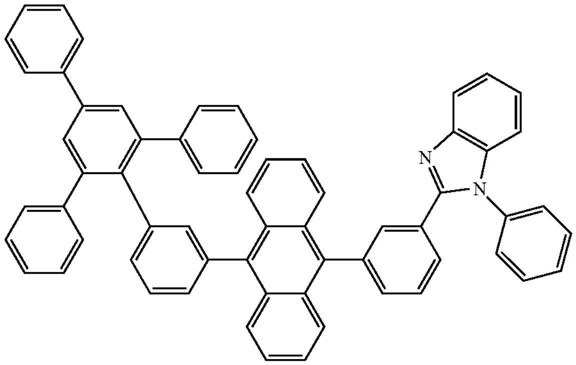
A134
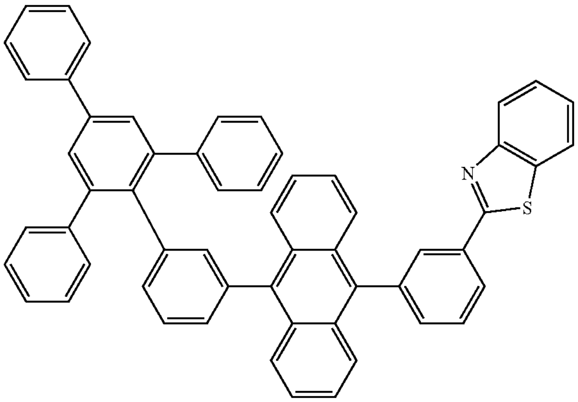
A135
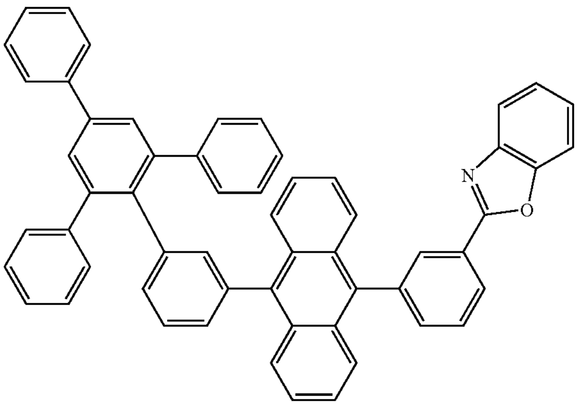
-continued
A136
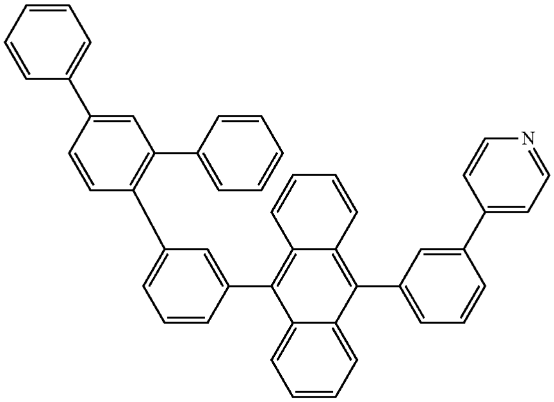
A137
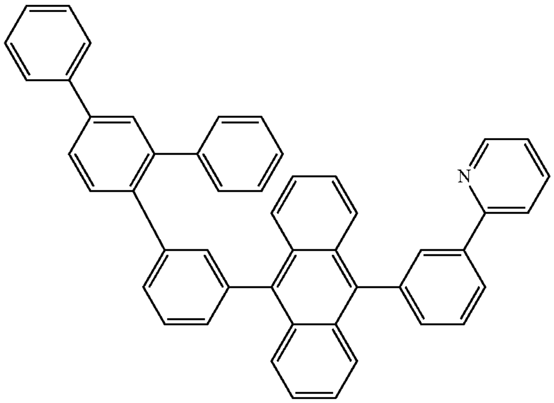
A138
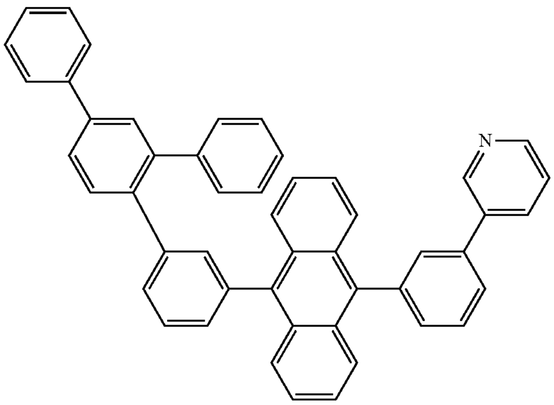

-continued
A139
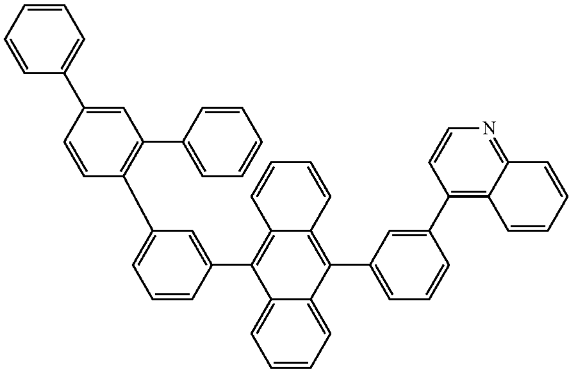
A140
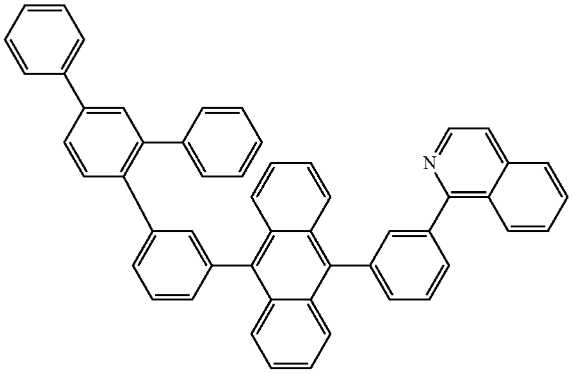
A141
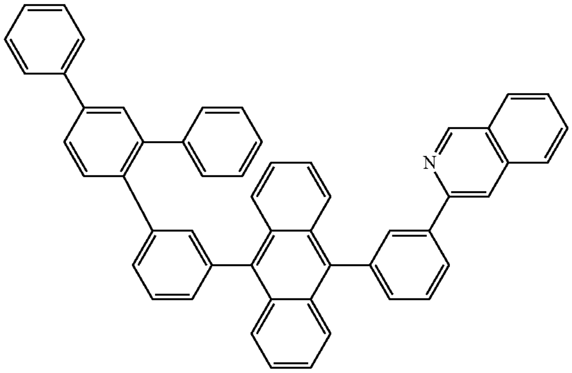
A142
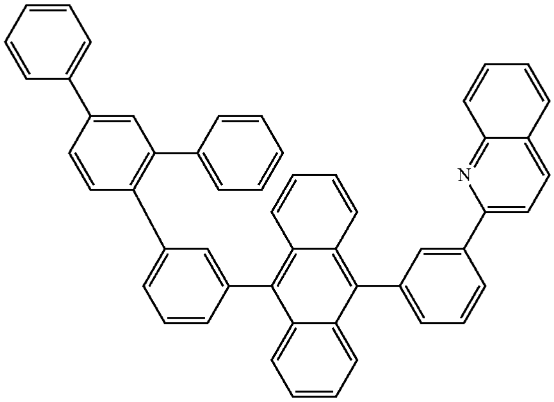
-continued
A143
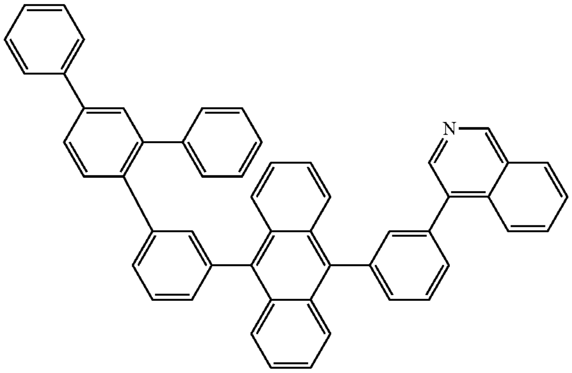
A144
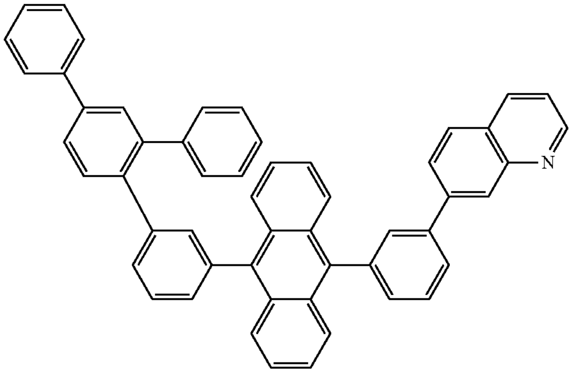
A145
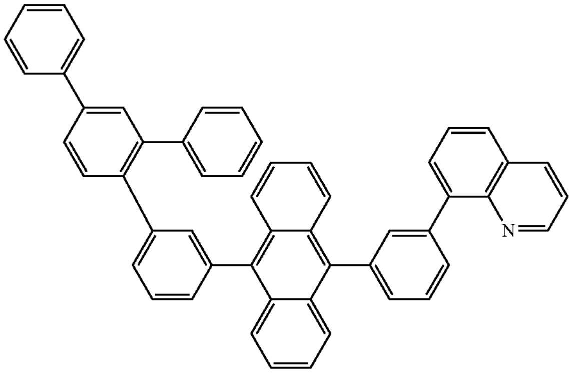
A146
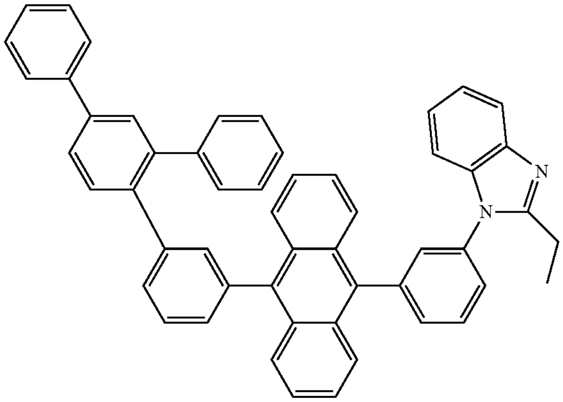

-continued
A147
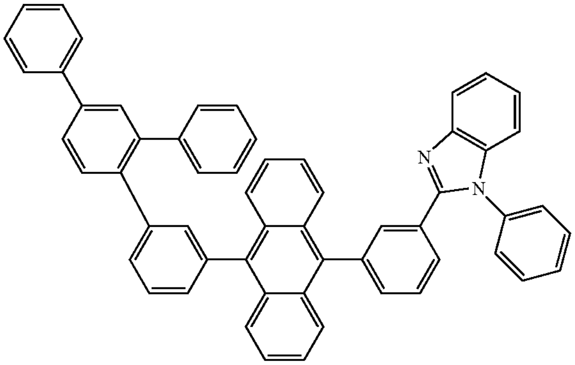
A148
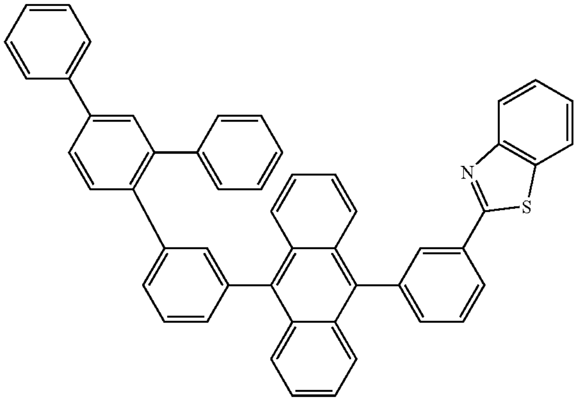
A149
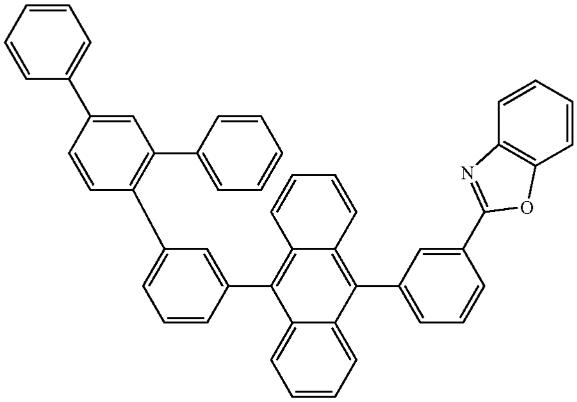
A150
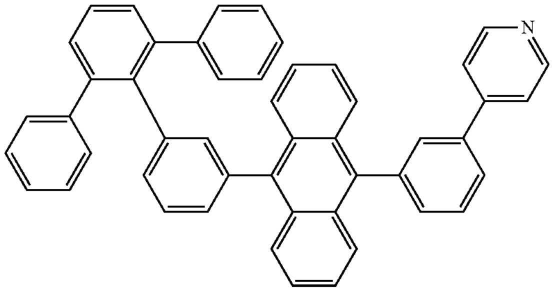
-continued
A151
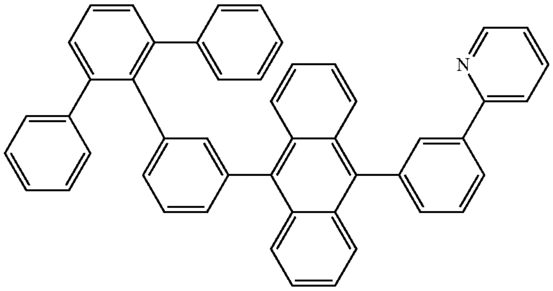
A152
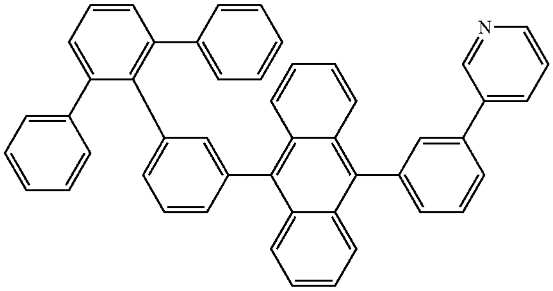
A153
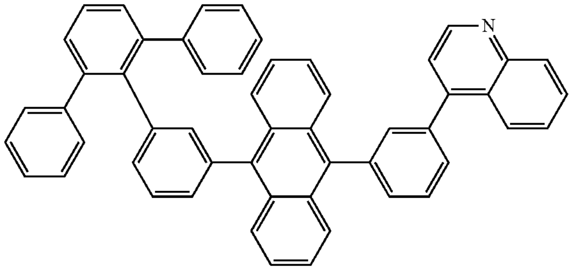
A154
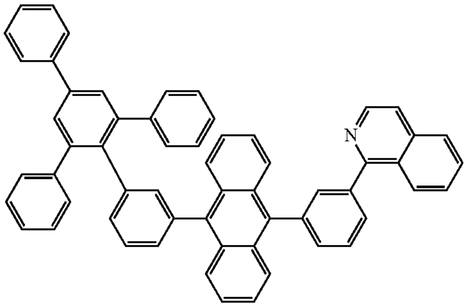
A155
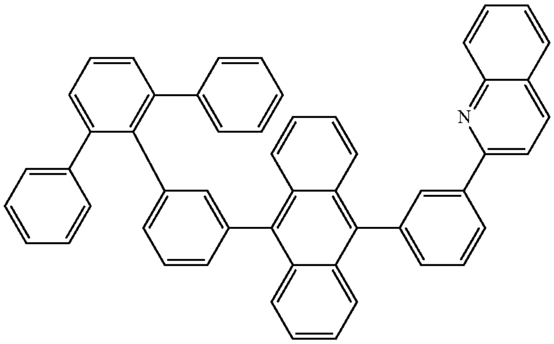

-continued
A156
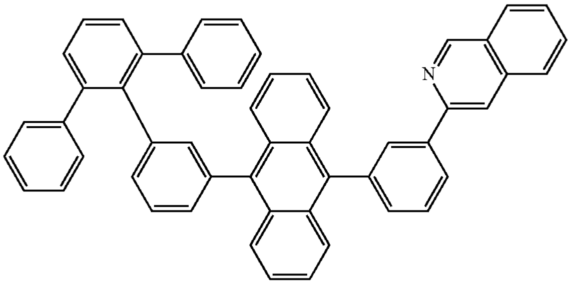
A157
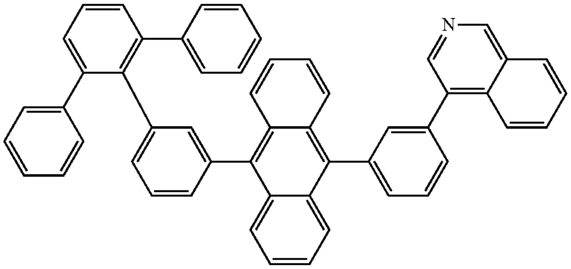
A158
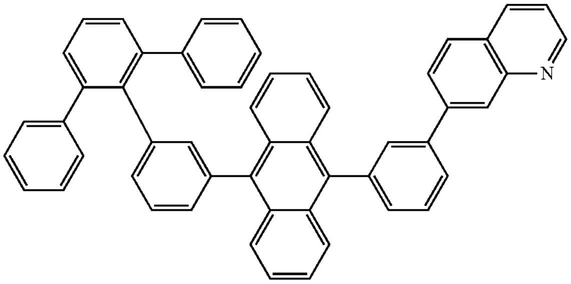
A159
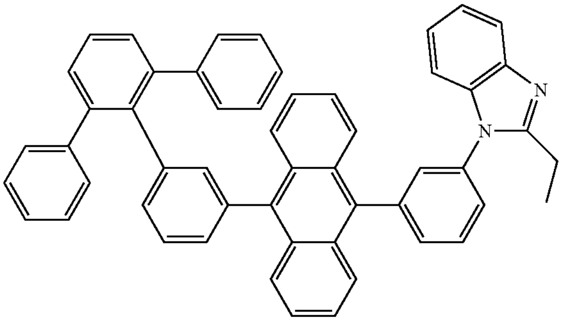
A160
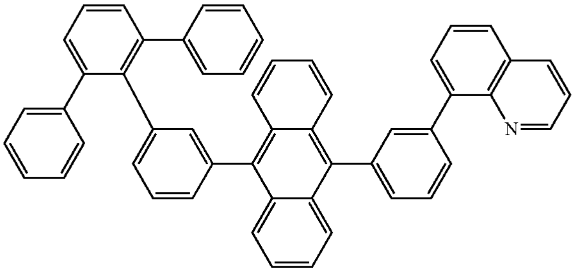
-continued
A161
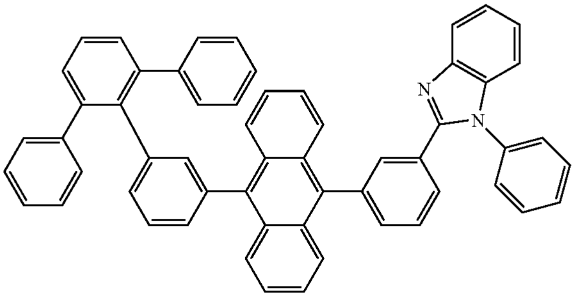
A162
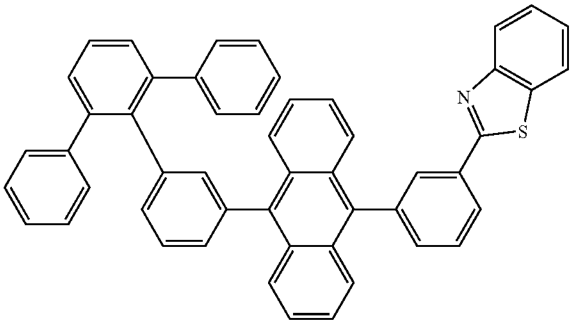
A163
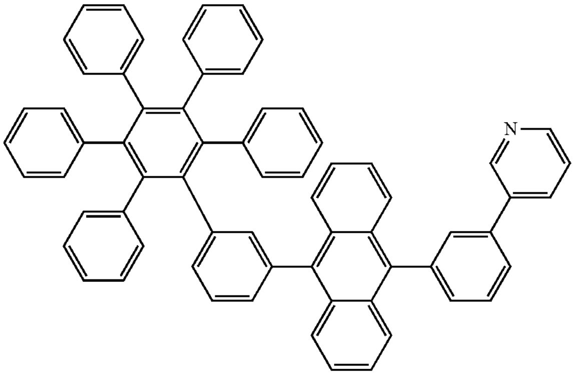
A164
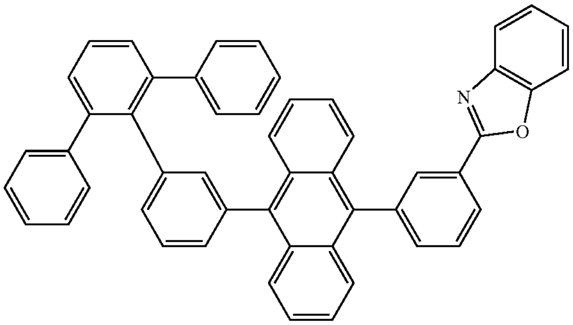

-continued
A165
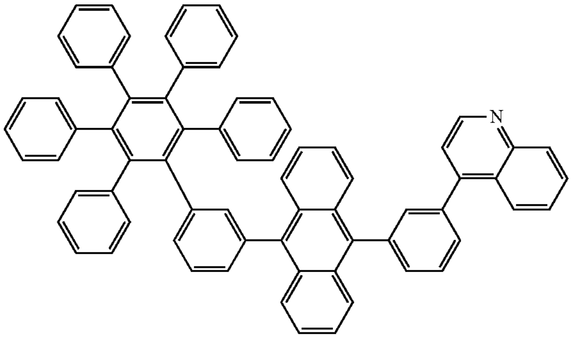
A166
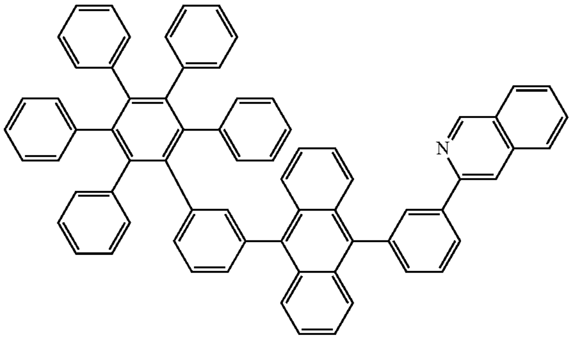
A167
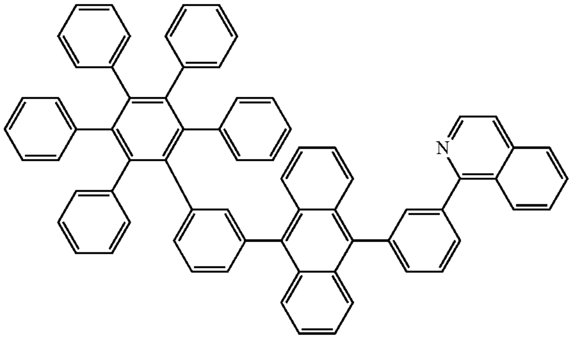
A168
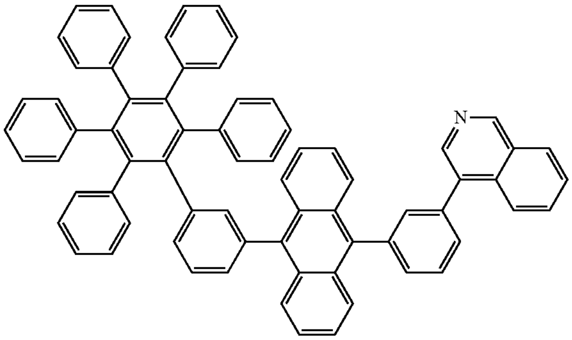
-continued
A169
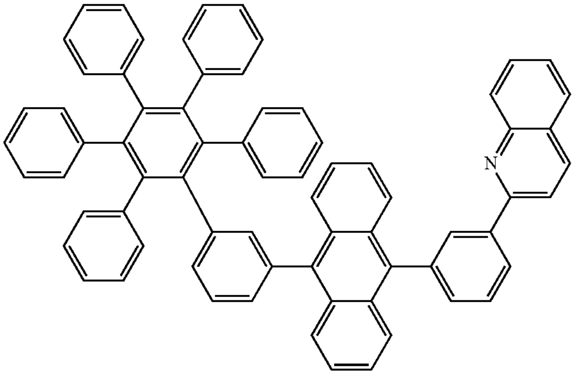
A170
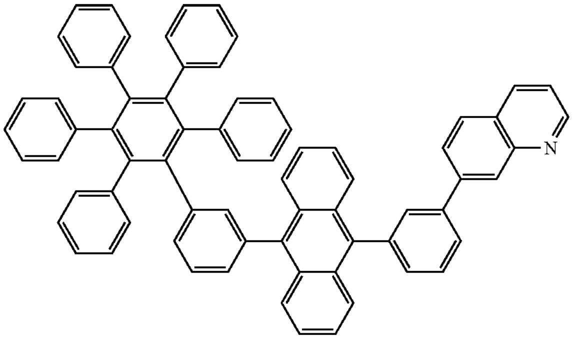
A171
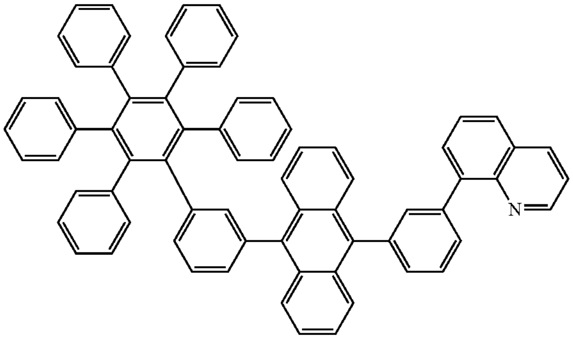
A172
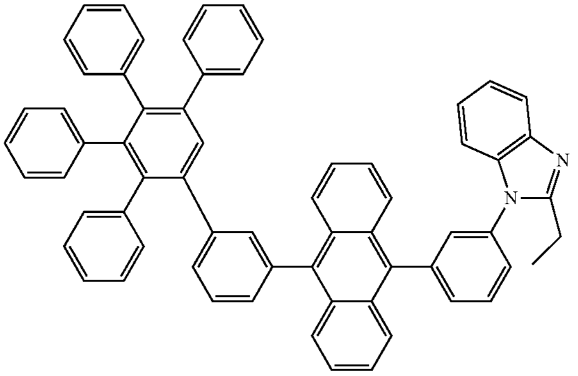

-continued
A173
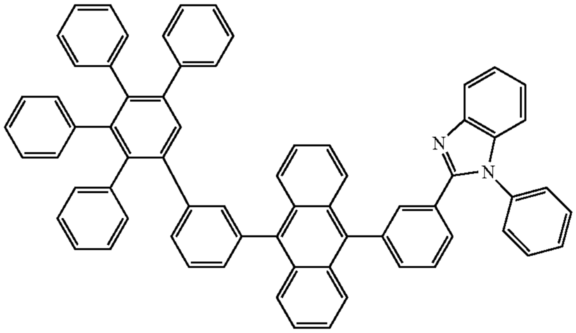
A174
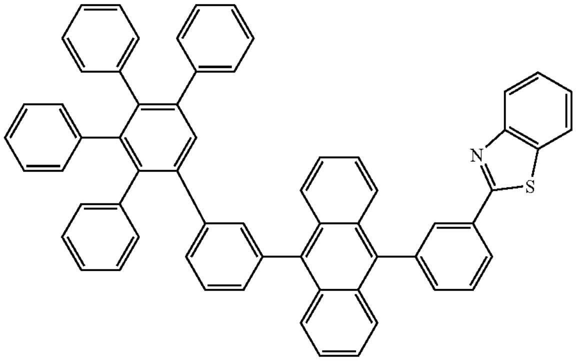
A175
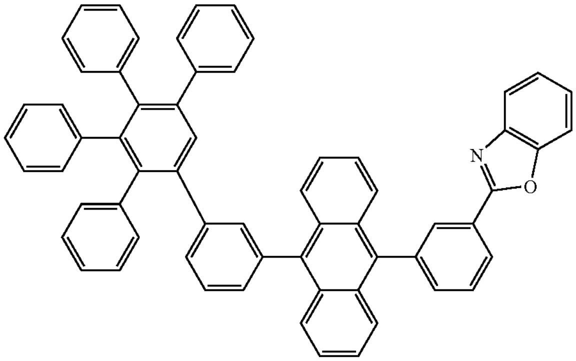
A176
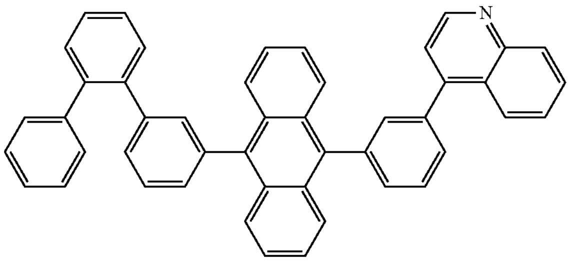
-continued
A177
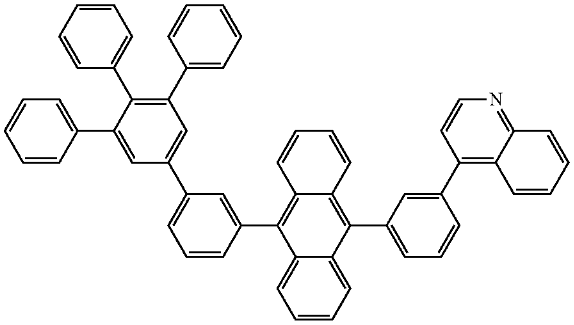
A178
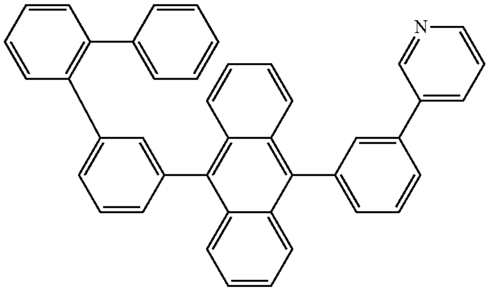
A179
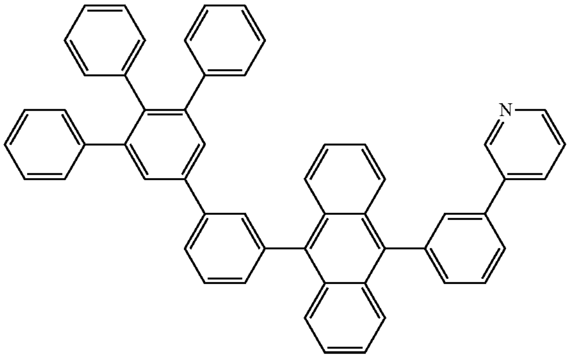
A180
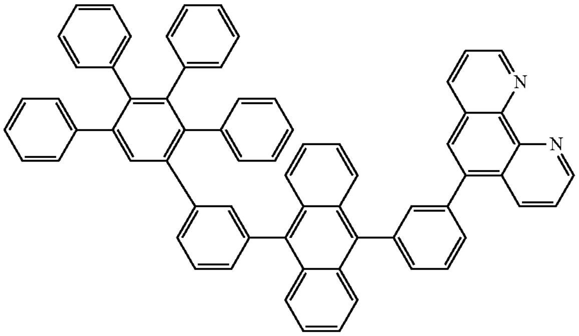

-continued
A181
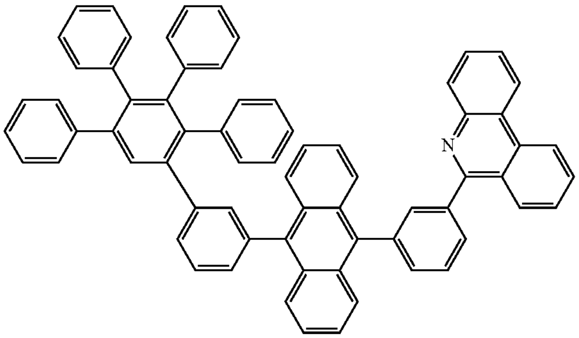
A182
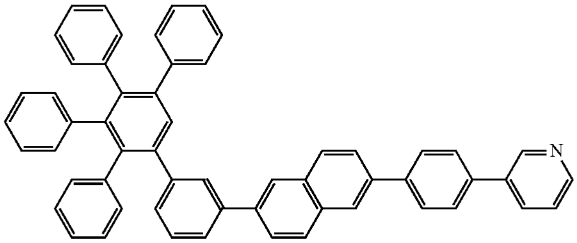
A183
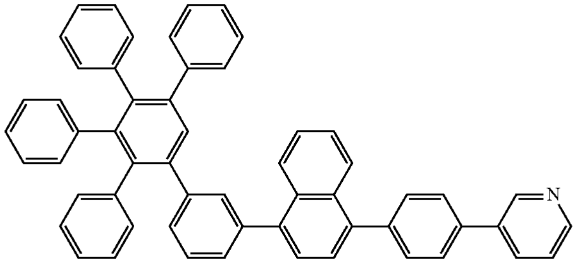
A184
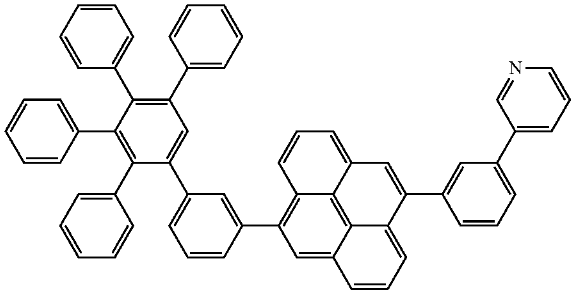
A185
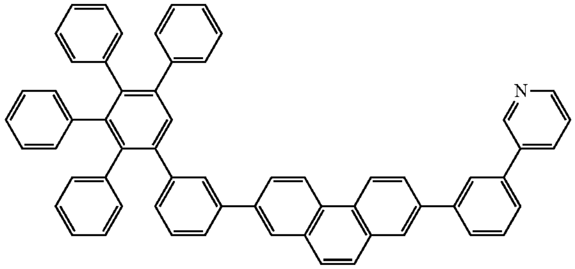
-continued
A186
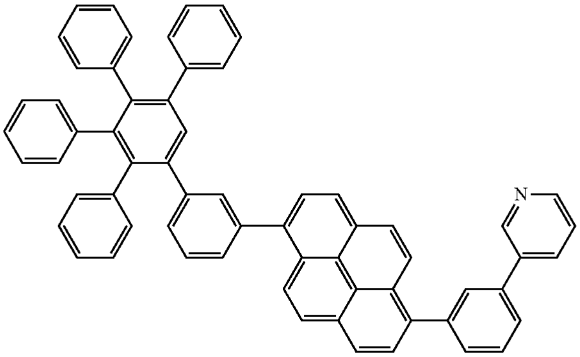
A187
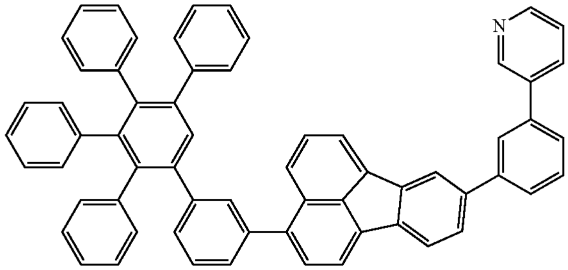
A188
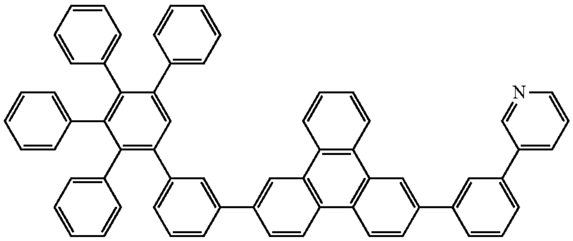
A189
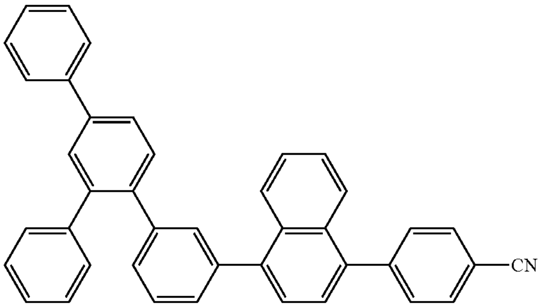
A190
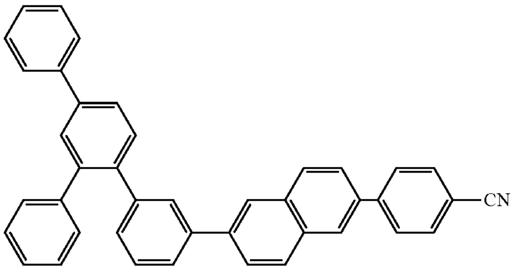

-continued

A191

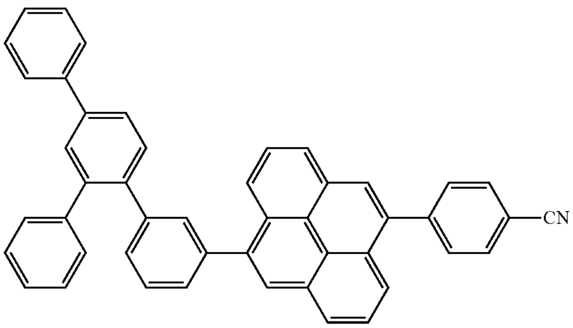

A192

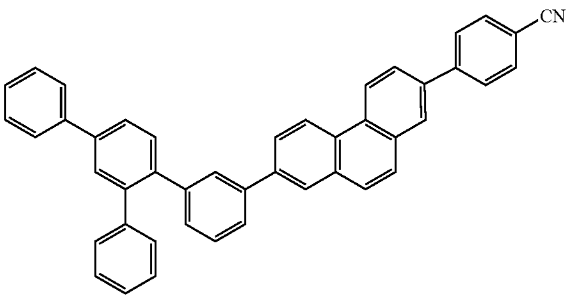

A193

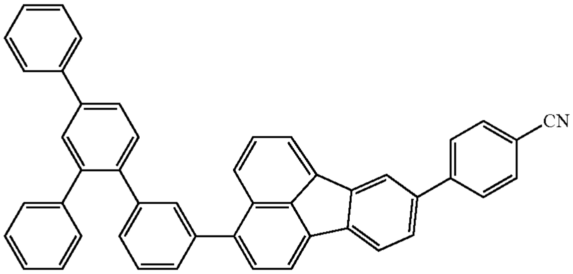

A194

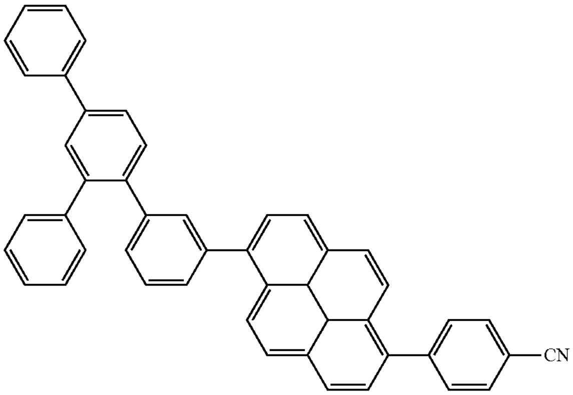

-continued

A195

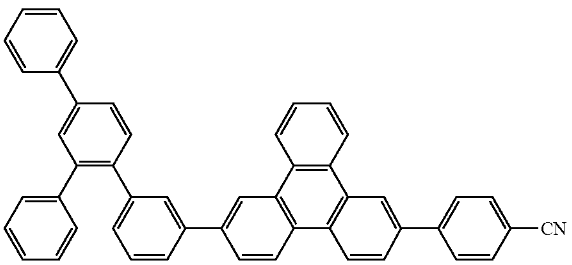

Electrical n-Dopant

Under electrical n-dopant, it is understood a compound which, if embedded into an electron transport matrix, improves, in comparison with the neat matrix under the same physical conditions, the electron properties of the formed organic material, particularly in terms of electron injection and/or electron conductivity.

In the context of the present invention "embedded into an electron transport matrix" means homogenously mixed with the electron transport matrix.

The electrical n-dopant may be selected from elemental metals, metal salts, metal complexes and organic radicals.

In one embodiment, the electrical n-dopant is selected from alkali metal salts and alkali metal complexes; preferably from lithium salts and lithium organic complexes; more preferably from lithium halides and lithium organic chelates; even more preferably from lithium fluoride, a lithium quinolinolate, lithium borate, lithium phenolate, lithium pyridinolate or from a lithium complex with a Schiff base ligand; most preferably, the lithium quinolinolate complex has the formula II, III or IV:

(II)

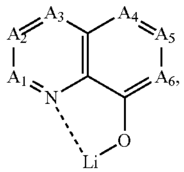

(III)

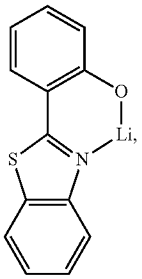

(IV)

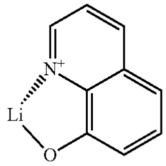

wherein

A1 to A6 are same or independently selected from CH, CR, N, O;

R is same or independently selected from hydrogen, halogen, alkyl or aryl or heteroaryl with 1 to 20 carbon atoms; and more preferred A1 to A6 are CH, the borate based organic ligand is a tetra(1H-pyrazol-1-yl)borate, the phenolate is a 2-(pyridin-2-yl)phenolate, a 2-(diphenylphosphoryl)phenolate, an imidazol phenolate, 2-(pyridin-2-yl)phenolate or 2-(1-phenyl-1H-benzo[d]imidazol-2-yl)phenolate, the pyridinolate is a 2-(diphenylphosphoryl)pyridin-3-olate, the lithium Schiff base has the structure 100, 101, 102 or 103:

100

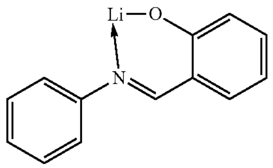

101

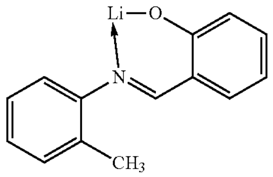

102

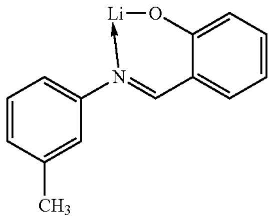

103

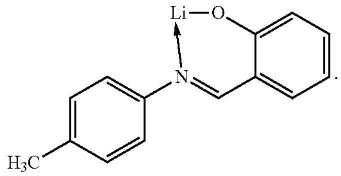

In another embodiment, the electrical n-dopant is a redox n-dopant.

Redox n-Dopant

Under redox n-dopant, it is understood a compound which, if embedded into an electron transport matrix, increases concentration of free electrons in comparison with the neat matrix under the same physical conditions.

The redox n-dopant may not emit light under the operation condition of an electroluminescent device, for example an OLED. In one embodiment, the redox n-dopant is selected from an elemental metal, an electrically neutral metal complex and/or an electrically neutral organic radical.

The most practical benchmark for the strength of an n-dopant is the value of its redox potential. There is no particular limitation in terms how negative the value of the redox potential can be.

As reduction potentials of usual electron transport matrices used in organic semiconductors are, if measured by cyclic voltammetry against ferrocene/ferrocenium reference redox couple, roughly in the range from about −0.8 V to about −3.1V; the practically applicable range of redox potentials for n-dopants which can effectively n-dope such matrices is in a slightly broader range, from about −0.5 to about −3.3 V.

The measurement of redox potentials is practically performed for a corresponding redox couple consisting of the reduced and of the oxidized form of the same compound. In case that the redox n-dopant is an electrically neutral metal complex and/or an electrically neutral organic radical, the measurement of its redox potential is actually performed for the redox couple formed by (i) the electrically neutral metal complex and its cation radical formed by an abstraction of one electron from the electrically neutral metal complex, or (ii) the electrically neutral organic radical and its cation formed by an abstraction of one electron from the electrically neutral organic radical.

Preferably, the redox potential of the electrically neutral metal complex and/or of the electrically neutral organic radical may have a value which is more negative than −0.5 V, preferably more negative than −1.2 V, more preferably more negative than −1.7 V, even more preferably more negative than −2.1 V, most preferably more negative than −2.5 V, if measured by cyclic voltammetry against ferrocene/ferrocenium reference redox couple for a corresponding redox couple consisting of (i) the electrically neutral metal complex and its cation radical formed by an abstraction of one electron from the electrically neutral metal complex, or (ii) the electrically neutral organic radical and its cation formed by an abstraction of one electron from the electrically neutral organic radical.

In a preferred embodiment, the redox potential of the n-dopant is between the value which is about 0.5 V more positive and the value which is about 0.5 V more negative than the value of the reduction potential of the chosen electron transport matrix.

Electrically neutral metal complexes suitable as redox n-dopants may be e.g. strongly reductive compelxes of some transition metals in low oxidation state. Particularly strong redox n-dopants may be selected for example from Cr(II), Mo(II) and/or W(II) guanidinate complexes such as $W_2(hpp)_4$, as described in more detail in WO2005/086251.

Electrically neutral organic radicals suitable as redox n-dopants may be e.g. organic radicals created by supply of additional energy from their stable dimers, oligomers or polymers, as described in more detail in EP 1 837 926 B1, WO2007/107306, or WO2007/107356. Under an elemental metal, it is understood a metal in a state of a neat metal, of a metal alloy, or in a state of free atoms or metal clusters. It is understood that metals deposited by vacuum thermal evaporation from a metallic phase, e.g. from a neat bulk metal, vaporize in their elemental form.

It is further understood that if the vaporized elemental metal is deposited together with a covalent matrix, the metal atoms and/or clusters are embedded in the covalent matrix. In other words, it is understood that any metal doped covalent material prepared by vacuum thermal evaporation contains the metal at least partially in its elemental form.

For the use in consumer electronics, only metals containing stable nuclides or nuclides having very long halftime of radioactive decay might be applicable. As an acceptable level of nuclear stability, the nuclear stability of natural potassium can be taken.

In one embodiment, the n-dopant may be selected from electropositive metals selected from alkali metals, alkaline earth metals, rare earth metals and metals of the first transition period Ti, V, Cr and Mn. Preferably, the n-dopant may be selected from Li, Na, K, Rb, Cs, Mg, Ca, Sr, Ba, Sm, Eu, Tm, Yb; more preferably from Li, Na, K, Rb, Cs, Mg and Yb, even more preferably from Li, Na, Cs and Yb, most preferably from Li, Na and Yb.

The redox dopant may be essentially non-emissive.

According to another aspect of the invention, it is provided an electronic device comprising a first electrode, a second electrode, and arranged between the first and second electrode, a layer comprising the organic material according to invention. The layer of the organic material according to invention may serve as an electron transport layer and/or a hole blocking layer. In one embodiment, the electronic device is an electroluminescent device. Preferably, the electroluminescent device is an organic light emitting diode.

According to another aspect of the invention, it is provided an electronic device comprising at least one electroluminescent device according to any embodiment described throughout this application, preferably, the electronic device comprises the organic light emitting diode in one of embodiments described throughout this application. More preferably, the electronic device is a display device.

DESCRIPTION OF THE DRAWINGS

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, characteristics and advantages of the object of the invention are disclosed in the subclaims and the following description of the respective figures—which in an exemplary fashion—show preferred embodiments according to the invention. Any embodiment does not necessarily represent the full scope of the invention, however, and reference is made therefore to the claims and herein for interpreting the scope of the invention. It is to be understood that both the foregoing general description and the following detailed description are exemplary and explanatory only and are intended to provide further explanation of the present invention as claimed.

Hereinafter, the figures are illustrated in more detail with reference to examples. However, the present disclosure is not limited to the following figures.

Figure 1:
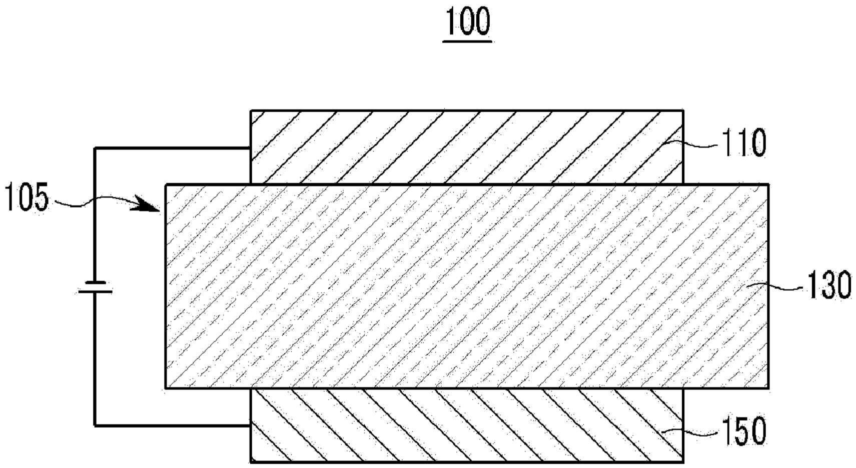
FIG. 1 is a cross-sectional view showing an organic light emitting diode according to an embodiment of the invention.
Figure 2:
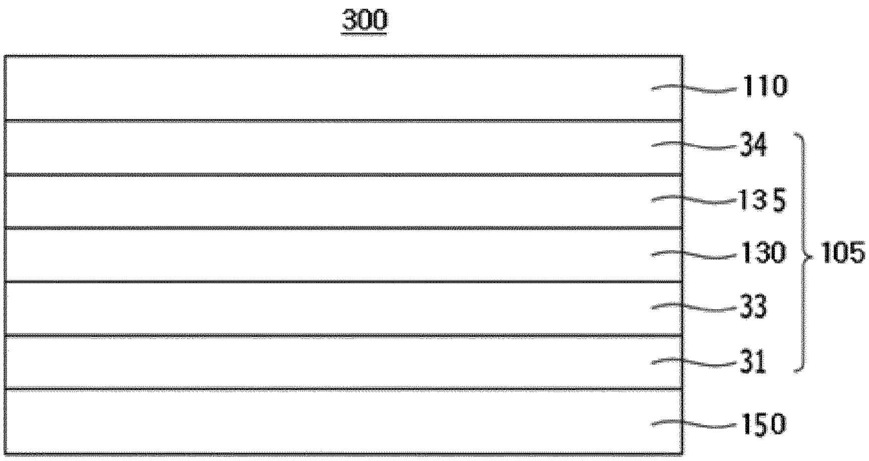
FIGS. 2 and 3 are cross-sectional views specifically showing a part of an organic layer of an organic light emitting diode according to an embodiment of the invention.
Figure 3:
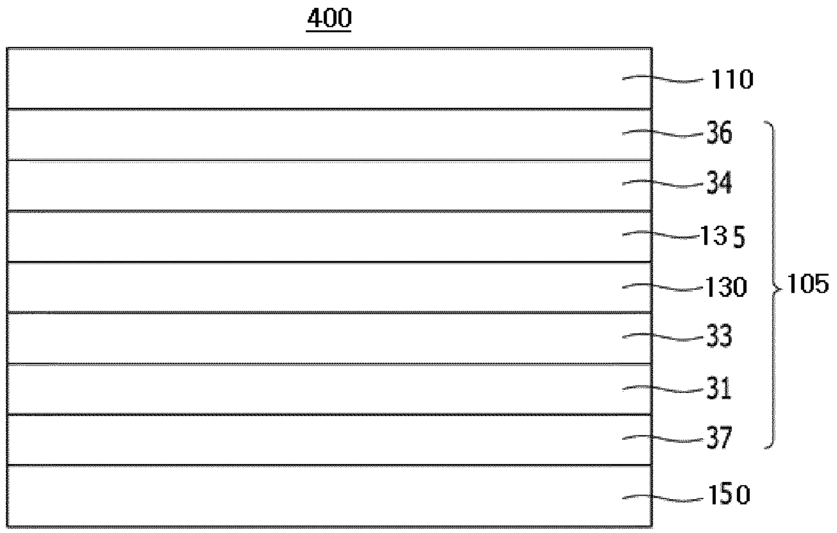

FIGS. 1 to 3 are schematic cross-sectional views of organic light emitting diodes 100, 300, and 400 according to an embodiment of the present invention. Hereinafter, referring to FIG. 1, a structure of an organic light emitting diode according to an embodiment of the present invention and a method of manufacturing the same are as follows. The organic light emitting diode 100 has a structure where an anode 110, a stack of organic layers 105 including an optional hole transport region; an emission layer 130; and a cathode 150 that are sequentially stacked.

A substrate may be disposed on the anode 110 or under the cathode 150. The substrate may be selected from usual substrate used in a general organic light emitting diode and may be a glass substrate or a transparent plastic substrate.

The anode 110 may be formed by depositing or sputtering an anode material on a substrate. The anode material may be selected from materials having a high work function that makes hole injection easy. The anode 110 may be a reflective electrode, a transflective electrode, or a transmissive electrode. The anode material may use indium tin oxide (ITO), indium zinc oxide (IZO), tin oxide ($SnO_2$), zinc oxide (ZnO), and the like. Or, it may be a metal such as silver (Ag), or gold (Au), or an alloy thereof.

The anode 110 may have a monolayer or a multi-layer structure of two or more layers.

The organic light emitting diodes 100, 300, and 400 according to an embodiment of the present invention may include a hole transport region; an emission layer 130; and a first electron transport layer 31 comprising a compound according to formula I.

Referring to FIG. 2, the hole transport region of the stack of organic layers 105 may include at least two layered hole transport layers, and in this case, the hole transport layer contacting the emission layer (130) is defined as a second hole transport layer 135 and a the hole transport layer contacting the anode (110) is defined as a first hole transport layer 34. The stack of organic layers 105 further includes two further layers, namely a hole blocking layer 33 and a electron transport layer 31. The hole transport region of the stack 105 may further include at least one of a hole injection layer, a hole transport layer, an electron blocking layer, and a buffer layer.

The hole transport region of the stack 105 may include only hole injection layer or only hole transport layer. Or, the hole transport region may have a structure where a hole injection layer 36/hole transport layer 34 or hole injection layer 36/hole transport layer 34/electron blocking layer (135) is sequentially stacked from the anode 110.

For example, the hole injection layer 36 and the electron injection layer 37 can be additionally included, so that an OLED may comprise an anode 110/hole injection layer 36/first hole transport layer 34/electron blocking layer 135/emission layer 130/hole blocking layer 33/electron transport layer 31/electron injection layer 37/cathode 150, which are sequentially stacked.

According to another aspect of the invention, the organic electroluminescent device (400) comprises an anode (110), a hole injection layer (36), a first hole transport layer (34), optional an electron blocking layer (135), an emission layer (130), hole blocking layer (33), electron transport layer (31), an optional electron injection layer (37), a cathode (150) wherein the layers are arranged in that order.

The hole injection layer 36 may improve interface properties between ITO as an anode and an organic material used for the hole transport layer 34, and may be applied on a non-planarized ITO and thus planarizes the surface of the ITO. For example, the hole injection layer 36 may include a material having a median value of the energy level of its highest occupied molecular orbital (HOMO) between the work function of ITO and the energy level of the HOMO of the hole transport layer 34, in order to adjust a difference between the work function of ITO as an anode and the energy level of the HOMO of the first hole transport layer 34.

When the hole transport region includes a hole injection layer 36, the hole injection layer may be formed on the anode 110 by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport transport part of the charge transport region includes the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in driving voltage.

Hole transport matrix materials used in the hole transport region are not particularly limited. Preferred are covalent compounds comprising a conjugated system of at least 6 delocalized electrons. The term "covalent compound" is in more detail explained below, in the paragraph regarding the second electron transport matrix. Typical examples of hole transport matrix materials which are widely used in hole transport layers are polycyclic aromatic hydrocarbons, triaryl amine compounds and heterocyclic aromatic compounds. Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

The hole transport region of the stack of organic layers may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as compound HT-D1 below.

Compound HT-D1

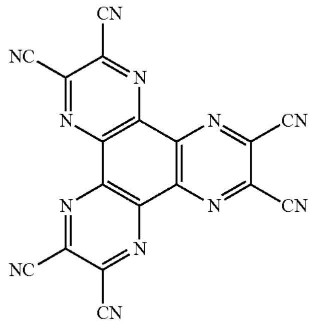

F4-TCNQ

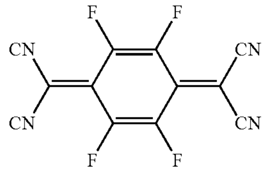

The hole transport part of the charge transport region may further include a buffer layer.

The buffer layer may compensate for an optical resonance distance of light according to a wavelength of the light emitted from the EML, and thus may increase efficiency.

The emission layer (EML) may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

The emitter may be a red, green, or blue emitter.

In one embodiment, the emitter host is an anthracene matrix compound represented by formula 400 below:

Formula 400

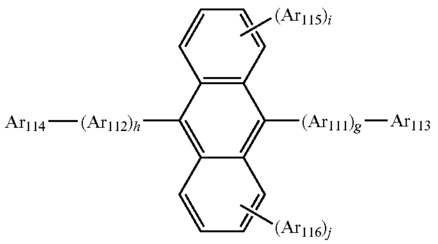

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ aryl group; and g, h, i, and j may be each independently an integer from 0 to 4. In some embodiments, $Ar_{111}$ and $Ar_{112}$ in formula 400 may be each independently one of a phenylene group, a naphthylene group, a phenanthrenylene group, or a pyrenylene group; or a phenylene group, a naphthylene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2. In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

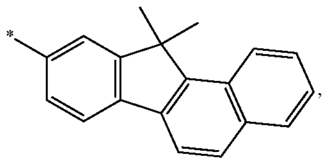 [SMILES: *c1ccc2c(c1)C(C)(C)c1c-2ccc2ccccc12]

or formulas (Y2) or (Y3):

(Y2)

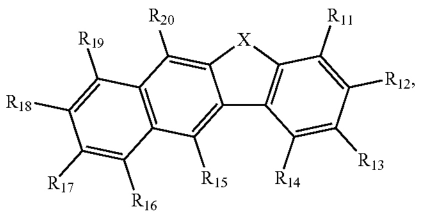

(Y3)

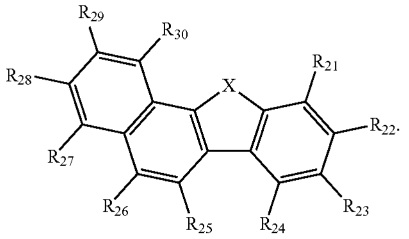

Wherein in the formulas (Y2) and (Y3), X is selected form an oxygen atom and a sulfur atom, but embodiments of the invention are not limited thereto.

In the formula (Y2), any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula (Y3), any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group consisting of N, O or S. More preferred the EML host comprises one heteroatom selected from S or O.

According to a further aspect of the invention, the emitter host respectively has a reduction potential which, if measured under the same conditions by cyclic voltammetry against $Fc/Fc^+$ in tetrahydrofuran, has a value more negative than the respective value obtained for 7-([1,1'-biphenyl]-4-yl)dibenzo[c,h]acridine, preferably more negative than the respective value for 9,9',10,10'-tetraphenyl-2,2'-bianthracene, more preferably more negative than the respective value for 2,9-di([1,1'-biphenyl]-4-yl)-4,7-diphenyl-1,10-phenanthroline, even more preferably more negative than the respective value for 2,4,7,9-tetraphenyl-1,10-phenanthroline, even more preferably more negative than the respective value for 9,10-di(naphthalen-2-yl)-2-phenylanthracene, even more preferably more negative than the respective value for 2,9-bis(2-methoxyphenyl)-4,7-diphenyl-1,10-phenanthroline, most preferably more negative than the respective value for 9,9'-spirobi[fluorene]-2,7-diylbis(diphenylphosphine oxide).

The emitter is mixed in a small amount to cause light emission, and may be generally a material such as a metal complex that emits light by multiple excitation into a triplet or more. The emitter may be, for example an inorganic, organic, or organometallic compound, and one or more kinds thereof may be used.

The emitter may be a fluorescent emitter, for example ter-fluorene, the structures are shown below. 4.4'-bis(4-diphenyl amiostyryl)biphenyl (DPAVBi), 2,5,8,11-tetra-tert-butyl perylene (TBPe), and Compound 4 below are examples of fluorescent blue emitters.

Compound 4

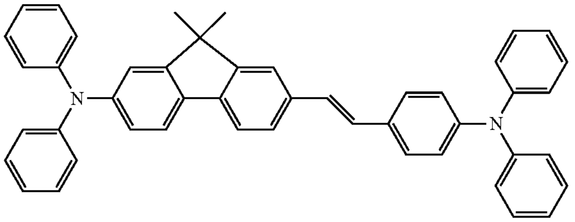

According to another aspect, the organic semiconductor layer comprising a compound of formula I is arranged between a fluorescent blue emission layer and the cathode electrode.

The emitter may be a phosphorescent emitter, and examples of the phosphorescent emitters may be organometallic compounds including Ir, Pt, Os, Ti, Zr, Hf, Eu, Tb, Tm, Fe, Co, Ni, Ru, Rh, Pd, or a combination thereof. The phosphorescent emitter may be, for example a compound represented by formula Z, but is not limited thereto:

$$L_2MX \quad (Z).$$

In formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or, in a polynuclear complex, a combination thereof, and the L and X may be, for example, a bidendate ligand.

A thickness of the emission layer may be about 10 nm to about 100 nm, for example about 20 nm to about 60 nm. When the thickness of the emission layer is within these ranges, the emission layer may have improved emission characteristics without a substantial increase in a driving voltage.

Next, the electron transport region of the stack of organic layers 105 is disposed on the emission layer.

The electron transport region of the stack of organic layers includes at least an electron transport layer. The electron transport region of the stack of organic layers may further include an electron injection layer and/or a hole blocking layer. At least an electron transport layer comprises the n-doped organic material according to one of its various embodiments.

For example, the electron transport region of the stack of organic layers may have a structure of an electron transport layer/hole blocking layer/electron injection layer but is not limited thereto. For example, an organic light emitting diode according to an embodiment of the present invention includes at least two electron transport layers in the electron transport region of the stack of organic layers 105, and in this case, the layer contacting the emission layer is a hole blocking layer 33.

The electron transport layer may include two or more different electron transport matrix compounds.

Second Electron Transport Matrix Compound

Various embodiments of the electron transport region in the device according to invention, e.g. devices comprising hole blocking layers, electron injecting layers, may comprise a second electron transport matrix compound. The second electron transport matrix compound may be a compound of formula (I).

Second electron transport matrix is not particularly limited. Similarly as other materials which are in the inventive device comprised outside the emitting layer, the second electron transport matrix may not emit light.

According to one embodiment, the second electron transport matrix can be an organic compound, an organometallic compound, or a metal complex.

According to one embodiment, the second electron transport matrix may be a covalent compound comprising a conjugated system of at least 6 delocalized electrons. Under a covalent material in a broadest possible sense, it might be understood a material, wherein at least 50% of all chemical bonds are covalent bonds, wherein coordination bonds are also considered as covalent bonds. In the present application, the term encompasses in the broadest sense all usual electron transport matrices which are predominantly selected from organic compounds but also e.g. from compounds comprising structural moieties which do not comprise carbon, for example substituted 2,4,6-tribora-1,3,5 triazines, or from metal complexes, for example aluminium tris(8-hydroxyquinolinolate).

The molecular covalent materials can comprise low molecular weight compounds which may be, preferably, stable enough to be processable by vacuum thermal evaporation (VTE). Alternatively, covalent materials can comprise polymeric covalent compounds, preferably, compounds soluble in a solvent and thus processable in form of a solution. It is to be understood that a polymeric substantially covalent material may be crosslinked to form an infinite irregular network, however, it is supposed that such crosslinked polymeric substantially covalent matrix compound still comprises both skeletal as well as peripheral atoms. Skeletal atoms of the covalent compound are covalently bound to at least two neighbour atoms. Other atoms of the covalent compound are peripheral atoms which are covalently bound with a single neighbour atom. Inorganic infinite crystals or fully crosslinked networks having partly covalent bonding but substantially lacking peripheral atoms, like silicon, germanium, gallium arsenide, indium phosphide, zinc sulfide, silicate glass etc. are not considered as covalent matrices in the sense of present application, because such fully crosslinked covalent materials comprise peripheral atoms only on the surface of the phase formed by such material. A compound comprising cations and anions is still considered as covalent, if at least the cation or at least the anion comprises at least ten covalently bound atoms.

Preferred examples of covalent second electron transport matrix compounds are organic compounds, consisting predominantly from covalently bound C, H, O, N, S, which may optionally comprise also covalently bound B, P, As, Se. In one embodiment, the second electron transport matrix compound lacks metal atoms and majority of its skeletal atoms is selected from C, O, S, N.

In another embodiment, the second electron transport matrix compound comprises a conjugated system of at least six, more preferably at least ten, even more preferably at least fourteen delocalized electrons.

Examples of conjugated systems of delocalized electrons are systems of alternating pi- and sigma bonds. Optionally, one or more two-atom structural units having the pi-bond between its atoms can be replaced by an atom bearing at least one lone electron pair, typically by a divalent atom selected from O, S, Se, Te or by a trivalent atom selected from N, P, As, Sb, Bi. Preferably, the conjugated system of delocalized electrons comprises at least one aromatic or heteroaromatic ring adhering to the Hückel rule. Also preferably, the second electron transport matrix compound may comprise at least two aromatic or heteroaromatic rings which are either linked by a covalent bond or condensed.

In one of specific embodiments, the second electron transport matrix compound comprises a ring consisting of covalently bound atoms and at least one atom in the ring is phosphorus.

In a more preferred embodiment, the phosphorus-containing ring consisting of covalently bound atoms is a phosphepine ring.

In another preferred embodiment, the covalent matrix compound comprises a phosphine oxide group. Also preferably, the substantially covalent matrix compound comprises a heterocyclic ring comprising at least one nitrogen atom. Examples of nitrogen containing heterocyclic compounds which are particularly advantageous as second electron transport matrix compound for the inventive device are matrices comprising, alone or in combination, pyridine structural moieties, diazine structural moieties, triazine structural moieties, quinoline structural moieties, benzoquinoline structural moieties, quinazoline structural moieties, acridine structural moieties, benzacridine structural moieties, dibenzacridine structural moieties, diazole structural moieties and benzodiazole structural moieties.

The second matrix compound may have a molecular weight (Mw) of ≥400 to ≤850 g/mol, preferably ≥450 to ≤830 g/mol. If the molecular weight is selected in this range, particularly reproducible evaporation and deposition can be achieved in vacuum at temperatures where good long-term stability is observed.

Preferably, the second matrix compound may be essentially non-emissive.

According to another aspect, the reduction potential of the second matrix compound may be selected more negative than −2.2 V and less negative than −2.35 V against $Fc/Fc^+$ in tetrahydrofuran, preferably more negative than −2.25 V and less negative than −2.3 V.

According to one embodiment, the first and the second matrix compound may be selected different, and the second electron transport layer may consist of a second matrix compound; and the first electron transport layer may consist of the organic material of formula (I), and an electrical n-dopant, preferably an alkali metal salt or an alkali metal organic complex.

Preferably, the first and second electron transport layer may be essentially non-emissive.

According to one embodiment the hole blocking layer may comprise the organic material of formula (I).

According to another embodiment, the second electron transport layer can be in direct contact with the emission layer.

According to another embodiment, the electron transport layer can be in direct contact with a hole blocking layer.

According to another embodiment, the second electron transport layer can be contacting sandwiched between the emission layer and the first electron transport layer.

According to another embodiment, the first electron transport layer can be in direct contact with the electron injection layer.

According to another embodiment, the first electron transport layer can be contacting sandwiched between the second electron transport layer and the electron injection layer.

According to another embodiment, the first electron transport layer can be in direct contact with the cathode electrode.

According to another embodiment, the first electron transport layer can be contacting sandwiched between the second electron transport layer and the cathode layer.

According to another embodiment, the second electron transport layer can be contacting sandwiched between the emission layer and the first electron transport layer, and the first electron transport layer can be contacting sandwiched between the second electron transport layer and the electron injection layer or sandwiched between the second electron transport layer and the hole blocking layer The formation conditions of the first electron transport layer 31, hole blocking layer 33, and electron injection layer 37 of the electron transport region of the stack of organic layers refer to the formation conditions of the hole injection layer.

The thickness of the first electron transport layer may be from about 2 nm to about 100 nm, for example about 3 nm to about 30 nm. When the thickness of the first electron transport layer is within these ranges, the first electron transport layer may have improved electron transport auxiliary ability without a substantial increase in driving voltage.

A thickness of the second electron transport layer may be about 10 nm to about 100 nm, for example about 15 nm to about 50 nm. When the thickness of the electron transport layer is within these ranges, the electron transport layer may have satisfactory electron transporting ability without a substantial increase in driving voltage.

According to another aspect of the invention, the organic electroluminescent device further comprises an electron injection layer between the second electron transport layer and the cathode.

The electron injection layer (EIL) 37 may facilitate injection of electrons from the cathode 150.

According to another aspect of the invention, the electron injection layer 37 comprises:

(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or (ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in driving voltage.

A material for the cathode 150 may be a metal, an alloy, or an electrically conductive compound that have a low work function, or a combination thereof. Specific examples of the material for the cathode 150 may be lithium (Li), magnesium (Mg), aluminum (Al), aluminum-lithium (Al—Li), calcium (Ca), magnesium-indium (Mg—In), magnesium-silver (Mg—Ag), etc. In order to manufacture a top-emission light-emitting device having a reflective anode 110 deposited on a substrate, the cathode 150 may be formed as a transmissive electrode from, for example, indium tin oxide (ITO) or indium zinc oxide (IZO).

In one embodiment, the organic electronic device according to the invention comprising an organic semiconducting layer comprising a compound according to Formula (I) can further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection layer, hole transporting and/or a hole generation layer the later one having the function of generating holes in a charge-generation layer or a p-n-junction.

In one embodiment, the radialene compound may have formula (XX) and/or the quinodimethane compound may have formula (XXIa) or (XXIb):

(XX)

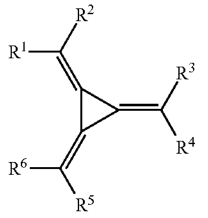

(XXIa)

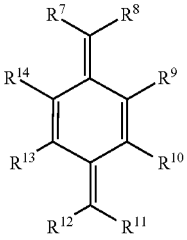

-continued (XXIb)

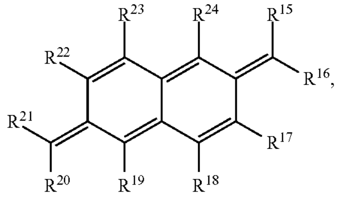

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples.

DETAILED DESCRIPTION

The invention is furthermore illustrated by the following examples which are illustrative only and non-binding.

Synthesis of Compound of Formula 1

Intermediates

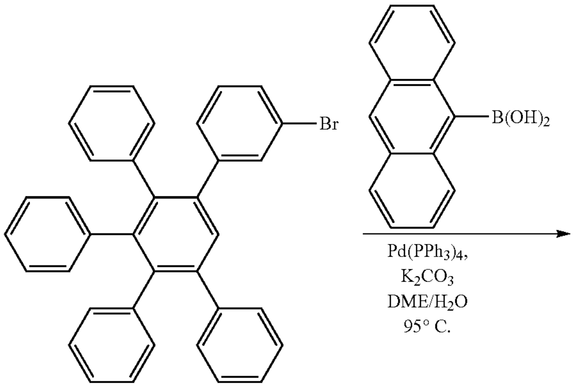

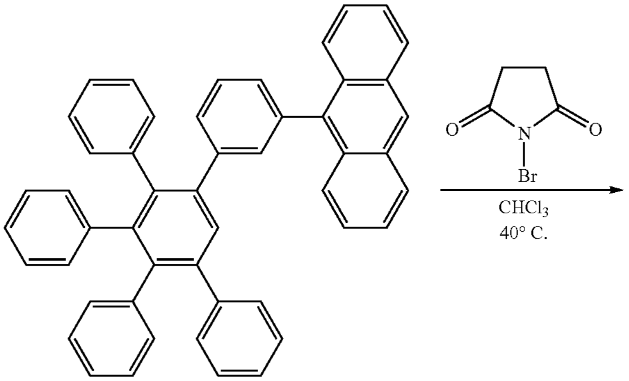

-continued
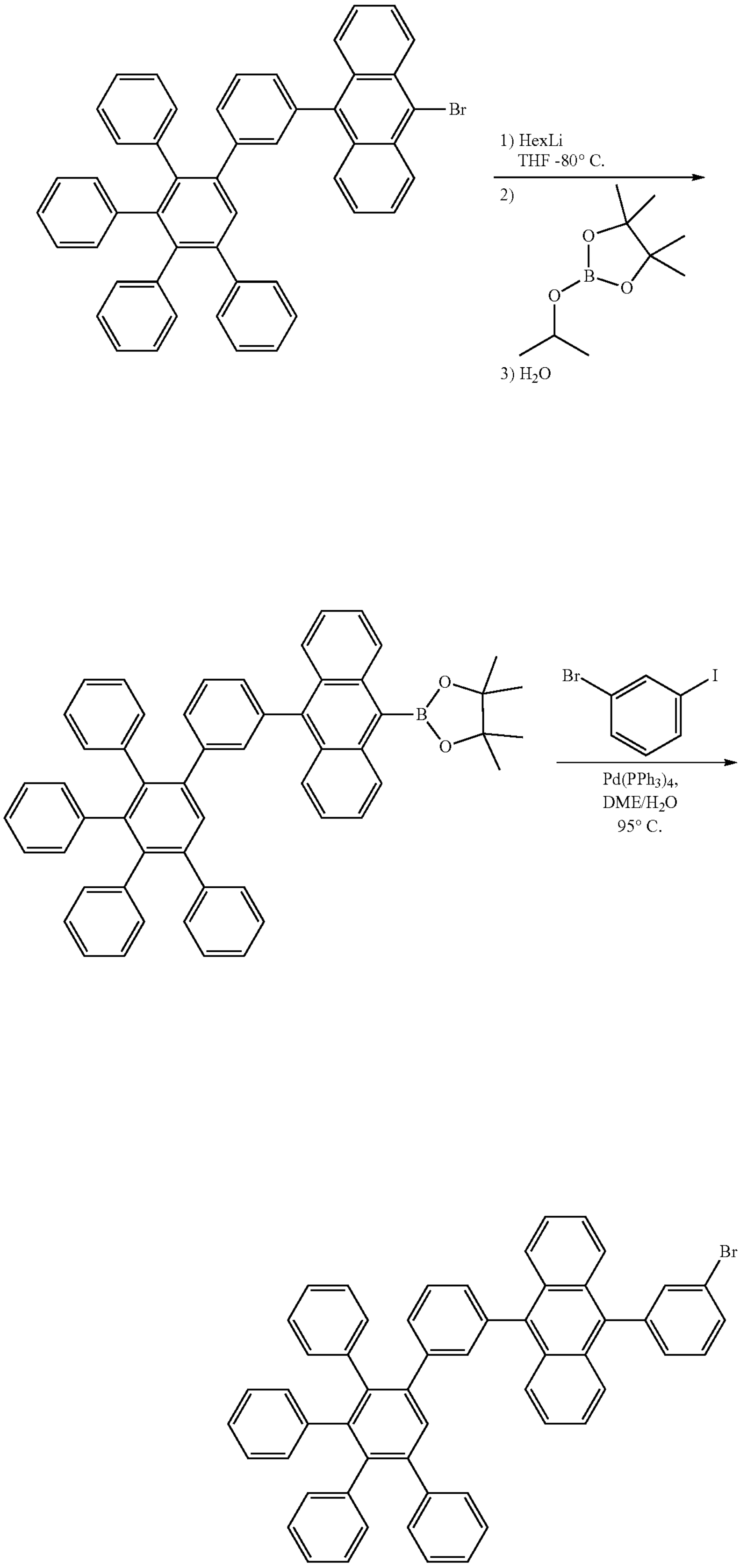

3-bromo-3',4',5'-triphenyl-1,1':2',1"-terphenyl

Synthesis described in Organometallics, 2006, 25(19), 4665-4669.

9-(3',4',5'-triphenyl-[1,1':2',1"-terphenyl]-3-yl)anthracene

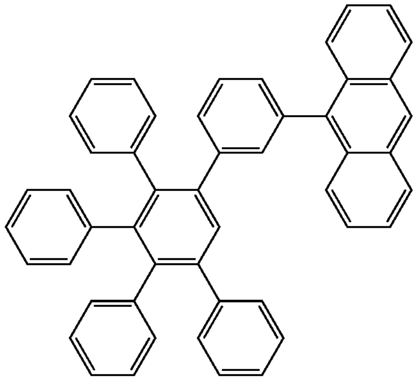 [SMILES: c1ccc(-c2cc(-c3cccc(-c4c5ccccc5cc5ccccc45)c3)c(-c3ccccc3)c(-c3ccccc3)c2-c2ccccc2)cc1]

A flask was flushed with nitrogen and charged with 3-bromo-3',4',5'-triphenyl-1,1':2',1"-terphenyl (150.0 g, 1.0 eq., 279.1 mmol), anthracene boronic acid (74.4 g, 1.2 eq., 334.9 mmol), tetrakis(triphenylphosphine)palladium(0) (6.5 g, 0.02 eq., 5.6 mmol), and potassium carbonate (115.7 g, 3.0 eq., 837.2 mmol). A mixture of deaerated glyme (890 mL) and water (356 mL) was added and the reaction mixture was heated up to 95° C. and left to react under nitrogen atmosphere. After 22 h of reflux, the organic layer was first decanted when hot and then cooled down while stirring. The precipitate was filtered off, rinsed first with glyme (3×10 mL), then with water until pH neutral (1 L) and then again with glyme (2×10 mL). The crude solid was dissolved in chloroform (600 mL). The resulting solution was filtered over silica using chloroform as eluent (400 mL). Hexane (100 mL) was added to the solution and the filtrate was reduced under vacuum till precipitation. Then, 200 mL of hexane were added. The suspension was stirred for 2 h at room temperature. The precipitated was filtered, rinsed with hexane and dried overnight at 40° C. under vacuum to afford the title compound in 74% yield (131.1 g), as a slightly yellow solid. ESI-MS: 657 (634+Na).

9-bromo-10-(3',4',5'-triphenyl-[1,1':2',1"-terphenyl]-3-yl)anthracene

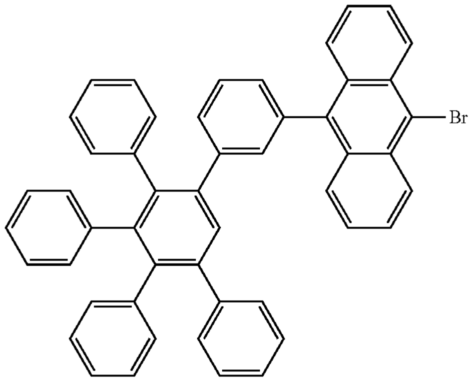 [SMILES: Brc1c2ccccc2c(-c2cccc(-c3cc(-c4ccccc4)c(-c4ccccc4)c(-c4ccccc4)c3-c3ccccc3)c2)c2ccccc12]

9-(3',4',5'-triphenyl-[1,1':2',1"-terphenyl]-3-yl)anthracene (131.8 g, 1.0 eq., 206.0 mmol), N-bromosuccinimide (44.0 g, 1.2 eq., 247.3 mmol) and chloroform (1.4 L) were placed in a flask. The reaction mixture was heated up to 40° C. for three days. Then, it was cooled down to room temperature. Water was added (500 mL) and the mixture was stirred for 1 h. The organic layer was decanted and dried over $MgSO_4$. The drying agent was filtered off, and the solvents in the organic phase were evaporated under vacuum. Hexane (500 mL) was added, and the suspension was stirred at room temperature overnight. The solid was filtered, rinsed with hexane (3×20 mL) and dried overnight at 40° C. under vacuum to afford the title compound in quantitative yield (148 g), as a slightly yellow solid. ESI-MS: 737 (714+Na).

4,4,5,5-tetramethyl-2-(10-(3',4',5'-triphenyl-[1,1':2',1"-terphenyl]-3-yl)anthracen-9-yl)-1,3,2-dioxaborolane

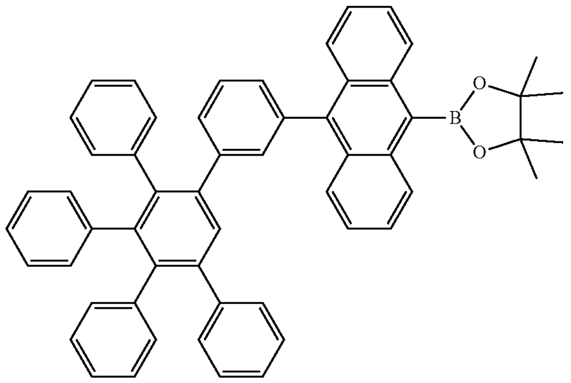 [SMILES: CC1(C)OB(c2c3ccccc3c(-c3cccc(-c4cc(-c5ccccc5)c(-c5ccccc5)c(-c5ccccc5)c4-c4ccccc4)c3)c3ccccc23)OC1(C)C]

To a stirred solution of 9-bromo-10-(3',4',5'-triphenyl-[1,1':2',1"-terphenyl]-3-yl)anthracene (89.2 g, 1.0 eq, 125.0 mmol) in anhydrous THF (600 mL) at −80° C. under nitrogen atmosphere, was added HexLi in hexane (100 mL, 33 wt %, 2.0 eq., 250.0 mmol) and the mixture was stirred for 2 h at the same temperature. Then, 2-isopropoxy-4,4,5,5-tetramethyl-1,3,2-dioxaborolane (69.8 g, 3.0 eq., 375.0 mmol) was added at −80° C. under nitrogen atmosphere and the mixture was stirred overnight while the temperature gradually increased to room temperature. Water was added (100 mL) and THF was evaporated. Dichloromethane (500 mL) and water (300 mL) were added and the organic phase was decanted. The aqueous phase was extracted with dichloromethane (300 mL). Combined organic phases were washed with water (500 mL), then dried over $Na_2SO_4$. Toluene (150 mL) was added, and the solution was reduced under vacuum till precipitation. Then it was cooled down to 0° C. The precipitate was filtered and rinsed first with toluene (2×10 mL) and then with hexane (2×10 mL). The solid was dissolved in hot chloroform and the resulting solution was filtered over silica using chloroform (200 mL) as eluent. Isopropanol (150 mL) was added and the solution was reduced under vacuum to evaporate the chloroform. Then it was left stirring and the precipitate was filtered and rinsed first with isopropanol (2×10 mL) and then with hexane (2×10 mL). It was re-dissolved in chloroform (200 mL), hexane (80 mL) was added and the solution was reduced under vacuum to ca. 90 mL. Precipitate was filtered and dried overnight at 40° C. under vacuum to afford the title compound in 62% yield (68.9 g), as a slightly yellow solid. ESI-MS: 783 (760+Na).

9-(3-bromophenyl)-10-(3',4',5'-triphenyl-[1,1':2',1"-terphenyl]-3-yl)anthracene

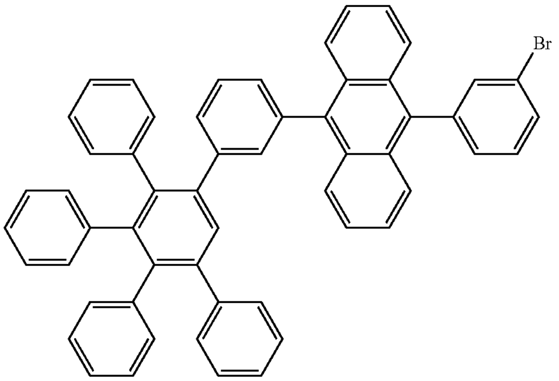 [SMILES: Brc1cccc(-c2c3ccccc3c(-c3cccc(-c4cc(-c5ccccc5)c(-c5ccccc5)c(-c5ccccc5)c4-c4ccccc4)c3)c3ccccc23)c1]

A flask was flushed with nitrogen and charged with 4,4,5,5-tetramethyl-2-(10-(3',4',5'-triphenyl-[1,1':2',1"-terphenyl]-3-yl)anthracen-9-yl)-1,3,2-dioxaborolane (73.8 g, 1.0 eq., 97.0 mmol), 1-bromo-3-iodobenzene (32.9 g, 1.2 eq., 116.4 mmol), tetrakis(triphenylphosphine)palladium(0) (2.2 g, 0.02 eq., 1.9 mmol) and potassium carbonate (40.2 g, 3.0 eq., 291.0 mmol). A deaerated mixture of glyme (364 mL) and water (146 mL) was added and the reaction mixture was heated up to 95° C. and left to react under nitrogen atmosphere. After 3 days of reflux, the reaction mixture was cooled down to room temperature. The precipitate was filtered, rinsed first with glyme (2×10 mL), then with water (5×40 mL) and then with hexane (2×10 mL). The crude solid was dissolved in hot chloroform (1500 mL). The resulting solution was filtered over silica using chloroform as eluent (300 mL). The filtrate was reduced under vacuum till 150 mL and then hexane (150 mL) was added. The suspension was stirred overnight. The precipitated was filtered, rinsed first with chloroform/hexane 1.5/1.0 (2×20 mL), then with hexane (1×20 mL). The crude solid was dissolved in hot chloroform (800 mL) and the resulting solution was filtered over silica using chloroform as eluent (300 mL). The filtrate was reduced under vacuum till 100 mL and then hexane (50 mL) was added. The suspension was stirred overnight. The precipitated was filtered, rinsed first with chloroform/hexane 2.0/1.0 (2×10 mL), then with hexane (1×10 mL) and finally dried overnight at 40° C. under vacuum to afford the title compound in 55% yield (42.3 g), as a white solid. ESI-MS: 811 (788+Na).

Final Compounds:

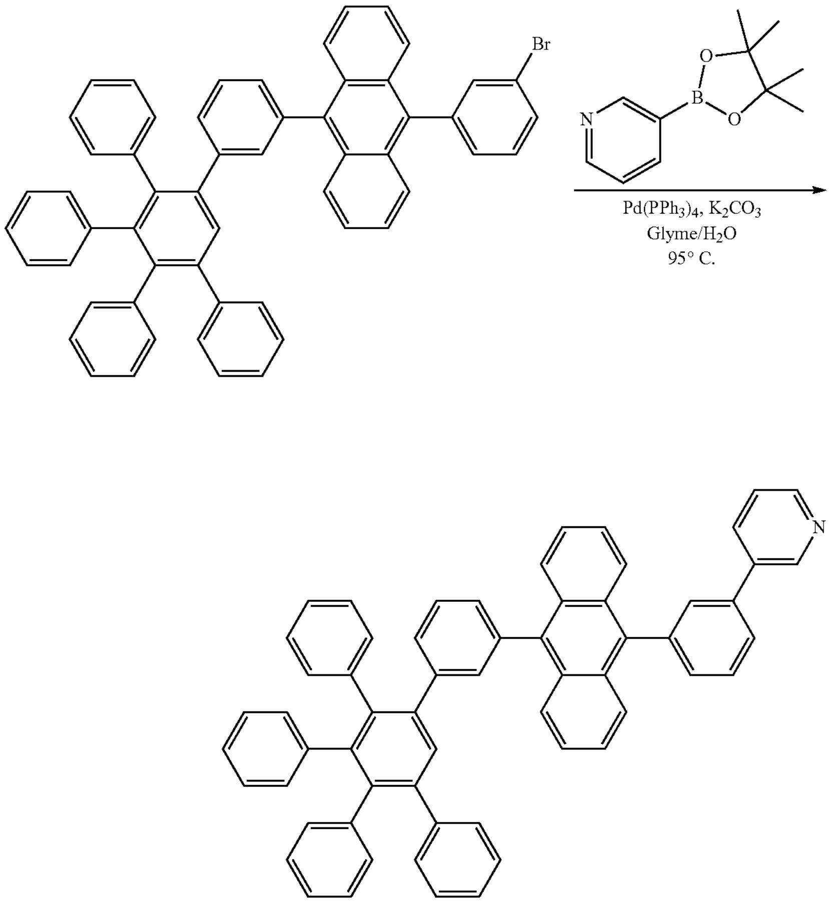

Inv-1

3-(3-(10-(3',4',5'-triphenyl-[1,1':2',1"-terphenyl]-3-yl)anthracen-9-yl)phenyl)pyridine

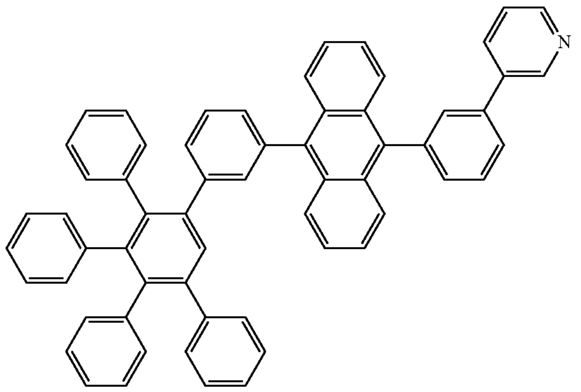 [SMILES: c1ccc(-c2cc(-c3cccc(-c4c5ccccc5c(-c5cccc(-c6cccnc6)c5)c5ccccc45)c3)c(-c3ccccc3)c(-c3ccccc3)c2-c2ccccc2)cc1]

A flask was flushed with nitrogen and charged with 9-bromo-10-(3',4',5'-triphenyl-[1,1':2',1"-terphenyl]-3-yl) anthracene (10.5 g, 1.0 eq., 13.3 mmol), 3-(4,4,5,5-tetramethyl-1,3,2-dioxaborolan-2-yl)pyridine (4.1 g, 1.5 eq., 20.0 mmol), tetrakis(triphenylphosphine)palladium(0) (0.31 g, 0.02 eq., 0.27 mmol) and potassium carbonate (5.5 g, 3.0 eq., 40.0 mmol). A deaerated mixture of glyme (100 mL), toluene (5 mL) and water (20 mL) was added and the mixture was heated up to 95° C. and left to react under nitrogen atmosphere. After 6 days of reflux, the reaction was cooled down. The precipitate was filtered and rinsed first with glyme (2×10 mL) then with water (200 mL) and again with glyme (5 mL). The crude solid was dissolved in hot chloroform (100 mL). The resulting solution was filtered over silica using dichloromethane as eluent (200 mL). Solvent was removed under vacuum. Glyme (80 mL) was added and stirred at 40° C. Hexane was added (50 mL) and it was stirred at room temperature for 1 h. Solid was filtered and washed with hexane. Then, it was re-dissolved in refluxing ethylacetate (235 mL). Ethylacetate was then evaporated until the solid started to precipitate. The suspension was stirred at room temperature for 4 h, then precipitate was filtered and washed with hexane. The solid was one more time re-dissolved in dichloromethane/hexane 1/1 (200 mL) and filtered over silica. Dichloromethane/hexane 1/1 (150 mL) was used first as eluent to remove side products. Then, ethylacetate (300 mL) was used as eluent. Ethylacetate was evaporated to afford the title compound in 24% yield (2.5 g), as a white solid. ESI-MS: 789 (M+H).

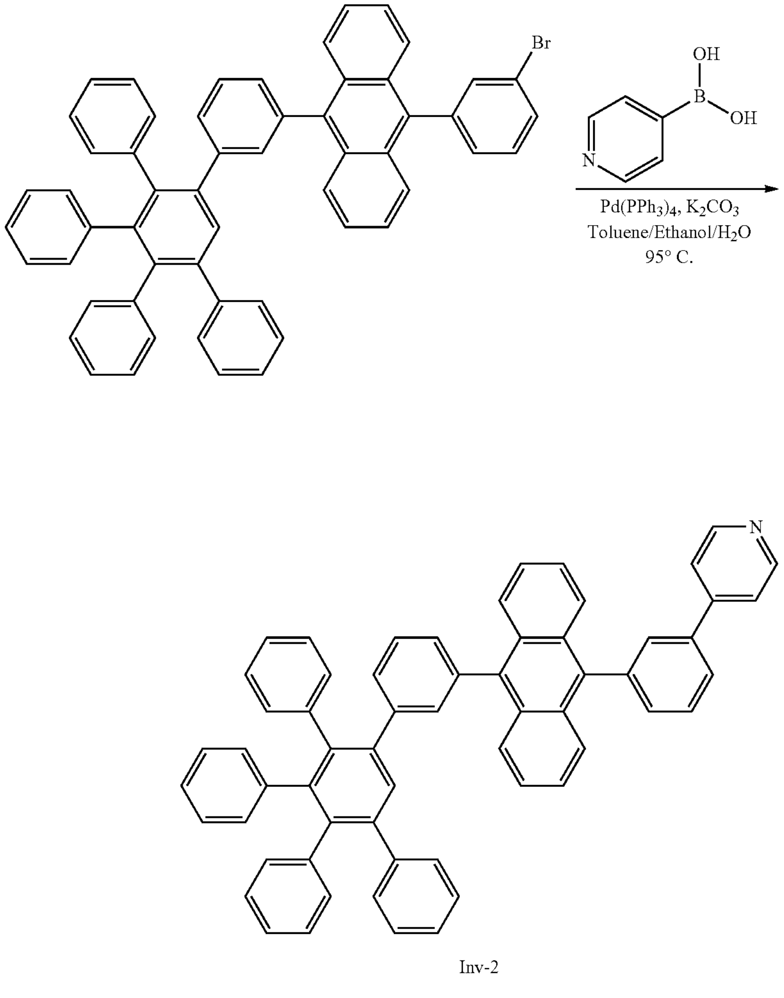

Inv-2

4-(3-(10-(3',4',5'-triphenyl-[1,1':2',1"-terphenyl]-3-yl)anthracen-9-yl)phenyl)pyridine

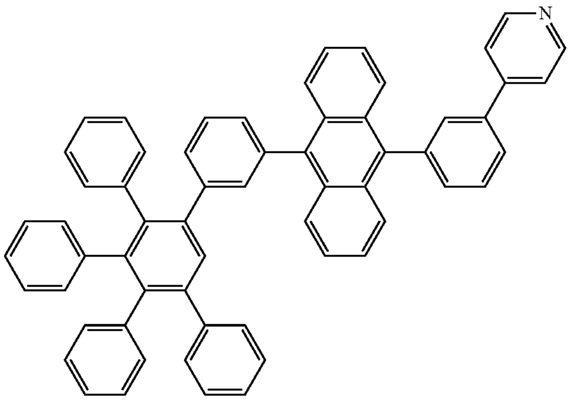 [SMILES: c1ccc(-c2cc(-c3cccc(-c4c5ccccc5c(-c5cccc(-c6ccncc6)c5)c5ccccc45)c3)c(-c3ccccc3)c(-c3ccccc3)c2-c2ccccc2)cc1]

A flask was flushed with nitrogen and charged with 9-bromo-10-(3',4',5'-triphenyl-[1,1':2',1"-terphenyl]-3-yl) anthracene (8.0 g, 1.0 eq., 10.1 mmol), pyridin-4-ylboronic acid (1.7 g, 1.4 eq., 14.2 mmol), tetrakis(triphenylphosphine)palladium(0) (0.23 g, 0.02 eq., 0.2 mmol) and potassium carbonate (4.2 g, 3.0 eq., 30.4 mmol). A deaerated mixture of toluene (160 mL), ethanol (32 mL) and water (16 mL) was added and the reaction mixture was heated up to 95° C. and left to react under nitrogen atmosphere. After 2 days of reflux, the reaction was cooled down and washed with water/brine 1/1 (3 times). The organic phase was decanted, dried over $MgSO_4$, and filtered over silica. Chloroform/hexane 1/1 was used as eluent to get rid of side products and then chloroform (1.5 L) and toluene (200 mL) were used to elute the required compound. Solvents were evaporated up to 20 mL. Hexane (20 mL) was added and the suspension was stirred overnight. Then, precipitate was filtered and washed with hexane (2×5 mL). Solid was dissolved in hexane/dichloromethane 1/1 (200 mL) and filtered over silica. Hexane/Dichloromethane 1/1 (100 mL) was used as eluent to remove side products. Then ethylacetate (500 mL) was used as eluent. Solvents were removed and the solid was boiled in 90 mL of glyme. The solution was cooled down slightly and 60 ml of hexane was added. The mixture was cooled down to room temperature, then the precipitate was filtered and washed with hexane. Finally it was boiled in ethylacetate, cooled to room temperature and the precipitate was filtered and washed with ethylacetate (10 mL) to afford the title compound in 64% yield (5.1 g), as a white solid. ESI-MS: 789 (M+H)

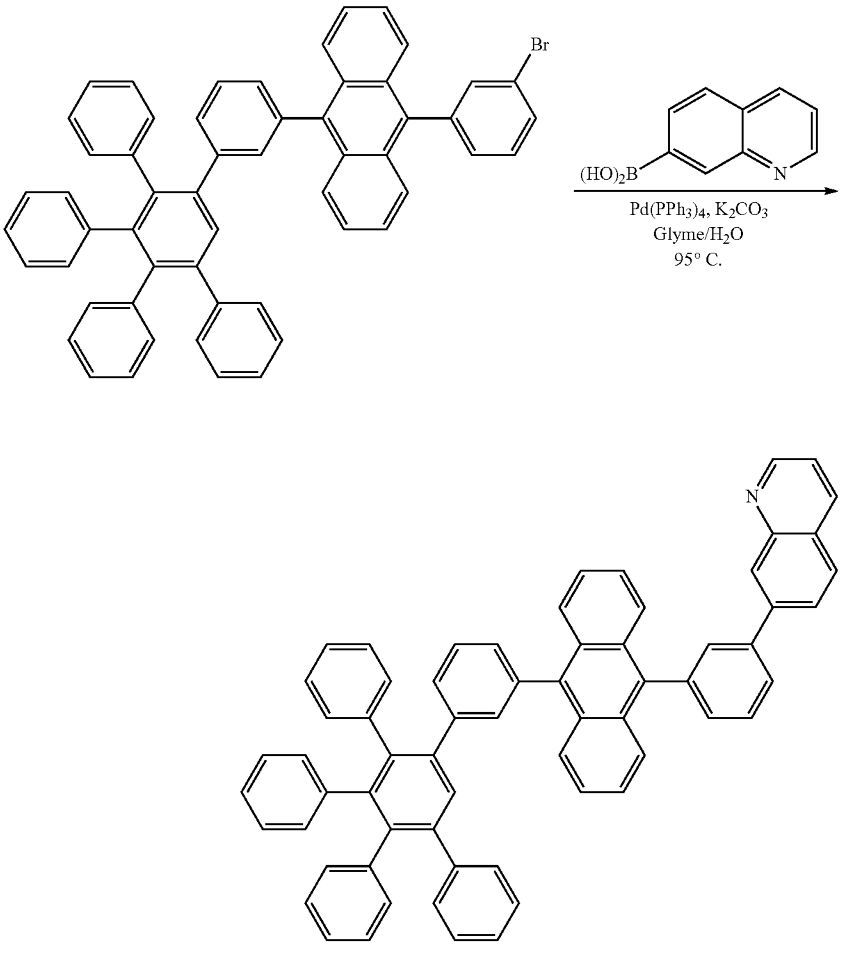

Inv-3

7-(3-(10-(3',4',5'-triphenyl-[1,1':2',1"-terphenyl]-3-yl)anthracen-9-yl)phenyl)quinoline

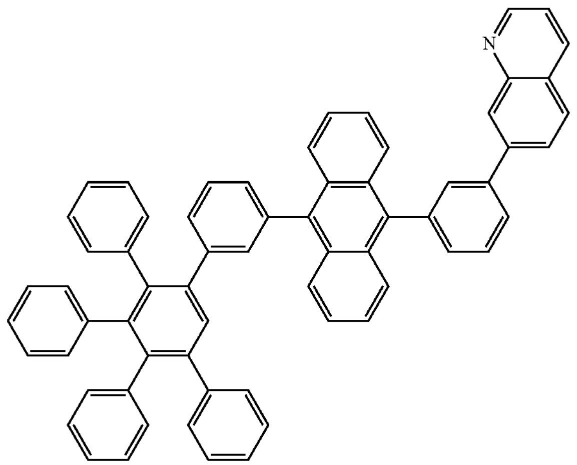 [SMILES: c1ccc(-c2cc(-c3cccc(-c4c5ccccc5c(-c5cccc(-c6ccc7cccnc7c6)c5)c5ccccc45)c3)c(-c3ccccc3)c(-c3ccccc3)c2-c2ccccc2)cc1]

A flask was flushed with nitrogen and charged with 9-bromo-10-(3',4',5'-triphenyl-[1,1':2',1"-terphenyl]-3-yl) anthracene (10.5 g, 1.0 eq., 13.3 mmol), quinolin-7-ylboronic acid (3.0 g, 1.2 eq., 17.3 mmol), tetrakis(triphenylphosphine)palladium(0) (0.23 g, 0.02 eq., 0.2 mmol) and potassium carbonate (5.5 g, 3.0 eq., 138.2 mmol). A deaerated mixture of glyme (90 mL), toluene (5 mL) and water (20 mL) was added and the reaction mixture was heated up to 95° C. and left to react under nitrogen atmosphere. After three days, the reaction was cooled down and the precipitate was filtered and washed first with glyme (10 mL), then with water (150 mL), and finally with glyme (5 mL) and hexane (10 mL). The solid was dissolved in 150 mL of chloroform, filtered over silica and eluted with chloroform (2 L) first, and then with chloroform/methanol (1%). The solvents were almost completely evaporated, and the hexane (30 mL) was added to induce precipitation. The suspension was stirred overnight. The precipitate was filtered and washed with hexane. Crude solid was dissolved in dichloromethane/hexane (1/1) and filtered over silica. Side products were eluted with dichloromethane/hexane 1/1 (40 mL) and ethylacetate (20 mL). The product was eluted with ethylacetate (225 mL). Solvents was evaporated and the residue was dissolved in glyme (35 mL) at room temperature. 10 mL of hexane were added and it was stirred for one hour. The precipitate was filtered and washed with hexane. Finally, the compound was purified by silicagel column chromatography using hexane/ethylacetate (65/35) as eluent. Solvent was evaporated almost completely and after addition of hexane (10 mL), the precipitate was filtered and washed with hexane to afford the title compound in 20% yield (2.2 g) as a white solid. ESI-MS: 839 (M+H)

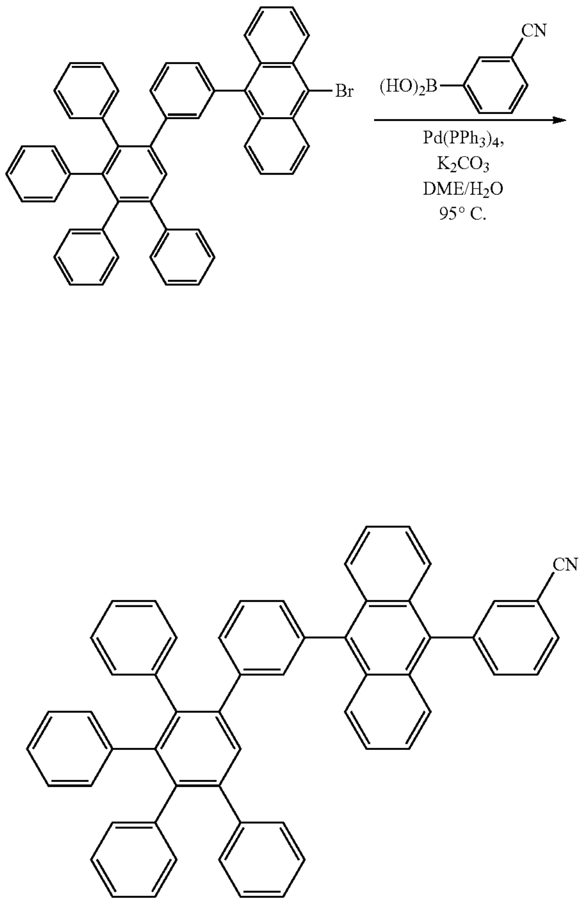

Inv-4

3-(10-(3',4',5'-triphenyl-[1,1':2',1"-terphenyl]-3-yl) anthracen-9-yl)benzonitrile

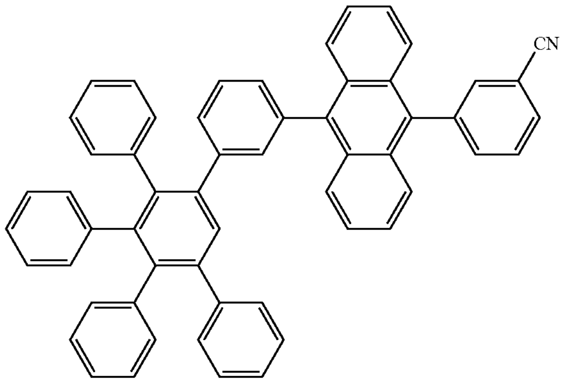 [SMILES: N#Cc1cccc(-c2c3ccccc3c(-c3cccc(-c4cc(-c5ccccc5)c(-c5ccccc5)c(-c5ccccc5)c4-c4ccccc4)c3)c3ccccc23)c1]

A flask was flushed with nitrogen and charged with 9-bromo-10-(3',4',5'-triphenyl-[1,1':2',1"-terphenyl]-3-yl) anthracene (10 g, 1.0 eq., 14.0 mmol), (3-cyanophenyl) boronic acid (2.1 g, 1.0 eq., 14.0 mmol), tetrakis(triphenylphosphine)palladium(0) (0.32 g, 0.02 eq., 0.28 mmol) and potassium carbonate (5.8 g, 3.0 eq., 42.0 mmol). A deaerated mixture fo glyme (70 mL) and water (21 mL) was added and the reaction mixture was heated up to 95° C. and left to react under nitrogen atmosphere. After 2 days of reflux, the reaction was cooled down. The precipitate was filtered and rinsed first with glyme (2×5 mL) then with water (300 mL) and again with glyme (5 mL). The crude solid was dissolved in dichloromethane/hexane 1/1. The resulting solution was filtered over silica. Solvent was evaporated and the crude solid was dissolved in dichloromethane/acetonitrile (200 mL/60 mL). Dichloromethane was partially evaporated to induce precipitation. The precipitate was filtered, washed with hexane and dissolved in hot toluene (30 mL). Acetonitrile (25 mL) was added to induce precipitation and the suspension was stirred overnight. Precipitate was filtered and dried overnight at 80° C. under vacuum to afford the title compound in 23% yield (2.4 g), as a white solid. ESI-MS: 758 (M+Na).

Inv-5

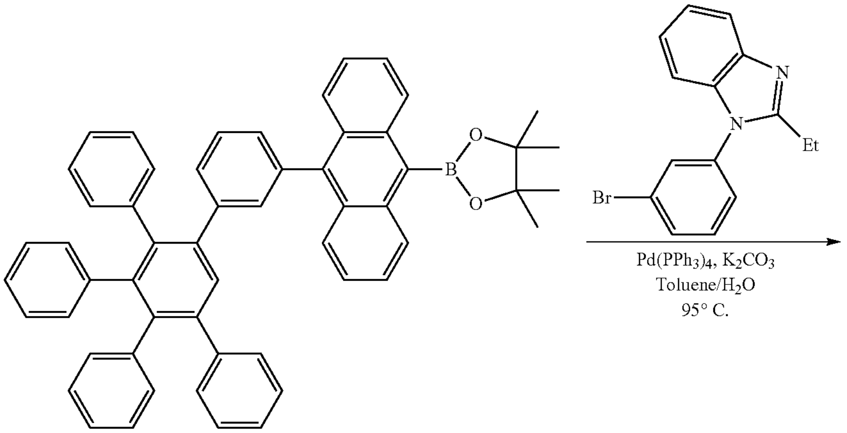

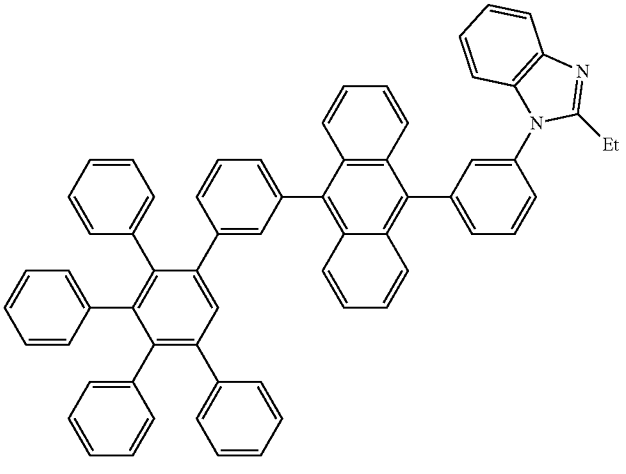

Inv-5

2-Ethyl-1-(3-(10-(3',4',5'-triphenyl-[1,1':2',1"-terphenyl]-3-yl)anthracen-9-yl)phenyl)-1H-benzo[d]imidazole

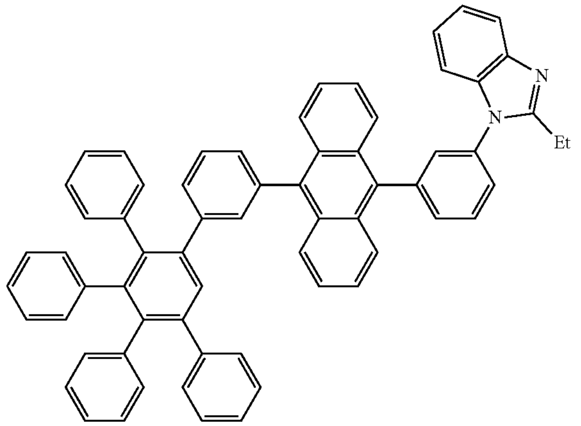 [SMILES: CCc1nc2ccccc2n1-c1cccc(-c2c3ccccc3c(-c3cccc(-c4cc(-c5ccccc5)c(-c5ccccc5)c(-c5ccccc5)c4-c4ccccc4)c3)c3ccccc23)c1]

A flask was flushed with nitrogen and charged with 4,4,5,5-tetramethyl-2-(10-(3',4',5'-triphenyl-[1,1':2',1"-terphenyl]-3-yl)anthracen-9-yl)-1,3,2-dioxaborolane (10.0 g, 1.2 eq., 13.1 mmol), 1-(3-bromophenyl)-2-ethyl-1H-benzo[d]imidazole (3.3 g, 1.0 eq., 10.9 mmol), tetrakis(triphenylphosphine)palladium(0) (0.25 g, 0.02 eq., 0.22 mmol) and potassium carbonate (4.5 g, 3.0 eq., 32.9 mmol). A deaerated mixture of toluene (150 mL) and water (16 mL) was added and the reaction mixture was heated up to 95° C. and left to react under nitrogen atmosphere. After three days of reflux, all volatiles were removed in vacuo, water and dichloromethane were added and the organic phase was washed with water four times. After drying over $MgSO_4$, the organic phase was filtered through a pad of silicagel using first hexane/dichloromethane 1/1 to remove the side products and then dichloromethane to elute the target compound. Solvents were evaporated and crude solid was re-dissolved in glyme (10 mL) and isopropanol was added. Glyme was partially evaporated to induce precipitation. Precipitate was filtered and recrystallized in ethylacetate. Precipitate was filtered and recrystallized in hot DMF (20 mL). Precipitate was filtered, washed with hexane and dried overnight at 80° C. under vacuum to afford the title compound in 32% yield (1.8 g), as a light yellow solid. ESI-MS: 878 (M+Na).

Synthesis of Comparative Compound-1

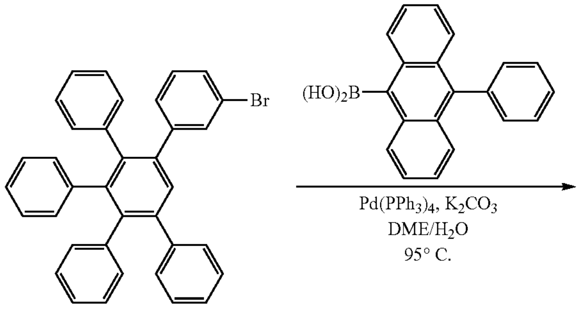

-continued

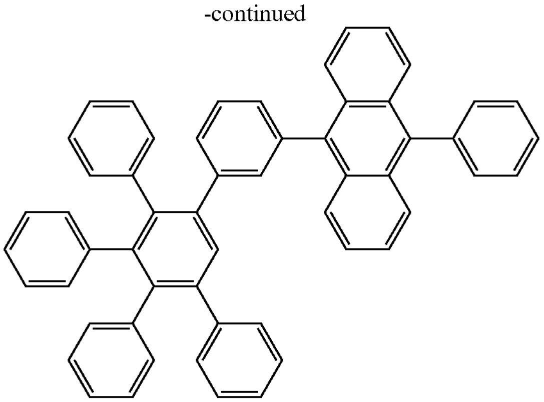

Comparative compound-1

9-phenyl-10-(3',4',5'-triphenyl-[1,1':2',1"-terphenyl]-3-yl)anthracene

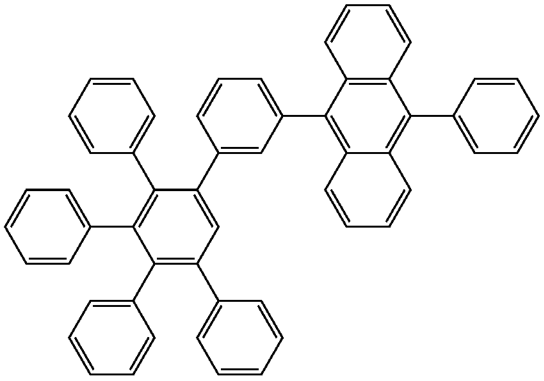 [SMILES: c1ccc(-c2cc(-c3cccc(-c4c5ccccc5c(-c5ccccc5)c5ccccc45)c3)c(-c3ccccc3)c(-c3ccccc3)c2-c2ccccc2)cc1]

A flask was flushed with nitrogen and charged with 3-bromo-3',4',5'-triphenyl-1,1':2',1"-terphenyl (15.0 g, 1.2 eq., 27.9 mmol), (10-phenylanthracen-9-yl)boronic acid (6.0 g, 1.0 eq., 23.2 mmol), tetrakis(triphenylphosphine)palladium(0) (0.54 g, 0.02 eq., 0.47 mmol) and potassium carbonate (9.6 g, 3.0 eq., 69.8 mmol). A deaerated mixture of toluene (300 mL), ethanol (60 mL) and water (30 mL) was added and the reaction mixture was heated up to 95° C. and left to react under nitrogen atmosphere. After 2 days of reflux, the reaction mixture was cooled down to room temperature. The organic layer was then decanted, washed with water (3×150 mL), and dried over $Na_2SO_4$. The drying agent was filtered off. The resulting solution was filtered over silica using toluene (300 mL) as eluent. The filtrate was reduced under vacuum till ca. 60 mL, and hexane (100 mL) was added dropwise. The suspension was stirred overnight. The precipitate was filtered, rinsed first with toluene/hexane 1/2 (10 mL), then with hexane (10 mL). Crude solid was re-dissolved in dichloromethane (100 mL) and hexane was added (150 mL). Precipitate was filtered and washed with dichloromethane/hexane 1/1.5 (2×50 mL). Solid was dissolved in glyme (60 mL), the suspension was cooled down slightly, and precipitation was favored upon addition of hexane (50 mL). The suspension was then cooled down to room temperature and the solid was filtered, washed with hexanes and dried overnight at 80° C. under vacuum to afford the title compound in 30% yield (4.9 g), as a white solid. ESI-MS: 711 (M+H).

General Procedure for Fabrication of OLEDs

For top emission OLED devices, inventive examples and comparative examples, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes, to prepare a first electrode. 100 nm Ag were deposited as anode at a pressure of $10^{-5}$ to $10^{-7}$ mbar to form the anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2"-(cyclopropane-1,2,3-triylidene)tris(2-(p-cyanotetrafluorophenyl)acetonitrile) was vacuum deposited on the ITO electrode, to form a HIL having a thickness of 10 nm. Then, Biphenyl-4-yl(9,9-diphenyl-9H-fluoren-2-yl)-[4-(9-phenyl-9H-carbazol-3-yl) phenyl]-amine was vacuum deposited on the HIL, to form a HTL having a thickness of 118 nm.

Then N,N-bis(4-(dibenzo[b,d]furan-4-yl)phenyl)-[1,1':4',1"-terphenyl]-4-amine (CAS 1198399-61-9) was vacuum deposited on the HTL, to form an electron blocking layer (EBL) having a thickness of 5 nm.

Afterwards the emission layer was deposited. For comparative examples-1, -3 and -4, examples 1 to 6 97 vol.-% H06 (Fluorescent-blue host material) as EML host and 3 vol.-% BD200 (Sun Fine Chemicals) as fluorescent blue dopant were deposited on the EBL, to form a blue-emitting EML with a thickness of 20 nm. For comparative example-2 97 vol.-% H09 (Fluorescent-blue host material) as EML host and 3 vol.-% BD200 (Sun Fine Chemicals) as fluorescent blue dopant were deposited on the EBL, to form a blue-emitting EML with a thickness of 20 nm Then, for top emission OLED devices of configuration A (Table 5, comparative examples-1 and -2 and examples 1 to 3), the hole blocking layer was deposited on the emission layer with a thickness of 5 nm. For examples 1 to 3 compounds of formula 1 were deposited on the emission layer. For comparative examples-1 and -2 the comparative compound-1 and the comparative compound-2, respectively, were deposited on the emission layer. Then, the electron transporting layer is formed on the hole blocking layer with a the thickness of 31 nm by co-deposition of 2-([1,1'-biphenyl]-4-yl)-4-(9,9-diphenyl-9H-fluoren-4-yl)-6-phenyl-1,3,5-triazine (CAS 1801992-44-8) and lithium quinolate (LiQ) in a wt % ratio of 1:1.

For top emission OLED devices of configuration B (Table 6, comparative examples 3- and -4 and example 4 to 6) no hole blocking layer was deposited on the emission layer. For examples 4 to 6 compounds of formula 1 were co-deposited with lithium quinolate (LiQ) in a wt % ratio of 1:1 on the emission layer to form the electron transporting layer with a thickness of 31 nm. For comparative examples-3 and -4 the comparative compound-1 and the comparative compound-2, respectively, were co-deposited with lithium quinolate (LiQ) in a wt % ratio of 1:1 on the emission layer to form the electron transporting layer with a thickness of 31 nm.

Then, for both top emission OLED devices of configuration A and B the electron injection layer is formed on the electron transporting layer by deposing Yb with a thickness of 2 nm.

Ag is evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm nm.

Overview of Compounds Used (Non-Inventive and Non-Comparative)

| IUPAC name | Reference |
|---|---|
| Biphenyl-4-yl(9,9-diphenyl-9H-fluoren-2-yl)-[4-(9-phenyl-9H-carbazol-3-yl)phenyl]-amine (CAS 1242056-42-3) | US2016322581 |
| 4,4',4"-((1E,1'E,1"E)-cyclopropane-1,2,3-triylidenetris(cyanomethanylylidene))tris (2,3,5,6-tetrafluorobenzonitrile) | US2008265216 |
| N,N-bis(4-(dibenzo[b,d]furan-4-yl)phenyl)-[1,1':4',1"-terphenyl]-4-amine (CAS 1198399-61-9) | JP2014096418 |
| H06 (Fluorescent-blue host material) | Commercially available from Sun Fine Chemicals, Inc, S. Korea |
| H09 (Fluorescent-blue host material) | Commercially available from Sun Fine Chemicals, Inc, S. Korea |
| BD200 (Fluorescent-blue emitter material) | Commercially available from Sun Fine Chemicals, Inc, S. Korea |
| 2-([1,1'-biphenyl]-4-yl)-4-(9,9-diphenyl-9H-fluoren-4-yl)-6-phenyl-1,3,5-triazine (CAS 1801992-44-8) | KR101537500 |
| 8-Hydroxyquinolinolato-lithium (850918-68-2) = Additive-1 = LiQ | WO2013079217 |

The OLED stack is protected from ambient conditions by encapsulation of the device with a glass slide. Thereby, a cavity is formed, which includes a getter material for further protection.

To assess the performance of the inventive examples compared to the existing art, the light output of the top emission OLEDs is measured under ambient conditions (20° C.). Current voltage measurements are performed using a Keithley 2400 sourcemeter, and recorded in V at 10 $mA/cm^2$ for top emission devices, a spectrometer CAS140 CT from Instrument Systems, which has been calibrated by Deutsche Akkreditierungsstelle (DAkkS), is used for measurement of CIE coordinates and brightness in Candela. The current efficiency Ceff is determined at 10 mA/cm2 in cd/A.

In top emission devices, the emission is forward-directed, non-Lambertian and also highly dependent on the micro-cavity. Therefore, the external quantum efficiency (EQE) and power efficiency in lm/W will be higher compared to bottom emission devices.

Technical Effect of the Invention

Material Property

The Tg of compounds of formula 1 (Table 3) are increased versus the comparative compound-1 (Table 2). The values are in a range suitable for use in organic electronic devices. Higher Tg values of materials used in organic electronics are generally preferred for device durability and robustness.

Table 4 shows that the LUMO energy levels and the dipole moments of compounds of formula 1 are in a range suitable for use as hole blocking materials or electron transporting materials in organic electronic devices.

Top Emission Devices

Surprisingly, the operating voltage of top emission OLED devices is reduced when using compounds of formula 1 mixed with the additive LiQ as an electron transport layer. Also, the operating voltage of top emission OLED devices is reduced when using compounds of formula 1 as a hole blocking layer.

Surprisingly, the cd/A current efficiencies were increased when using compounds of formula 1 as a hole blocking layer.

Table 5 shows the operating voltage and cd/A efficiencies of top emission OLED devices comprising a hole blocking layer comprising a compound of formula 1. Table 6 shows the operating voltage of top emission OLED devices comprising an electron transport layer comprising a 1:1 wt % mixture of a compound of formula 1 and LiQ.

In summary, improved performance of top emission OLED devices can be achieved by using compounds of formula 1.

Experimental Data (Overview)

TABLE 2

Properties of comparative compounds

| Compound name | Structure | Tg (° C.) | Tm (° C.) | TRO (° C.) |
|---|---|---|---|---|
| Comparative compound-1 | 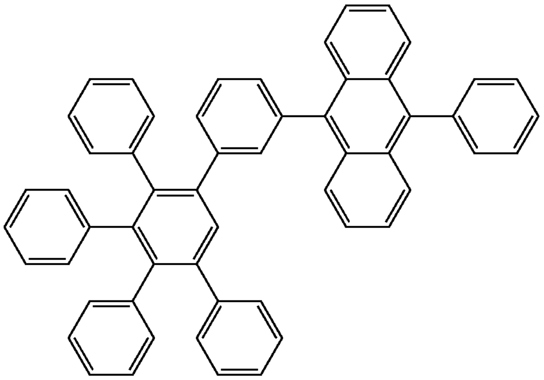 [SMILES: c1ccc(-c2cc(-c3cccc(-c4c5ccccc5c(-c5ccccc5)c5ccccc45)c3)c(-c3ccccc3)c(-c3ccccc3)c2-c2ccccc2)cc1] | 155 | 260 | 210 |
| Comparative compound-2 | 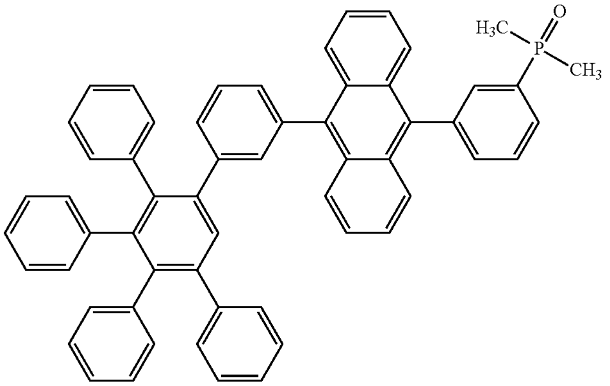 [SMILES: CP(C)(=O)c1cccc(-c2c3ccccc3c(-c3cccc(-c4cc(-c5ccccc5)c(-c5ccccc5)c(-c5ccccc5)c4-c4ccccc4)c3)c3ccccc23)c1] | — | 179 | 258 |

TABLE 3

Properties of compounds of formula 1

| Compound name | Structure | Tg (° C.) | Tm (° C.) | TRO (° C.) |
|---|---|---|---|---|
| Inv-1 | 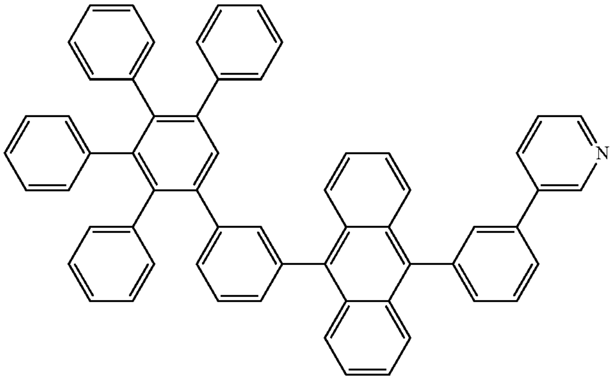 [SMILES: c1ccc(-c2cc(-c3cccc(-c4c5ccccc5c(-c5cccc(-c6cccnc6)c5)c5ccccc45)c3)c(-c3ccccc3)c(-c3ccccc3)c2-c2ccccc2)cc1] | 164 | — | 243 |

TABLE 3-continued
Properties of compounds of formula 1
| Compound name | Structure | Tg (° C.) | Tm (° C.) | TRO (° C.) |
|---|---|---|---|---|
| Inv-2 | 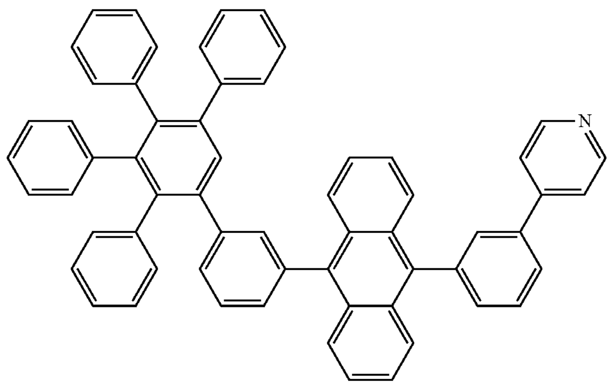 [SMILES: c1ccc(-c2cc(-c3cccc(-c4c5ccccc5c(-c5cccc(-c6ccncc6)c5)c5ccccc45)c3)c(-c3ccccc3)c(-c3ccccc3)c2-c2ccccc2)cc1] | 169 | 200 | 251 |
| Inv-3 | 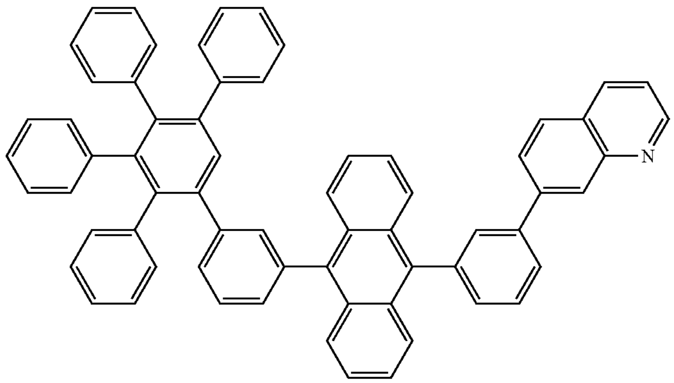 [SMILES: c1ccc(-c2cc(-c3cccc(-c4c5ccccc5c(-c5cccc(-c6ccc7cccnc7c6)c5)c5ccccc45)c3)c(-c3ccccc3)c(-c3ccccc3)c2-c2ccccc2)cc1] | 198 | — | 266 |
| Inv-4 | 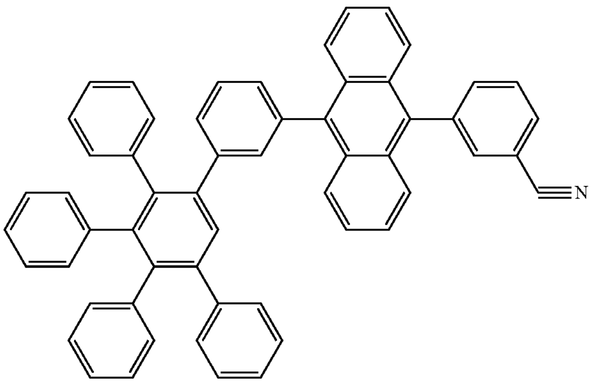 [SMILES: N#Cc1cccc(-c2c3ccccc3c(-c3cccc(-c4cc(-c5ccccc5)c(-c5ccccc5)c(-c5ccccc5)c4-c4ccccc4)c3)c3ccccc23)c1] | 161 | — | 233 |

TABLE 3-continued

| Properties of compounds of formula 1 | | | | |
|---|---|---|---|---|
| Compound name | Structure | Tg (° C.) | Tm (° C.) | TRO (° C.) |
| Inv-5 | 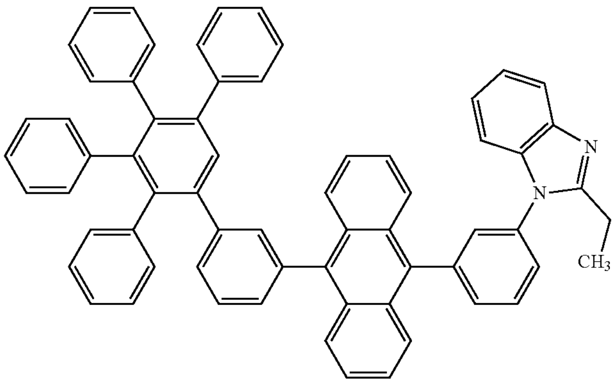 [SMILES: CCc1nc2ccccc2n1-c1cccc(-c2c3ccccc3c(-c3cccc(-c4cc(-c5ccccc5)c(-c5ccccc5)c(-c5ccccc5)c4-c4ccccc4)c3)c3ccccc23)c1] | — | — | — |

TABLE 4

| Energy levels and dipole moments of comparative compounds and compounds of formula 1 | | | |
|---|---|---|---|
| Compound name | HOMO (eV) * | LUMO (eV) * | Dipole moment (Debye) * |
| Comparative compound-1 | −5.04 | −1.55 | 0.59 |
| Comparative compound-2 | −5.24 | −1.75 | 4.92 |
| Inv-1 | −5.09 | −1.61 | 2.69 |
| Inv-2 | −5.18 | −1.70 | 3.43 |
| Inv-3 | −5.01 | −1.54 | 1.79 |
| Inv-4 | −5.31 | −1.82 | 5.60 |
| Inv-5 | −5.25 | −1.76 | 4.46 |

* Values calculated with B3LYP_Gaussian/6-31G*, gas phase

TABLE 5

Operating voltage of top emission organic electroluminescent devices comprising a compound of formula 1 in the hole blocking layer (configuration A).

| | Material of Hole blocking layer | Thickness hole blocking layer (nm) | CIEy | Operating voltage (V) at 10 mA/$cm^2$ | Ceff/CIEy (cd/A) at 0.045 |
|---|---|---|---|---|---|
| Comparative example 1 | Comparative compound-1 | 31 | 0.045 | 4.38 | 126 |
| Comparative example 2 | Comparative compound-2 | 31 | 0.042 | 3.87 | 132 |
| Example 1 | Inv-1 | 31 | 0.046 | 3.78 | 156 |
| Example 2 | Inv-2 | 31 | 0.046 | 3.72 | 154 |
| Example 3 | Inv-3 | 31 | 0.046 | 3.71 | 162 |

TABLE 6

Operating voltage of top emission organic electroluminescent devices comprising a 1:1 wt % mixture of compound of formula 1 with LiQ in the electron transport layer (configuration B).

| | Material of electron transport layer | Mixing ratio (wt-%) | Thickness electron transport layer (nm) | CIEy | Operating voltage at 10 mA/$cm^2$ (V) |
|---|---|---|---|---|---|
| Comparative example 3 | Comparative compound-1: LiQ | 1: 1 | 31 | 0.047 | 4.30 |
| Comparative example 4 | Comparative compound-2: LiQ | 1: 1 | 31 | 0.048 | 4.47 |
| Example 4 | Inv-1:LiQ | 1: 1 | 31 | 0.047 | 3.87 |
| Example 5 | Inv-2:LiQ | 1: 1 | 31 | 0.047 | 3.88 |
| Example 6 | Inv-3:LiQ | 1: 1 | 31 | 0.047 | 4.04 |

From the Table 5 and 6 it can be clearly seen that the inventive compounds allow to build optoelectronic devices with an improved operating voltage as well as efficiency.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. The invention's scope is defined in the following claims and the equivalents thereto. Furthermore, reference signs used in the description and claims do not limit the scope of the invention as claimed.

Means and Methods:

Dipole Moment

The dipole moment $|\vec{\mu}|$ of a molecule containing N atoms is given by:

$$\vec{\mu} = \sum_{i}^{N} q_i \vec{r_i}$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment can be determined by a semi-empirical molecular orbital method.

In the context of the present invention, the dipole moment of a molecule especially means and/or includes that the dipole moment is calculated where geometries of the corresponding molecular structures are optimized using the hybrid functional B3LYP with the 6-31G* basis set as implemented in the program package TURBOMOLE V6.5. If more than one conformation is viable, the conformation with the lowest total energy is selected to determine the bond lengths of the molecules. The dipole moment then can be calculated with said B3LYP_Gaussian/6-31G* program for the gas phase Melting Point The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard $Fc^+/Fc$ redox couple, afforded finally the values reported above. All studied compounds as well as the reported comparative compounds showed well-defined reversible electrochemical behaviour.

The invention claimed is:

1. A compound for an electroluminescent device having the structure:

(I)

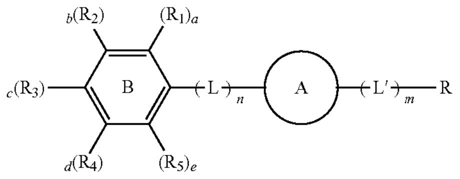

wherein $R^1$ to $R^5$ are independently a substituted or unsubstituted $C_6$ to $C_{30}$ aryl group or a substituted or unsubstituted $C_2$ to $C_{30}$ heteroaryl group, wherein at least two of $R^1$, $R^2$, $R^3$, $R^4$, $R^5$ and L are in ortho-Position to each other at the benzene ring B a to e are independently from each other 0 or 1 and $2 \le a+b+c+d+e \le 5$;

A is a $C_{10}$ to $C_{20}$ arylene group with at least two fused aryl rings;

L and L' are independently selected from each other a $C_2$ to $C_{30}$ heteroaryl group or $C_6$ to $C_{20}$ aryl group n is 1 or 2;

m is 0, 1 or 2, wherein when n or m are 2 then each of the both L and/or L' can be different from the other; and R is selected from substituted or unsubstituted $C_2$ to $C_{30}$ heteroaryl group or CN, wherein R is not substituted or unsubstituted dibenzofuranyl.

2. The compound of claim 1, wherein the compound has a dipole moment of about ≥0.6 Debye.

3. The compound of claim 1, wherein R is chosen so that the dipole moment of the compound R-phenyl is about ≥0.6 Debye.

4. The compound of claim 1, wherein A is selected from the group comprising

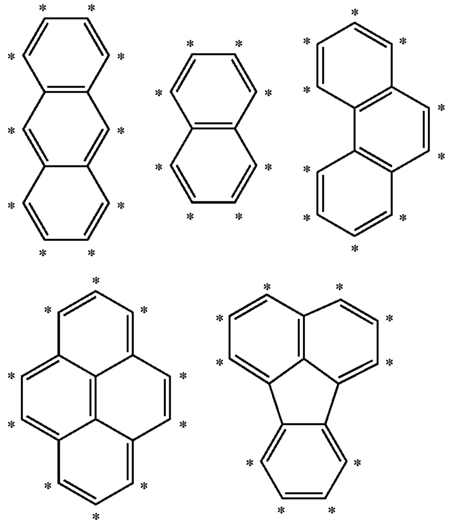

-continued

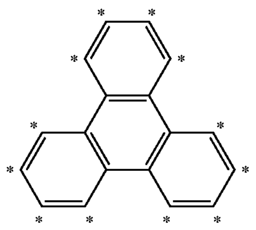

wherein L and L' are linked to any position marked by "*".

5. The compound of claim 1, wherein L and/or L' are selected from the group comprising

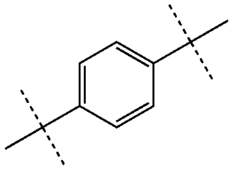
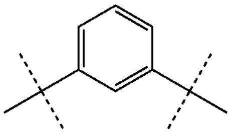
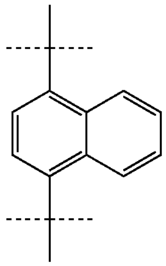
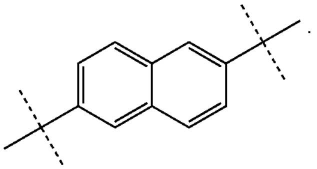

6. The compound of claim 1, wherein 2≤a+b+c+d+e≤4.

7. The compound of claim 1, wherein 2≤a+b+c+d+e≤3.

8. The compound of claim 1, wherein R is selected from substituted $C_2$ to $C_{30}$ heteroaryl group and CN.

9. The compound of claim 1, wherein R is selected from

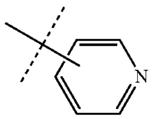
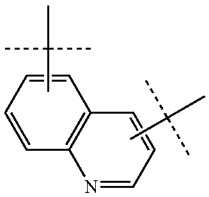
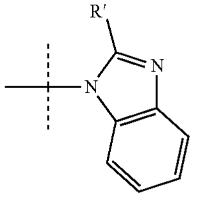
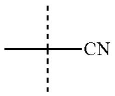
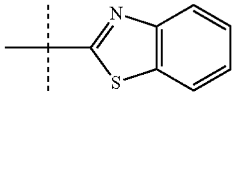
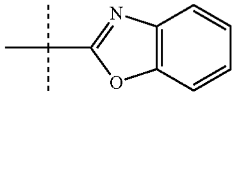

-continued

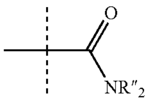
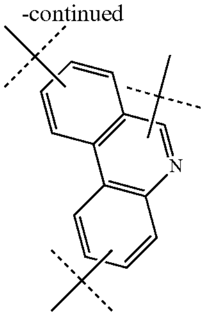
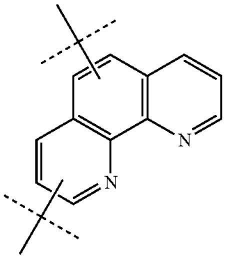
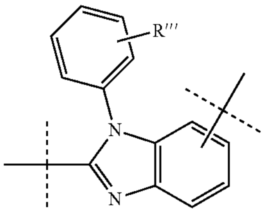
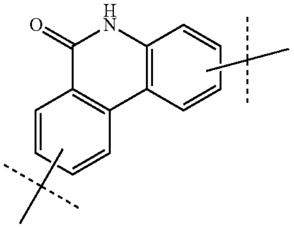

wherein R', is alkyl, cycloalkyl, aryl, heteroaryl; and R" and R'" are independently selected from alkyl, cycloalkyl, aryl, heteroaryl.

10. The compound of claim 1, wherein n is 1.

11. An electronic device comprising a first electrode, a second electrode, and arranged between the first and second electrode, a layer comprising a compound according to claim 1.

12. The electronic device of claim 11, wherein the electronic device comprises a hole blocking layer comprising a compound according to claim 1.

13. The electronic device of claim 11, wherein the electronic device comprises an electron transport layer comprising a compound according to claim 1.

14. The electronic device according to claim 11, wherein the electronic device is an electroluminescent device.

15. The electronic device according to claim 11, wherein the electronic device is an organic light emitting diode.

16. A display device comprising an electronic device according to claim 11.

17. A display device according to claim 16, wherein the display device comprises an organic light emitting diode according to claim 15.

18. The compound of claim 1, wherein R is not substituted or unsubstituted carbazolyl.

* * * * *